US006086890A

United States Patent [19]

Mittal et al.

[11] Patent Number: 6,086,890

[45] **Date of Patent: *Jul. 11, 2000**

[54] BOVINE ADENOVIRUS EXPRESSION VECTOR SYSTEM

[75] Inventors: Suresh K. Mittal, Saskatoon; Frank L. Graham, Hamilton; Ludvik Prevec, Burlington; Lorne A. Babiuk, Saskatoon, all of Canada

[73] Assignee: University of Saskatchewan, Saskatoon, Canada

[ * ] Notice: This patent is subject to a terminal disclaimer.

[21] Appl. No.: 08/815,927

[22] Filed: Mar. 13, 1997

Related U.S. Application Data

[63] Continuation of application No. 08/164,292, Dec. 9, 1993, Pat. No. 5,820,868.

[51] Int. Cl.[7] .......................... A61K 39/235; C12N 7/01; C12N 15/86

[52] U.S. Cl. .................................... 424/199.1; 424/205.1; 424/233.1; 424/93.2; 435/235.1; 435/320.1

[58] Field of Search ............................. 424/199.1, 205.1, 424/233.1, 93.2; 435/320.1, 235.1

[56] References Cited

U.S. PATENT DOCUMENTS

| | | |
|---|---|---|
| 3,962,424 | 6/1976 | Zygraich et al. . |
| 4,510,245 | 4/1985 | Cousens et al. . |
| 4,920,209 | 4/1990 | Davis et al. . |
| 5,024,939 | 6/1991 | Gorman . |

FOREIGN PATENT DOCUMENTS

| | | |
|---|---|---|
| 2012895 | 9/1990 | Canada . |
| 185573 | 6/1986 | European Pat. Off. . |
| 389286 | 9/1990 | European Pat. Off. . |
| 2642797 | 8/1990 | France . |
| 2657880 | 8/1991 | France . |
| 86/06409 | 11/1986 | WIPO . |
| 91/11525 | 8/1991 | WIPO . |

OTHER PUBLICATIONS

Belák et al., "Subtypes of bovine adenovirus type 2 exhibit major differences in region E3" *Virology* (1986) 153:262–271.

Benkö et al., "Molecular Cloning and physical mapping of the DNA of bovine adenovirus serotype 4; study of the DNA homology among bovine, and porcine adenoviruses" *Journal of General Virology* (1990) 71:465–469.

Berkner, K.L., "Development of Adenovirus Vectors for the Expression of Heterologous Genes" *Biotechniques* (1989) 6:616–629.

Bostock, C.J., "Viruses as Vectors" *Vet. Microbiol.* (1990) 23:55–71.

Boyle et al., "Recombinant fowlpox virus vaccines for poultry" *Immunol. Cell Biol.* (1993) 71:391–397.

Boyle et al., "Vectors for Recombinant Vaccine Delivery" *Animal Parasite Control Utilizing Biotechnology,* ed. W.K. Yong CRC Press, Boca Raton (1992) pp. 25–47.

Boyle, D.B., "How do other Poxviruses fit in as Potential Vectored Vaccine Substrates for Animal Immunizations?" *Res. Virol.* (1989) 140(5):483–491.

Esposito et al., "Infectious Recombinant Vectored Virus Vaccines" *Adv. Vet. Sci. Comp. Med.* (1989) 33:195–247.

Fejér et al., "Multiple enlargements in the right inverted terminal repeat of the DNA of canine adenovirus type 2" *Acta Microbiologica Hungarica* (1992) 39:159–168.

Graham et al., "Cloning and expression of glycoprotein genes in human adenovirus vectors" *J. Cell. Biochem.* (1988) UCLA Symposium on Molecular and Cellular Biology, Suppl. 12B, Abstract F109.

Haj–Ahmad et al., "Development of a helper–independent human adenovirus vector and its use in the transfer of the herpes simplex virus thymidine kinase gene" *J. Virol.* (1986) 57:267–274.

Hu et al., "Sequence homology between bovine and human adenoviruses" *J. Virol.* (1984) 49:604–608.

Hu, S.L. et al., "Restriction Analysis and Homology Studies of the Bovine Adenovirus 7 Genome" *J. Virol.* (1984) 51:880–883.

Kaledin, A.S., "Cloning and Sequencing of EIA gene of bovine adenovirus 3 genome" *Sbornik Nauchnykh Trudov–Moskovskaya Veterinaria Akademiya,* (1988) 159:78–82 (translation provided).

Kit, S. et al., "Modified–live infectious bovine rhinotracheitis virus vaccine expressing monomer and dimer forms of foot–and–mouth disease capsid protein epitopes on surface of hybrid virus particles" *Arch. Virol.* (1991) 120:1–17.

Kruglyak, V.A. et al., "Cloning Fragments of Virion DNA of Cattle Adenoviruses BAV 3 In pUC 19 Plasmid" *Soviet Agricultural Sciences* (1987) 11:64–67.

Mittal et al., "Sequence analysis of bovine adenovirus type 3 early region 3 and fibre protein genes" *J. Gen. Virol.* (1992) 73:3295–3300.

Moss, B., "Recombinant DNA virus vectors for vaccination" *Semin. Immunol.* (1990) 2:317–327.

Prevec et al., "Use of human adenovirus–based vectors for antigen expression in animals" *J. Gen. Virol.* (1989) 70:429–434.

Spibey, N. et al., "Identification and nucleotide sequence of the early region 1 from canine adenovirus types 1 and 2" *Virus Research* (1989) 14:241–256.

Thomsen, D.R. et al., "Pseudorabies virus as a live virus vector for expression of foreign genes" *Gene* (1987) 5:261–265.

Tikoo, S.K. et al., "Molecular Cloning, Sequencing, and Expression of Functional Bovine Herpesvirus 1 Glycoprotein gIV in Transfected Bovine Cells" *J. Virol.* (1990) 64:5132–5142.

*Primary Examiner*—Mary E. Mosher

*Attorney, Agent, or Firm*—Morrison & Foerster, LLP

[57] ABSTRACT

The present invention relates novel live bovine adenovirus (BAV) expression vector systems in which part or all of one or both of the early region 1 (E1) and early region 3 (E3) genes are deleted and replaced by a foreign gene or fragment thereof and novel recombinant mammalian cell lines stably transformed with BAV E1 sequences, and therefore, express E1 gene products capable of allowing replication therein of a bovine adenovirus having an E1 deletion replaced by a heterologous nucleotide sequence encoding a foreign gene or fragment thereof and their use in production of (antigenic) polypeptides or fragments thereof for the purpose of live recombinant virus or subunit vaccine or for other therapies.

26 Claims, 51 Drawing Sheets

| 10 | 20 | 30 | 40 | 50 | 60 |
|---|---|---|---|---|---|
| CATCATCAAT | AATCTACAGT | ACACTGATGG | CAGCGGTCCA | ACTGCCAATC | ATTTTTGCCA |

| 70 | 80 | 90 | 100 | 110 | 120 |
|---|---|---|---|---|---|
| CGTCATTTAT | GACGCAACGA | CGGCGAGCGT | GGCGTGCTGA | CGTAACTGTG | GGGCGGAGCG |

| 130 | 140 | 150 | 160 | 170 | 180 |
|---|---|---|---|---|---|
| CGTCGCGGAG | GCGGCGGCGC | TGGGCGGGGC | TGAGGGCGGC | GGGGGCGGCG | CGCGGGGCGG |

| 190 | 200 | 210 | 220 | 230 | 240 |
|---|---|---|---|---|---|
| CGCGCGGGGC | GGGGCGAGGG | GCGGAGTTCC | GCACCCGCTA | CGTCATTTTC | AGACATTTTT |

| 250 | 260 | 270 | 280 | 290 | 300 |
|---|---|---|---|---|---|
| TAGCAAATTT | GCGCCTTTTG | CAAGCATTTT | TCTCACATTT | CAGGTATTTA | GAGGGCGGAT |

| 310 | 320 | 330 | 340 | 350 | 360 |
|---|---|---|---|---|---|
| TTTTGGTGTT | CGTACTTCCG | TGTCACATAG | TTCACTGTCA | ATCTTCATTA | CGGCTTAGAC |

| 370 | 380 | 390 | 400 | 410 | 420 |
|---|---|---|---|---|---|
| AAATTTTCGG | CGTCTTTTCC | GGGTTTATGT | CCCCGGTCAC | CTTTATGACT | GTGTGAAACA |

| 430 | 440 | 450 | 460 | 470 | 480 |
|---|---|---|---|---|---|
| CACCTGCCCA | TTGTTTACCC | TTGGTCAGTT | TTTTCGTCTC | CTAGGGTGGG | AACATCAAGA |

FIG. 1A

```
       490        500        510        520        530        540
ACAAATTTGC CGAGTAATTG TGCACCTTTT TCCGCGTTAG GACTGCGTTT CACACGTAGA

       550        560        570        580        590        600
CAGACTTTTT CTCATTTTCT CACACTCCGT CGTCCGCTTC AGAGCTCTGC GTCTTCGCTG

          610         620         630         640         650
CCACC ATG AAG TAC CTG GTC CTC GTT CTC AAC GAC GGC ATG AGT CGA ATT GAA
      Met Lys Tyr Leu Val Leu Val Leu Asn Asp Gly Met Ser Arg Ile Glu

    660         670         680         690         700
AAA GCT CTC CTG TGC AGC GAT GGT GAG GTG GAT TTA GAG TGT CAT GAG GTA
Lys Ala Leu Leu Cys Ser Asp Gly Glu Val Asp Leu Glu Cys His Glu Val

   710         720         730         740         750
CTT CCC CCT TCT CCC GCG CCT GTC CCC GCT TCT GTG TCA CCC GTG AGG AGT
Leu Pro Pro Ser Pro Ala Pro Val Pro Ala Ser Val Ser Pro Val Arg Ser

  760         770         780         790         800
CCT CCT CCT CTG TCT CCG GTG TTT CCT CCG TCT CCG CCA GCC CCG CTT GTG
Pro Pro Pro Leu Ser Pro Val Phe Pro Pro Ser Pro Pro Ala Pro Leu Val

  810         820         830         840         850
AAT CCA GAG GCG AGT TCG CTG CTG CAG CAG TAT CGG AGA GAG CTG TTA GAG
Asn Pro Glu Ala Ser Ser Leu Leu Gln Gln Tyr Arg Arg Glu Leu Leu Glu
```

FIG. 1B

```
860                 870                 880                 890                 900
AGG AGC CTG CTC CGA ACG GCC GAA GGT CAG CAG CGT GCA GTG TGT CCA TGT
Arg Ser Leu Leu Arg Thr Ala Glu Gly Gln Gln Arg Ala Val Cys Pro Cys

910                 920                 930                 940                 950
GAG CGG TTG CCC GTG GAA GAG GAT GAG TGT CTG AAT GCC GTA AAT TTG CTG
Glu Arg Leu Pro Val Glu Glu Asp Glu Cys Leu Asn Ala Val Asn Leu Leu

960                 970                 980                 990                1000                1010
TTT CCT GAT CCC TGG CTA AAT GCA GCT GAA AAT GGG GGT GAT ATT TTT AAG
Phe Pro Asp Pro Trp Leu Asn Ala Ala Glu Asn Gly Gly Asp Ile Phe Lys

            1020                1030                1040                1050                1060
TCT CCG GCT ATG TCT CCA GAA CCG TGG ATA GAT TTG TCT AGC TAC GAT AGC
Ser Pro Ala Met Ser Pro Glu Pro Trp Ile Asp Leu Ser Ser Tyr Asp Ser

        1070                1080                1090                1100                1110
GAT GTA GAA GAG GTG ACT AGT CAC TTT TTT CTG GAT TGC CCT GAA GAC CCC
Asp Val Glu Glu Val Thr Ser His Phe Phe Leu Asp Cys Pro Glu Asp Pro

        1120                1130                1140                1150                1160
AGT CGG GAG TGT TCA TCT TGT GGG TTT CAT CAG GCT CAA AGC GGA ATT CCA
Ser Arg Glu Cys Ser Ser Cys Gly Phe His Gln Ala Gln Ser Gly Ile Pro
```

FIG. 1C

```
   1170      1180      1190      1200      1210
GGC ATT ATG TGC AGT TTG TGC TAC ATG CGC CAA ACC TAC CAT TGC ATC TAT
Gly Ile Met Cys Ser Leu Cys Tyr Met Arg Gln Thr Tyr His Cys Ile Tyr

   1220       1230       1240       1250       1260       1270
A[GTAAG TACATTCTGT AAAAGAACAT CTTGGTGATT TCTAGGTATT GTTTAGGGAT
S

   1280       1290       1300       1310       1320         1330
TAACTGGGTG GAGTGATCTT AATCCGGCAT AACCAAATAC ATGTTTTCAC AG]GT CCA GTT
                                                           er Pro Val

       1340      1350       1360       1370       1380       1390
TCT GAA GAG GAA ATG TGAGT CATGTTGACT TTGGCGCGC A AGAGGAAATG TGAGTCATGT
Ser Glu Glu Glu Met End

   1400       1410       1420       1430       1440       1450
TGACTTTGGC GCGCCCTACG GTGACTTTAA AGCAATTTGA GGATCACTTT TTTGTTAGTC

   1460       1470       1480       1490       1500
GCTATAAAGT AGTCACGGAG TCTTC ATG GAT CAC TTA AGC GTT CTT TTG GAT TTG
                            Met Asp His Leu Ser Val Leu Leu Asp Leu

 1510       1520       1530       1540       1550
AAG CTG CTT CGC TCT ATC GTA GCG GGG GCT TCA AAT CGC ACT GGA GTG TGG
Lys Leu Leu Arg Ser Ile Val Ala Gly Ala Ser Asn Arg Thr Gly Val Trp
```

FIG. 1D

```
 1560                1570                1580                 1590                1600
 AAG AGG CGG CTG TGG CTG GGA CGC CTG ACT CAA CTG GTC CAT GAT ACC TGC
 Lys Arg Arg Leu Trp Leu Gly Arg Leu Thr Gln Leu Val His Asp Thr Cys

1610                 1620                1630                 1640                1650
 GTA GAG AAC GAG AGC ATA TTT CTC AAT TCT CTG CCA GGG AAT GAA GCT TTT
 Val Glu Asn Glu Ser Ile Phe Leu Asn Ser Leu Pro Gly Asn Glu Ala Phe

1660                 1670                1680                 1690                1700
 TTA AGG TTG CTT CGG AGC GGC TAT TTT GAA GTG TTT GAC GTG TTT GTG GTG
 Leu Arg Leu Leu Arg Ser Gly Tyr Phe Glu Val Phe Asp Val Phe Val Val

1710                 1720                1730                 1740                1750                1760
 CCT GAG CTG CAT CTG GAC ACT CCG GGT CGA GTG GTC GCC GCT CTT GCT CTG
 Pro Glu Leu His Leu Asp Thr Pro Gly Arg Val Val Ala Ala Leu Ala Leu

                 1770                1780                 1790                1800                1810
 CTG GTG TTC ATC CTC AAC GAT TTA GAC GCT AAT TCT GCT TCT TCA GGC TTT
 Leu Val Phe Ile Leu Asn Asp Leu Asp Ala Asn Ser Ala Ser Ser Gly Phe

             1820                1830                 1840                1850                1860
 GAT TCA GGT TTT CTC GTG GAC CGT CTC TGC GTG CCG CTA TGG CTG AAG GCC
 Asp Ser Gly Phe Leu Val Asp Arg Leu Cys Val Pro Leu Trp Leu Lys Ala
                                                     Met Ala Glu Gly
```

FIG. 1E

```
     1870            1880            1890            1900            1910
AGG GCG TTC AAG ATC ACC CAG AGC TCC AGG AGC ACT TCG CAG CCT TCC TCG
Arg Ala Phe Lys Ile Thr Gln Ser Ser Arg Ser Thr Ser Gln Pro Ser Ser
Gln Gly Val Gln Asp His Pro Glu Leu Gln Glu His Phe Ala Ala Phe Leu

     1920            1930            1940            1950            1960
TCG CCC GAC AAG ACG ACC CAG ACT ACC AGC CAG TA GAC GGG GAC AGC CCA
Ser Pro Asp Lys Thr Thr Gln Thr Thr Ser Gln End
Val Ala Arg Gln Asp Asp Pro Asp Tyr Gln Pro Val Asp Gly Asp Ser Pro

     1970            1980            1990            2000            2010
CCC CGG GCT AGC CTG GAG GAG GCT GAA CAG AGC AGC ACT CGT TTC GAG CAC
Pro Arg Ala Ser Leu Glu Glu Ala Glu Gln Ser Ser Thr Arg Phe Glu His

   2020            2030            2040            2050            2060
ATC AGT TAC CGA GAC GTG GTG GAT GAC TTC AAT AGA TGC CAT GAT GTT TTT
Ile Ser Tyr Arg Asp Val Val Asp Asp Phe Asn Arg Cys His Asp Val Phe

   2070            2080            2090            2100            2110
TAT GAG AGG TAC AGT TTT GAG GAC ATA AAG AGC TAC GAG GCT TTG CCT GAG
Tyr Glu Arg Tyr Ser Phe Glu Asp Ile Lys Ser Tyr Glu Ala Leu Pro Glu
```

FIG. 1F

```
2120                2130                2140                2150                2160
GAC AAT TTG GAG CAG CTC ATA GCT ATG CAT GCT AAA ATC AAG CTG CTG CCC
Asp Asn Leu Glu Gln Leu Ile Ala Met His Ala Lys Ile Lys Leu Leu Pro

2170                2180                2190                2200                2210
GGT CGG GAG TAT GAG TTG ACT CAA CCT TTG AAC ATA ACA TCT TGC GCC TAT
Gly Arg Glu Tyr Glu Leu Thr Gln Pro Leu Asn Ile Thr Ser Cys Ala Tyr

2220                2230                2240                2250                2260
GTG CTC GGA AAT GGG GCT ACT ATT AGG GTA ACA GGG GAA GCC TCC CCG GCT
Val Leu Gly Asn Gly Ala Thr Ile Arg Val Thr Gly Glu Ala Ser Pro Ala

2270                2280                2290                2300                2310                2320
ATT AGA GTG GGG GCC ATG GCC GTG GGT CCG TGT GTA ACA GGA ATG ACT GGG
Ile Arg Val Gly Ala Met Ala Val Gly Pro Cys Val Thr Gly Met Thr Gly

            2330                2340                2350                2360                2370
GTG ACT TTT GTG AAT TGT AGG TTT GAG AGA GAG TCA ACA ATT AGG GGG TCC
Val Thr Phe Val Asn Cys Arg Phe Glu Arg Glu Ser Thr Ile Arg Gly Ser

            2380                2390                2400                2410                2420
CTG ATA CGA GCT TCA ACT CAC GTG CTG TTT CAT GGC TGT TAT TTT ATG GGA
Leu Ile Arg Ala Ser Thr His Val Leu Phe His Gly Cys Tyr Phe Met Gly
```

FIG. 1G

```
       2430        2440           2450        2460        2470
ATT ATG GGC ACT TGT ATT GAG GTG GGG GCG GGA GCT TAC ATT CGG GGT TGT
Ile Met Gly Thr Cys Ile Glu Val Gly Ala Gly Ala Tyr Ile Arg Gly Cys

      2480        2490        2500          2510        2520
GAG TTT GTG GGC TGT TAC CGG GGA ATC TGT TCT ACT TCT AAC AGA GAT ATT
Glu Phe Val Gly Cys Tyr Arg Gly Ile Cys Ser Thr Ser Asn Arg Asp Ile

    2530        2540        2550        2560          2570
AAG GTG AGG CAG TGC AAC TTT GAC AAA TGC TTA CTG GGT ATT ACT TGT AAG
Lys Val Arg Gln Cys Asn Phe Asp Lys Cys Leu Leu Gly Ile Thr Cys Lys

   2580        2590          2600        2610        2620
GGG GAC TAT CGT CTT TCG GGA AAT GTG TGT TCT GAG ACT TTC TGC TTT GCT
Gly Asp Tyr Arg Leu Ser Gly Asn Val Cys Ser Glu Thr Phe Cys Phe Ala

  2630         2640        2650          2660        2670
CAT TTA GAG GGA GAG GGT TTG GTT AAA AAC AAC ACA GTC AAG TCC CCT AGT
His Leu Glu Gly Glu Gly Leu Val Lys Asn Asn Thr Val Lys Ser Pro Ser

2680           2690        2700        2710        2720
CGC TGG ACC AGC GAG TCT GGC TTT TCC ATG ATA ACT TGT GCA GAC GGC AGG
Arg Trp Thr Ser Glu Ser Gly Phe Ser Met Ile Thr Cys Ala Asp Gly Arg
```

FIG. 1H

```
2730        2740        2750        2760        2770
GTT ACG CCT TTG GGT TCC CTC CAC ATT GTG GGC AAC CGT TGT AGG CGT TGG
Val Thr Pro Leu Gly Ser Leu His Ile Val Gly Asn Arg Cys Arg Arg Trp

2780        2790        2800        2810        2820        2830
CCA ACC ATG CAG GGG AAT GTG TTT ATC ATG TCT AAA CTG TAT CTG GGC AAC
Pro Thr Met Gln Gly Asn Val Phe Ile Met Ser Lys Leu Tyr Leu Gly Asn

    2840        2850        2860        2870        2880
AGA ATA GGG ACT GTA GCC CTG CCC CAG TGT GCT TTC TAC AAG TCC AGC ATT
Arg Ile Gly Thr Val Ala Leu Pro Gln Cys Ala Phe Tyr Lys Ser Ser Ile

    2890        2900        2910        2920        2930
TGT TTG GAG GAG AGG GCG ACA AAC AAG CTG GTC TTG GCT TGT GCT TTT GAG
Cys Leu Glu Glu Arg Ala Thr Asn Lys Leu Val Leu Ala Cys Ala Phe Glu

    2940        2950        2960        2970        2980
AAT AAT GTA CTG GTG TAC AAA GTG CTG AGA CGG GAG AGT CCC TCA ACC GTG
Asn Asn Val Leu Val Tyr Lys Val Leu Arg Arg Glu Ser Pro Ser Thr Val

    2990        3000        3010        3020        3030
AAA ATG TGT GTT TGT GGG ACT TCT CAT TAT GCA AAG CCT TTG ACA CTG GCA
Lys Met Cys Val Cys Gly Thr Ser His Tyr Ala Lys Pro Leu Thr Leu Ala
```

FIG. 11

```
   3040          3050          3060          3070          3080
ATT ATT TCT TCA GAT ATT CGG GCT AAT CGA TAC ATG TAC ACT GTG GAC TCA
Ile Ile Ser Ser Asp Ile Arg Ala Asn Arg Tyr Met Tyr Thr Val Asp Ser

  3090          3100          3110       3120       3130       3140
ACA GAG TTC ACT TCT GAC GAG GAT T AAAAGTGGGC GGGGCCAAGA GGGGTATAAA
Thr Glu Phe Thr Ser Asp Glu Asp End

      3150       3160       3170       3180       3190       3200
TAGGTGGGGA GGTTGAGGGG AGCCGTAGTT TCTGTTTTTC CCAGACTGGG GGGGACAAC ATG
                                                                 Met

      3210          3220          3230          3240          3250
GCC GAG GAA GGG CGC ATT TAT GTG CCT TAT GTA ACT GCC CGC CTG CCC AAG
Ala Glu Glu Gly Arg Ile Tyr Val Pro Tyr Val Thr Ala Arg Leu Pro Lys

     3260          3270          3280          3290          3300
TGG TCG GGT TCG GTG CAG GAT AAG ACG GGC TCG AAC ATG TTG GGG GGT GTG
Trp Ser Gly Ser Val Gln Asp Lys Thr Gly Ser Asn Met Leu Gly Gly Val

   3310          3320          3330          3340          3350
GTA CTC CCT CCT AAT TCA CAG GCG CAC CGG ACG GAG ACC GTG GGC ACT GAG
Val Leu Pro Pro Asn Ser Gln Ala His Arg Thr Glu Thr Val Gly Thr Glu
```

FIG. 1J

```
 3360                3370                3380               3390               3400
GCC ACC AGA GAC AAC CTG CAC GCC GAG GGA GCG CGT CGT CCT GAG GAT CAG

Ala Thr Arg Asp Asn Leu His Ala Glu Gly Ala Arg Arg Pro Glu Asp Gln


 3410               3420               3430                3440               3450
ACG CCC TAC ATG ATC TTG GTG GAG GAC TCT CTG GGA GGT TTG AAG AGG CGA

Thr Pro Tyr Met Ile Leu Val Glu Asp Ser Leu Gly Gly Leu Lys Arg Arg


3460                3470               3480                3490                3500
ATG GAC TTG CTG GAA GAA TCT AAT CAG CAG CTG CTG GCA ACT CTC AAC CGT

Met Asp Leu Leu Glu Glu Ser Asn Gln Gln Leu Leu Ala Thr Leu Asn Arg


3510                3520                3530                3540               3550
CTC CGT ACA GGA CTC GCT GCC TAT GTG CAG GCT AAC CTT GTG GGC GGC CAA

Leu Arg Thr Gly Leu Ala Ala Tyr Val Gln Ala Asn Leu Val Gly Gly Gln


3560                3570           3580          3590          3600         3610
GTT AAC CCC TTT GTT TAAATA AAAATACACT CATACAGTTT ATTATGCTGT

Val Asn Pro Phe Val End


       3620          3630          3640          3650          3660          3670
CAATAAAATT CTTTATTTTT CCTGTGATAA TACCGTGTCC AGCGTGCTCT GTCAATAAGG

       3680          3690          3700          3710          3720          3730
GTCCTATGCA TCCTGAGAAG GGCCTCATAT ACCCATGGCA TGAATATTAA GATACATGGG
```

FIG. 1K

```
      3740       3750       3760       3770       3780       3790
CATAAGGCCC TCAGAAGGGT TGAGGTAGAG CCACTGCAGA CTTTCGTGGG GAGGTAAGGT

      3800       3810       3820       3830       3840       3850
GTTGTAAATA ATCCAGTCAT ACTGACTGTG CTGGGCGTGG AAGGAAAAGA TGTCTTTTAG

      3860       3870       3880       3890       3900       3910
AAGAAGGGTG ATTGGCAAAG GGAGGCTCTT AGTGTAGGTA TTGATAAATC TGTTCAGTTG

      3920       3930       3940       3950       3960       3970
GGAGGGATGC ATTCGGGGGC TAATAAGGTG GAGTTTAGCC TGAATCTTAA GGTTGGCAAT

      3980       3990       4000       4010       4020       4030
GTTGCCCCCT AGGTCTTTGC GAGGATTCAT GTTGTGCAGT ACCACAAAAA CAGAGTAGCC

      4040       4050       4060
TGTGCATTTG GGGAATTTAT CATGAAGCT T
```

FIG. 1L

```
                              ACTIVATION REGION
Ad5     140                                             153
        GluGluPheValLeuAspTyr   ValGlu         HisProGlyHisGly
         |  |              :     :  :               |     :
        GluGluValThrSerHisPhePheLeuAspCysProGluAspProSerArgGlu
BAV3    155                                             172

                              METAL BINDING REGION
Ad5     154                                                         174
        CysArgSerCysHisTyrHisArgArgAsnThrGlyAspProAspIleMetCysSerLeuCys
         |     |  |     :  |        :  :  |     |     |  |  |  |  |  |
        CysSerSerCysGlyPheHisGlnAlaGlnSerGlyIleProGlyIleMetCysSerLeuCys
BAV3    173                                                         193

                              PROMOTER BINDING REGION
Ad5     175                                          189
        TyrMetArgThrCys   GlyMetPheValTyrSerProValSerGluProGluProGlu
         |  |  |                    :  |  |  |  |  |  |     |
        TyrMetArgGlnThrTyrHisCys   IleTyrSerProValSerGluGluGluMetEnd
BAV3    194                                          208
```

FIG. 2A

```
                          Rb BINDING SEQUENCE
Ad5    120                                132
       IleAspLeuThrCysHisGluAlaGlyPheProProSer
        :  |  |     |  |  |           |  |  |
       ValAspLeuGluCysHisGluVal    LeuProProSer
BAV3   26                                  37
```

FIG. 2B

```
Ad5    82                                                        100
       LeuAspPheSerThrProGlyArgAlaAlaAlaAlaValAlaPheLeuSerPheIle
        |  |        |  |  |  |        |  |     |     |     |  |
       LeuAsp      ThrProGlyArgValValAlaAlaLeuAlaLeuLeuValPheIle
BAV3    83                                                        99
```

FIG. 3A

```
Ad5    20                 26
       GlnSerSerAsnSerThrSer
        |  |  |     |  |  |
       GlnSerSerArgSerThrSer
BAV3   136               142
```

FIG. 3B

```
Ad5 150   GlnLysTyrSerIleGluGlnLeuThrThrTyrTrpLeuGlnProGlyAspAspPheGlu
              :  |  |     |     :     :  |           |     |        |
BAV3 74   GluArgTyrSerPheGluAspIleLysSerTyrGluAlaLeuProGluAspAsnLeuGlu

170       GluAlaIleArgValTyrAlaLysValAlaLeuArgProAspCysLysTyrLysIleSer
                  |     :     |  |  :     |    |           |     :  :
94        GlnLeuIleAlaMetHisAlaLysIleLysLeuLeuProGlyArgGluTyrGluLeuThr

190       LysLeuValAsnIleArgAsnCysCysTyrIleSerGlyAsnGlyAlaGluValGluIle
                  :  |  |        |     |  :     |  |  |  |     :     :
114       GlnProLeuAsnIleThrSerCysAlaTyrValLeuGlyAsnGlyAlaThrIleArgVal

210       AspThrGluAspArgValAlaPheArgCysSerMetIleAsnMetTrpProGlyValLeu
                  |           |     |          :     :     |     |
134       ThrGlyGluAlaSerProAlaIleArgValGlyAlaMetAlaValGlyProCysValThr

230       GlyMetAspGlyValValIleMetAsnValArgPheThr   GlyProAsnPheSerGly
            |  |     |  |        :  |     |  |                      |
154       GlyMetThrGlyValThrPheValAsnCysArgPheGluArgGluSerThrIleArgGly

249       ThrValPheLeuAlaAsnThrAsnLeuIleLeuHisGlyValSerPheTyr   GlyPhe
            :  :        |     |     :  :     |  |        :  :     |
174       SerLeuIleArgAlaSerThrHisValLeuPheHisGlyCys   TyrPheMetGlyIle

268       AsnAsnThrCysValGluAlaTrpThrAspValArgValArgGlyCysAlaPheTyrCys
                  |  |  :  |
193       MetGlyThrCysIleGluValGlyAlaGlyAlaTyrIleArgGlyCysGluPheValGly

288       CysTrpLysGlyValValCysArgProLysSerArgAla   SerIleLysLysCysLeu
            |  :  :  |  :     |                          :  :     |
213       CysTyrArgGlyIle   CysSerThrSerAsnArgAspIleLysValArgGlnCysAsn

307       PheGluArgCysThrLeuGlyIleLeuSerGluGlyAsnSerArgValArgHisAsnVal
            |  :  :  |     |  |  |           |        |  :        |  |
232       PheAspLysCysLeuLeuGlyIleThrCysLysGlyAspTyrArgLeuSerGlyAsnVal

327       AlaSerAspCysGlyCysPheMetLeuValLysSerValAlaValIleLysHisAsnMet
               |  :        |  |        :              :  :  |     |
252       CysSerGluThrPheCysPheAlaHisLeuGluGlyGluGlyLeuValLysAsnAsnThr
```

FIG. 4A

```
347   Val   CysGlyAsn       CysGluAspArgAlaSerGlnMetLeuThrCysSerAsp
       |                             :                |  :  |  |  :  |
272   ValLysSerProSerArgTrpThrSerGluSerGlyPheSerMetIleThrCysAlaAsp

364   GlyAsnCysHisLeuLeuLysThrIleHisVal   AlaSerHisSerArgLysAlaTrp
       |              |   :  :  |  :            :     |  :     |
292   GlyArgValThrProLeuGlySerLeuHisIleValGlyAsnArgCysArgArg   Trp

383   ProValPheGluHisAsnIleLeuHisArgCysSerLeuHisLeuGlyAsnArgArgGly
       |              |  :     .           |     |  |  |  |     |
311   ProThrMetGlnGlyAsnValPheIleMetSerLysLeuTyrLeuGlyAsnArgIleGly

403      ValPheLeuProTyrGlnCysAsnLeuSerHisThrLysIleLeuLeuGluProGlu
          |     |  |     |  |           :  :     |     |  |
331   ThrValAlaLeuPro   GlnCysAlaPheTyrLysSerSerIleCysLeuGluGluArg

422   SerMetSerLysValAsnLeuAsnGlyValPheAspMetThrMetLysIleTrpLysVal
       :        |  :     |           |  :        :     :  :  |  |
350   AlaThrAsnLysLeuValLeuAlaCysAlaPheGluAsnAsnValLeuValTyrLysVal

442   LeuArgTyrAspGluThrArgThrArgCysArgProCysGluCysGlyGlyLysHisIle
       |  |     :           |        :     |     |  |        |
370   LeuArgArgGluSerProSerThr   ValLysMetCysValCysGlyThrSerHisTyr

462   ArgAsnGlnProValMetLeuAspVal   ThrGluGluLeuArgProAspHisLeuVal
                |  :     |     :     :     :  :  |        :     :
389      AlaLysProLeuThrLeuAlaIleIleSerSerAspIleArgAlaAsnArgTyrMet

481   LeuAlaCysHisArgAlaGluPheGlySerSerAspGluAspThrAspEnd
          :           :  |  |     :  |  |  |  |
408   TyrThrValAspSerThrGluPhe   ThrSerAspGluAspEnd
```

FIG. 4B

```
422   SerMetSerLysValAsnLeuAsnGlyValPheAspMetThrMetLysIleTrpLysVal
       :        |  :     |           |  :        :     :  :  |  |
350   AlaThrAsnLysLeuValLeuAlaCysAlaPheGluAsnAsnValLeuValTyrLysVal

442   LeuArgTyrAspGluThrArgThrArgCysArgProCysGluCysGlyGlyLysHisIle
       |  |     :           |        :     |     |  |        |
370   LeuArgArgGluSerProSerThr   ValLysMetCysValCysGlyThrSerHisTyr

462   ArgAsnGlnProValMetLeuAspVal   ThrGluGluLeuArgProAspHisLeuVal
                |  :     |     :     :     :  :  |        :     :
389      AlaLysProLeuThrLeuAlaIleIleSerSerAspIleArgAlaAsnArgTyrMet

481   LeuAlaCysThrArgAlaGluPheGlySerSerAspGluAspThrAspEnd
          :           :  |  |     :  |  |  |  |
408   TyrThrValAspSerThrGluPhe   ThrSerAspGluAspEnd
```

FIG. 4C

```
Ad5     1  MetSerThrAsnSerPheAspGlySerIleValSerSerTyrLeuThrThrArgMetPro
            |  :              :  |     |           |  :  |  :  |  :  |
BAV3    1  MetAla   Glu      GluGlyArgIleTyrValProTyrValThrAlaArgLeuPro

       21  ProTrpAlaGlyValArgGlnAsnValMetGlySerSerIleAspGlyArgProValLeu
               |  :  |        |           |  |     :     |        |  |
       18  LysTrpSerGlySerValGlnAspLysThrGlySerAsnMetLeuGlyGlyValValLeu

       41  ProAlaAsnSerThrThrLeuThrTyrGluThrValSerGlyThrProLeuGluThrAla
            |     |  |     :           |  |  |     |  |           |
       38  ProProAsnSerGlnAlaHisArgThrGluThrVal   GlyThrGlu   AlaThr

       61  AlaSerAlaAlaAlaSerAlaAlaAlaAlaThrAlaArgGlyIleValThrAspPheAla
                              |        |        |
       55     ArgAspAsnLeuHisAlaGluGlyAlaArg   ArgProGluAspGlnThr   Pro

       81  PheLeuSerProLeuAlaSerSerAlaAlaSerArgSerSerAlaArgAspAspLysLeu
            :  :        |           :                    |     |     |
       72  TyrMetIle   LeuValGluAspSerLeuGlyGlyLeuLysArgArgMetAspLeuLeu

      101  ThrAlaLeuLeuAlaGlnLeu   AspSerLeuThrArgGluLeuAsnValValSerGln
                           |  |        :  |     |     |
       91  GluGluSerAsnGlnGlnLeuLeuAlaThrLeuAsnArg   LeuArgThr   Gly

      120  GlnLeuLeuAspLeuArgGlnGlnValSerAlaLeuLysAlaSerSerProProAsnAla
               |                 |     :     |
      108     LeuAlaAlaTyr   ValGln   AlaAsnLeuValGlyGlyGlnValAsnProPhe

      140  ValEnd
            |  |
      125  ValEnd
```

FIG. 5

```
                      10                  20                  30                  40                  50
         C CTC ATC AAA CAA CCC GTG GTG GGC ACC ACC CAC GTG GAA ATG CCT CGC AAC
ORF 1      Leu Ile Lys Gln Pro Val Val Gly Thr Thr His Val Glu Met Pro Arg Asn

                  60                  70                  80                  90                 100
           GAA GTC CTA GAA CAA CAT CTG ACC TCA CAT GGC GCT CAA ATC GCG GGC GGA
           Glu Val Leu Glu Gln His Leu Thr Ser His Gly Ala Gln Ile Ala Gly Gly

               110                 120                 130                 140                 150
           GGC GCT GCG GGC GAT TAC TTT AAA AGC CCC ACT TCA GCT CGA ACC CTT ATC
           Gly Ala Ala Gly Asp Tyr Phe Lys Ser Pro Thr Ser Ala Arg Thr Leu Ile

              160                 170                 180                 190                 200
           CCG CTC ACC GCC TCC TGC TTA AGA CCA GAT GGA GTC TTT CAA CTA GGA GGA
           Pro Leu Thr Ala Ser Cys Leu Arg Pro Asp Gly Val Phe Gln Leu Gly Gly

             210                 220                 230                 240                 250
           GGC TCG CGT TCA TCT TTC AAC CCC CTG CAA ACA GAT TTT GCC TTC CAC GCC
           Gly Ser Arg Ser Ser Phe Asn Pro Leu Gln Thr Asp Phe Ala Phe His Ala

            260                 270                 280                 290                 300
           CTG CCC TCC AGA CCG CGC CAC GGG GGC ATA GGA TCC AGG CAG TTT GTA GAG
           Leu Pro Ser Arg Pro Arg His Gly Gly Ile Gly Ser Arg Gln Phe Val Glu
```

FIG. 7A

```
310           320          330          340           350
GAA TTT GTG CCC GCC GTC TAC CTC AAC CCC TAC TCG GGA CCG CCG GAC TCT
Glu Phe Val Pro Ala Val Tyr Leu Asn Pro Tyr Ser Gly Pro Pro Asp Ser

360          370           380          390          400
TAT CCG GAC CAG TTT ATA CGC CAC TAC AAC GTG TAC AGC AAC TCT GTG AGC
Tyr Pro Asp Gln Phe Ile Arg His Tyr Asn Val Tyr Ser Asn Ser Val Ser
                                                      ORF 2  Ala
410          420          430          440           450         460
GGT TAT AGC T GAG ATT GTA AGA CTC TCC TAT CTG TCT CTG TGC TGC TTT TCC
Gly Tyr Ser
 Val Ile Ala  Glu Ile Val Arg Leu Ser Tyr Leu Ser Leu Cys Cys Phe Ser

        470           480          490          500           510
GCT TCA AGC CCC ACA AGC ATG AAG GGG TTT CTG CTC ATC TTC AGC CTG CTT
Ala Ser Ser Pro Thr Ser Met Lys Gly Phe Leu Leu Ile Phe Ser Leu Leu

       520          530           540          550          560
GTG CAT TGT CCC CTA ATT CAT GTT GGG ACC ATT AGC TTC TAT GCT GCA AGG
              ORF 3  Phe Met Leu Gly Pro Leu Ala Ser Met Leu Gln Gly
Val His Cys Pro Leu Ile His Val Gly Thr Ile Ser Phe Tyr Ala Ala Arg
```

FIG. 7B

```
    570         580         590         600         610
CCC GGG TCT GAG CCT AAC GCG ACT TAT GTT TGT GAC TAT GGA AGC GAG TCA
 Pro Gly Leu Ser Leu Thr Arg Leu Met Phe Val Thr Met Glu Ala Ser Gln
Pro Gly Ser Glu Pro Asn Ala Thr Tyr Val Cys Asp Tyr Gly Ser Glu Ser

  620         630         640         650         660
GAT TAC AAC CCC ACC ACG GTT CTG TGG TTG GCT CGA GAG ACC GAT GGC TCC
 Ile Thr Thr Pro Pro Arg Phe Cys Gly Trp Leu Glu Arg Pro Met Ala Pro
Asp Tyr Asn Pro Thr Thr Val Leu Trp Leu Ala Arg Glu Thr Asp Gly Ser

  670         680         690         700         710
TGG ATC TCT GTT CTT TTC CGT CAC AAC GGC TCC TCA ACT GCA GCC CCC GGG
 Gly Ser Leu Phe Phe Ser Val Thr Thr Ala Pro Gln Leu Gln Pro Pro Gly
Trp Ile Ser Val Leu Phe Arg His Asn Gly Ser Ser Thr Ala Ala Pro Gly

 720         730         740         750         760
GTC GTC GCG CAC TTT ACT GAC CAC AAC AGC AGC ATT GTG GTG CCC CAG TAT
 Ser Ser Arg Thr Leu Leu Thr Thr Thr Ala Ala Leu Trp Cys Pro Ser Ile
Val Val Ala His Phe Thr Asp His Asn Ser Ser Ile Val Val Pro Gln Tyr

770         780         790         800         810
TAC CTC CTC AAC AAC TCA CTC TCT AAG CTC TGC TGC TCA TAC CGG CAC AAC
 Thr Ser Ser Thr Thr His Ser Leu Ser Ser Ala Ala His Thr Gly Thr Thr
Tyr Leu Leu Asn Asn Ser Leu Ser Lys Leu Cys Cys Ser Tyr Arg His Asn
```

FIG. 7C

```
820         830         840         850         860
GAG CGT TCT CAG TTT ACC TGC AAA CAA GCT GAC GTC CCT ACC TGT CAC GAG
 Ser Val Leu Ser Leu Pro Ala Asn Lys Leu Thr Ser Leu Pro Val Thr Ser
Glu Arg Ser Gln Phe Thr Cys Lys Gln Ala Asp Val Pro Thr Cys His Glu

870         880         890         900         910         920
CCC GGC AAG CCG CTC ACC CTC CGC GTC TCC CCC GCG CTG GGA ACT GCC CAC
  Pro Ala Ser Arg Ser Pro Ser Ala Ser Pro Pro Arg Trp Glu Leu Pro Thr
Pro Gly Lys Pro Leu Thr Leu Arg Val Ser Pro Ala Leu Gly Thr Ala His

            930         940         950         960         970
CAA GCA GTC ACT TGG TTT TTT CAA AAT GTA CCC ATA GCT ACT GTT TAC CGA
 Lys Gln Ser Leu Gly Phe Phe Lys Met Tyr Pro
Gln Ala Val Thr Trp Phe Phe Gln Asn Val Pro Ile Ala Thr Val Tyr Arg

        980         990         1000        1010        1020
CCT TGG GGC AAT GTA ACT TGG TTT TGT CCT CCC TTC ATG TGT ACC TTT AAT
Pro Trp Gly Asn Val Thr Trp Phe Cys Pro Pro Phe Met Cys Thr Phe Asn

      1030        1040        1050        1060        1070
GTC AGC CTG AAC TCC CTA CTT ATT TAC AAC TTT TCT GAC AAA ACC GGG GGG
Val Ser Leu Asn Ser Leu Leu Ile Tyr Asn Phe Ser Asp Lys Thr Gly Gly
```

FIG. 7D

```
        1080                1090                1100                  1110                1120
CAA TAC ACA GCT CTC ATG CAC TCC GGA CCT GCT TCC CTC TTT CAG CTC TTT
Gln Tyr Thr Ala Leu Met His Ser Gly Pro Ala Ser Leu Phe Gln Leu Phe

     1130               1140                1150                1160                1170
AAG CCA ACG ACT TGT GTC ACC AAG GTG GAG GAC CCG CCG TAT GCC AAC GAC
Lys Pro Thr Thr Cys Val Thr Lys Val Glu Asp Pro Pro Tyr Ala Asn Asp

   1180               1190                1200                1210                1220
CCG GCC TCG CCT GTG TGG CGC CCA CTG CTT TTT GCC TTC GTC CTC TGC ACC
Pro Ala Ser Pro Val Trp Arg Pro Leu Leu Phe Ala Phe Val Leu Cys Thr

  1230               1240                1250                  1260                1270
GGC TGC GCG GTG TTG TTA ACC GCC TTC GGT CCA TCG ATT CTA TCC GGT ACC
                    ORF 4  Pro Pro Ser Val His Arg Phe Tyr Pro Val Pro
Gly Cys Ala Val Leu Leu Thr Ala Phe Gly Pro Ser Ile Leu Ser Gly Thr

1280               1290                1300                1310                 1320
CGA AAG CTT ATC TCA GCC CGC TTT TGG AGT CCC GAG CCC TAT ACC ACC CTC
 Glu Ser Leu Ser Gln Pro Ala Phe Gly Val Pro Ser Pro Ile Pro Pro Ser
Arg Lys Leu Ile Ser Ala Arg Phe Trp Ser Pro Glu Pro Tyr Thr Thr Leu
```

FIG. 7E

```
1330          1340          1350          1360          1370          1380
 CAC T AAC AGT CCC CCC ATG GAG CCA GAC GGA GTT CAT GCC GAG CAG CAG TTT
  Thr  Asn Ser Pro Pro Met Glu Pro Asp Gly Val His Ala Glu Gln Gln Phe
 His

            1390          1400          1410          1420          1430
 ATC CTC AAT CAG ATT TCC TGC GCC AAC ACT GCC CTC CAG CGT CAA AGG GAG
 Ile Leu Asn Gln Ile Ser Cys Ala Asn Thr Ala Leu Gln Arg Gln Arg Glu

          1440          1450          1460          1470          1480
 GAA CTA GCT TCC CTT GTC ATG TTG CAT GCC TGT AAG CGT GGC CTC TTT TGT
 Glu Leu Ala Ser Leu Val Met Leu His Ala Cys Lys Arg Gly Leu Phe Cys
   ORF 5  Leu Pro Leu Ser Cys Cys Met Pro Val Ser Val Ala Ser Phe Val

         1490          1500          1510          1520          1530
 CCA GTC AAA ACT TAC AAG CTC AGC CTC AAC GCC TCG GCC AGC GAG CAC AGC
 Pro Val Lys Thr Tyr Lys Leu Ser Leu Asn Ala Ser Ala Ser Glu His Ser
  Gln Ser Lys Leu Thr Ser Ser Ala Ser Thr Pro Arg Pro Ala Ser Thr Ala

        1540          1550          1560          1570          1580
 CTG CAC TTT GAA AAA AGT CCC TCC CGA TTC ACC CTG GTC AAC ACT CAC GCC
 Leu His Phe Glu Lys Ser Pro Ser Arg Phe Thr Leu Val Asn Thr His Ala
  Cys Thr Leu Lys Lys Val Pro Pro Asp Ser Pro Trp Ser Thr Leu Thr Pro
```

FIG. 7F

```
   1590        1600        1610       1620        1630
GGA GCT TCT GTG CGA GTG GCC CTA CAC CAC CAG GGA GCT TCC GGC AGC ATC
Gly Ala Ser Val Arg Val Ala Leu His His Gln Gly Ala Ser Gly Ser Ile
 Glu Leu Leu Cys Glu Trp Pro Tyr Thr Thr Arg Glu Leu Pro Ala Ala Ser

 1640       1650        1660       1670        1680
CGC TGT TCC TGT TCC CAC GCC GAG TGC CTC CCC GTC CTC CTC AAG ACC CTC
Arg Cys Ser Cys Ser His Ala Glu Cys Leu Pro Val Leu Leu Lys Thr Leu
 Ala Val Pro Val Pro Thr Pro Ser Ala Ser Pro Ser Ser Ser Arg Pro Ser

 1690       1700       1710       1720        1730       1740
TGT GCC TTT AAC TTT TTA GAT TAG CTGAAAGCAA ATATAAAATG GTGTGCTTAC
Cys Ala Phe Asn Phe Leu Asp
 Val Pro Leu Thr Phe

    1750       1760       1770       1780        1790
CGTAATTCTG TTTTGACTTG TGTGCTTGA TTT CTC CCC CTG CGC CGT AAT CCA GTG

 1800       1810       1820       1830        1840
CCC CTC TTC AAA ACT CTC GTA CCC TAT GCG ATT CGC ATA GGC ATA TTT TCT

1850        1860       1870       1880        1890
 AAA AGC TCT GAA GTC AAC ATC ACT CTC AAA CAC TTC TCC GTT GTA GGT TAC
```

FIG. 7G

```
1900      1910       1920       1930      1940      1950
 TTT CAT CTA CAG ATA AAG TCA TCC ACC GGT T AAC ATC ATG AAG AGA AGT GTG
                 ORF 6  Ser His Pro Pro Val  Asn Ile Met Lys Arg Ser Val

           1960       1970       1980       1990       2000
 CCC CAG GAC TTT AAT CTT GTG TAT CCG TAC AAG GCT AAG AGG CCC AAC ATC
 Pro Gln Asp Phe Asn Leu Val Tyr Pro Tyr Lys Ala Lys Arg Pro Asn Ile

         2010        2020       2030       2040        2050
 ATG CCG CCC TTT TTT GAC CGC AAT GGC TTT GTT GAA AAC CAA GAA GCC ACG
 Met Pro Pro Phe Phe Asp Arg Asn Gly Phe Val Glu Asn Gln Glu Ala Thr

        2060       2070        2080       2090       2100
 CTA GCC ATG CTT GTG GAA AAG CCG CTC ACG TTC GAC AAG GAA GGT GCG CTG
 Leu Ala Met Leu Val Glu Lys Pro Leu Thr Phe Asp Lys Glu Gly Ala Leu

       2110       2120       2130        2140       2150
 ACC CTG GGC GTC GGA CGC GGC ATC CGC ATT AAC CCC GCG GGG CTT CTG GAG
 Thr Leu Gly Val Gly Arg Gly Ile Arg Ile Asn Pro Ala Gly Leu Leu Glu

     2160       2170       2180       2190        2200
 ACA AAC GAC CTC GCG TCC GCT GTC TTC CCA CCG CTG GCC TCC GAT GAG GCC
 Thr Asn Asp Leu Ala Ser Ala Val Phe Pro Pro Leu Ala Ser Asp Glu Ala
```

FIG. 7H

```
2210                2220                  2230                2240                2250
GGC AAC GTC ACG CTC AAC ATG TCT GAC GGG CTA TAT ACT AAG GAC AAC AAG
Gly Asn Val Thr Leu Asn Met Ser Asp Gly Leu Tyr Thr Lys Asp Asn Lys

2260                2270                2280                  2290                2300
CTA GCT GTC AAA GTA GGT CCC GGG CTG TCC CTC GAC TCC AAT AAT GCT CTC
Leu Ala Val Lys Val Gly Pro Gly Leu Ser Leu Asp Ser Asn Asn Ala Leu

2310                2320                2330                2340                  2350
CAG GTC CAC ACA GGC GAC GGG CTC ACG GTA ACC GAT GAC AAG GTG TCT CTA
Gln Val His Thr Gly Asp Gly Leu Thr Val Thr Asp Asp Lys Val Ser Leu

2360                2370                  2380                2390                2400
AAT ACC CAA GCT CCC CTC TCG ACC ACC AGC GCG GGC CTC TCC CTA CTT CTG
Asn Thr Gln Ala Pro Leu Ser Thr Thr Ser Ala Gly Leu Ser Leu Leu Leu

2410                2420                2430                  2440                2450                2460
GGT CCC AGC CTC CAC TTA GGT GAG GAG GAA CGA CTA ACA GTA AAC ACC GGA
Gly Pro Ser Leu His Leu Gly Glu Glu Glu Arg Leu Thr Val Asn Thr Gly

            2470                2480                2490                  2500                2510
GCG GGC CTC CAA ATT AGC AAT AAC GCT CTG GCC GTA AAA GTA GGT TCA GGT
Ala Gly Leu Gln Ile Ser Asn Asn Ala Leu Ala Val Lys Val Gly Ser Gly
```

FIG. 7I

```
                 2520                2530                2540                2550                2560
ATC ACC GTA GAT GCT CAA AAC CAG CTC GCT GCA TCC CTG GGG GAC GGT CTA
Ile Thr Val Asp Ala Gln Asn Gln Leu Ala Ala Ser Leu Gly Asp Gly Leu

             2570                2580                2590                2600                2610
GAA AGC AGA GAT AAT AAA ACT GTC GTT AAG GCT GGG CCC GGA CTT ACA ATA
Glu Ser Arg Asp Asn Lys Thr Val Val Lys Ala Gly Pro Gly Leu Thr Ile

         2620                2630                2640                2650                2660
ACT AAT CAA GCT CTT ACT GTT GCT ACC GGG AAC GGC CTT CAG GTC AAC CCG
Thr Asn Gln Ala Leu Thr Val Ala Thr Gly Asn Gly Leu Gln Val Asn Pro

     2670                2680                2690                2700                2710
GAA GGG CAA CTG CAG CTA AAC ATT ACT GCC GGT CAG GGC CTC AAC TTT GCA
Glu Gly Gln Leu Gln Leu Asn Ile Thr Ala Gly Gln Gly Leu Asn Phe Ala

  2720                2730                2740                2750                2760
AAC AAC AGC CTC GCC GTG GAG CTG GGC TCG GGC CTG CAT TTT CCC CCT GGC
Asn Asn Ser Leu Ala Val Glu Leu Gly Ser Gly Leu His Phe Pro Pro Gly

2770                2780                2790                2800                2810
CAA AAC CAA GTA AGC CTT TAT CCC GGA GAT GGA ATA GAC ATC CGA GAT AAT
Gln Asn Gln Val Ser Leu Tyr Pro Gly Asp Gly Ile Asp Ile Arg Asp Asn
```

FIG. 7J

```
2820                2830                2840                2850                2860
AGG GTG ACT GTG CCC GCT GGG CCA GGC CTG AGA ATG CTC AAC CAC CAA CTT
Arg Val Thr Val Pro Ala Gly Pro Gly Leu Arg Met Leu Asn His Gln Leu

2870                2880                2890                2900                2910
GCC GTA GCT TCC GGA GAC GGT TTA GAA GTC CAC AGC GAC ACC CTC CGG TTA
Ala Val Ala Ser Gly Asp Gly Leu Glu Val His Ser Asp Thr Leu Arg Leu

2920                2930                2940                2950                2960                2970
AAG CTC TCC CAC GGC CTG ACA TTT GAA AAT GGC GCC GTA CGA GCA AAA CTA
Lys Leu Ser His Gly Leu Thr Phe Glu Asn Gly Ala Val Arg Ala Lys Leu

            2980                2990                3000                3010                3020
GGA CCA GGA CTT GGC ACA GAC GAC TCT GGT CGG TCC GTG GTT CGC ACA GGT
Gly Pro Gly Leu Gly Thr Asp Asp Ser Gly Arg Ser Val Val Arg Thr Gly

        3030                3040                3050                3060                3070
CGA GGA CTT AGA GTT GCA AAC GGC CAA GTC CAG ATC TTC AGC GGA AGA GGC
Arg Gly Leu Arg Val Ala Asn Gly Gln Val Gln Ile Phe Ser Gly Arg Gly

      3080                3090                3100                3110                3120
ACC GCC ATC GGC ACT GAT AGC AGC CTC ACT CTC AAC ATC CGG GCG CCC CTA
Thr Ala Ile Gly Thr Asp Ser Ser Leu Thr Leu Asn Ile Arg Ala Pro Leu
```

FIG. 7K

```
   3130       3140       3150        3160       3170
CAA TTT TCT GGA CCC GCC TTG ACT GCT AGT TTG CAA GGC AGT GGT CCG ATT

Gln Phe Ser Gly Pro Ala Leu Thr Ala Ser Leu Gln Gly Ser Gly Pro Ile

  3180       3190       3200       3210       3220
ACT TAC AAC AGC AAC AAT GGC ACT TTC GGT CTC TCT ATA GGC CCC GGA ATG

Thr Tyr Asn Ser Asn Asn Gly Thr Phe Gly Leu Ser Ile Gly Pro Gly Met

 3230       3240       3250       3260       3270
TGG GTA GAC CAA AAC AGA CTT CAG GTA AAC CCA GGC GCT GGT TTA GTC TTC

Trp Val Asp Gln Asn Arg Leu Gln Val Asn Pro Gly Ala Gly Leu Val Phe

 3280       3290       3300       3310       3320
CAA GGA AAC AAC CTT GTC CCA AAC CTT GCG GAT CCG CTG GCT ATT TCC GAC

Gln Gly Asn Asn Leu Val Pro Asn Leu Ala Asp Pro Leu Ala Ile Ser Asp

3330       3340       3350       3360       3370
AGC AAA ATT AGT CTC AGT CTC GGT CCC GGC CTG ACC CAA GCT TCC AAC GCC

Ser Lys Ile Ser Leu Ser Leu Gly Pro Gly Leu Thr Gln Ala Ser Asn Ala

3380       3390       3400       3410       3420
CTG ACT TTA AGT TTA GGA AAC GGG CTT GAA TTC TCC AAT CAA GCC GTT GCT

Leu Thr Leu Ser Leu Gly Asn Gly Leu Glu Phe Ser Asn Gln Ala Val Ala
```

FIG. 7L

```
3430        3440        3450        3460        3470        3480
ATA AAA GCG GGC CGG GGC TTA CGC TTT GAG TCT TCC TCA CAA GCT TTA GAG
Ile Lys Ala Gly Arg Gly Leu Arg Phe Glu Ser Ser Ser Gln Ala Leu Glu

        3490        3500        3510        3520        3530
AGC AGC CTC ACA GTC GGA AAT GGC TTA ACG CTT ACC GAT ACT GTG ATC CGC
Ser Ser Leu Thr Val Gly Asn Gly Leu Thr Leu Thr Asp Thr Val Ile Arg

      3540        3550        3560        3570        3580
CCC AAC CTA GGG GAC GGC CTA GAG GTC AGA GAC AAT AAA ATC ATT GTT AAG
Pro Asn Leu Gly Asp Gly Leu Glu Val Arg Asp Asn Lys Ile Ile Val Lys

     3590        3600        3610        3620        3630
CTG GGC GCG AAT CTT CGT TTT GAA AAC GGA GCC GTA ACC GCC GGC ACC GTT
Leu Gly Ala Asn Leu Arg Phe Glu Asn Gly Ala Val Thr Ala Gly Thr Val

    3640        3650        3660        3670        3680
AAC CCT TCT GCG CCC GAG GCA CCA CCA ACT CTC ACT GCA GAA CCA CCC CTC
Asn Pro Ser Ala Pro Glu Ala Pro Pro Thr Leu Thr Ala Glu Pro Pro Leu

   3690        3700        3710        3720        3730
CGA GCC TCC AAC TCC CAT CTT CAA CTG TCC CTA TCG GAG GGC TTG GTT GTG
Arg Ala Ser Asn Ser His Leu Gln Leu Ser Leu Ser Glu Gly Leu Val Val
```

FIG. 7M

```
 3740                3750                3760                3770                3780
CAT AAC AAC GCC CTT GCT CTC CAA CTG GGA GAC GGC ATG GAA GTA AAT CAG

His Asn Asn Ala Leu Ala Leu Gln Leu Gly Asp Gly Met Glu Val Asn Gln

 3790                3800                3810                3820                3830
CAC GGA CTT ACT TTA AGA GTA GGC TCG GGT TTG CAA ATG CGT GAC GGC ATT

His Gly Leu Thr Leu Arg Val Gly Ser Gly Leu Gln Met Arg Asp Gly Ile

3840                3850                3860                3870                3880
TTA ACA GTT ACA CCC AGC GGC ACT CCT ATT GAG CCC AGA CTG ACT GCC CCA

Leu Thr Val Thr Pro Ser Gly Thr Pro Ile Glu Pro Arg Leu Thr Ala Pro

3890                3900                3910                3920                3930
CTG ACT CAG ACA GAG AAT GGA ATC GGG CTC GCT CTC GGC GCC GGC TTG GAA

Leu Thr Gln Thr Glu Asn Gly Ile Gly Leu Ala Leu Gly Ala Gly Leu Glu

3940                3950                3960                3970                3980                3990
TTA GAC GAG AGC GCG CTC CAA GTA AAA GTT GGG CCC GGC ATG CGC CTG AAC

Leu Asp Glu Ser Ala Leu Gln Val Lys Val Gly Pro Gly Met Arg Leu Asn

        4000                4010                4020                4030                4040
CCT GTA GAA AAG TAT GTA ACC CTG CTC CTG GGT CCT GGC CTT AGT TTT GGG

Pro Val Glu Lys Tyr Val Thr Leu Leu Leu Gly Pro Gly Leu Ser Phe Gly
```

FIG. 7N

```
     4050            4060            4070            4080            4090
CAG CCG GCC AAC AGG ACA AAT TAT GAT GTG CGC GTT TCT GTG GAG CCC CCC
Gln Pro Ala Asn Arg Thr Asn Tyr Asp Val Arg Val Ser Val Glu Pro Pro

    4100            4110            4120            4130            4140
ATG GTT TTC GGA CAG CGT GGT CAG CTC ACA TTT TTA GTG GGT CAC GGA CTA
Met Val Phe Gly Gln Arg Gly Gln Leu Thr Phe Leu Val Gly His Gly Leu

   4150            4160            4170            4180            4190
CAC ATT CAA AAT TCC AAA CTT CAG CTC AAT TTG GGA CAA GGC CTC AGA ACT
His Ile Gln Asn Ser Lys Leu Gln Leu Asn Leu Gly Gln Gly Leu Arg Thr

  4200            4210            4220            4230            4240
GAC CCC GTC ACC AAC CAG CTG GAA GTG CCC CTC GGT CAA GGT TTG GAA ATT
Asp Pro Val Thr Asn Gln Leu Glu Val Pro Leu Gly Gln Gly Leu Glu Ile

 4250            4260            4270            4280            4290
GCA GAC GAA TCC CAG GTT AGG GTT AAA TTG GGC GAT GGC CTG CAG TTT GAT
Ala Asp Glu Ser Gln Val Arg Val Lys Leu Gly Asp Gly Leu Gln Phe Asp

4300            4310            4320            4330            4340
TCA CAA GCT CGC ATC ACT ACC GCT CCT AAC ATG GTC ACT GAA ACT CTG TGG
Ser Gln Ala Arg Ile Thr Thr Ala Pro Asn Met Val Thr Glu Thr Leu Trp
```

FIG. 70

```
4350                4360              4370              4380                4390
ACC GGA ACA GGC AGT AAT GCT AAT GTT ACA TGG CGG GGC TAC ACT GCC CCC
Thr Gly Thr Gly Ser Asn Ala Asn Val Thr Trp Arg Gly Tyr Thr Ala Pro

4400            4410              4420              4430              4440
GGC AGC AAA CTC TTT TTG AGT CTC ACT CGG TTC AGC ACT GGT CTA GTT TTA
Gly Ser Lys Leu Phe Leu Ser Leu Thr Arg Phe Ser Thr Gly Leu Val Leu

4450            4460              4470                4480              4490              4500
GGA AAC ATG ACT ATT GAC AGC AAT GCA TCC TTT GGG CAA TAC ATT AAC GCG
Gly Asn Met Thr Ile Asp Ser Asn Ala Ser Phe Gly Gln Tyr Ile Asn Ala

            4510              4520              4530                4540              4550
GGA CAC GAA CAG ATC GAA TGC TTT ATA TTG TTG GAC AAT CAG GGT AAC CTA
Gly His Glu Gln Ile Glu Cys Phe Ile Leu Leu Asp Asn Gln Gly Asn Leu

          4560              4570              4580              4590                4600
AAA GAA GGA TCT AAC TTG CAA GGC ACT TGG GAA GTG AAG AAC AAC CCC TCT
Lys Glu Gly Ser Asn Leu Gln Gly Thr Trp Glu Val Lys Asn Asn Pro Ser

        4610              4620                4630              4640              4650
GCT TCC AAA GCT GCT TTT TTG CCT TCC ACC GCC CTA TAC CCC ATC CTC AAC
Ala Ser Lys Ala Ala Phe Leu Pro Ser Thr Ala Leu Tyr Pro Ile Leu Asn
```

FIG. 7P

```
  4660                4670                4680                  4690                4700
GAA AGC CGA GGG AGT CTT CCT GGA AAA AAT CTT GTG GGC ATG CAA GCC ATA

Glu Ser Arg Gly Ser Leu Pro Gly Lys Asn Leu Val Gly Met Gln Ala Ile

  4710                  4720                4730                4740                4750
CTG GGA GGC GGG GGC ACT TGC ACT GTG ATA GCC ACC CTC AAT GGC AGA CGC

Leu Gly Gly Gly Gly Thr Cys Thr Val Ile Ala Thr Leu Asn Gly Arg Arg

  4760                4770                4780                4790                4800
AGC AAC AAC TAT CCC GCG GGC CAG TCC ATA ATT TTC GTG TGG CAA GAA TTC

Ser Asn Asn Tyr Pro Ala Gly Gln Ser Ile Ile Phe Val Trp Gln Glu Phe

 4810                 4820                4830                4840                4850
AAC ACC ATA GCC CGC CAA CCT CTG AAC CAC TCT ACA CTT ACT TTT TCT TAC

Asn Thr Ile Ala Arg Gln Pro Leu Asn His Ser Thr Leu Thr Phe Ser Tyr

4860                 4870                4880                 4890                4900
TGG ACT TA AAT AAG TTG GAA ATA AAG AGT TAA ACT GAA TGT TTA AGT GCA

Trp Thr

4910                 4920                4930                4940                  4950
ACA GAC TTT TAT TGG TTT TGG CTC ACA ACA AAT TAC AAC AGC ATA GAC AAG

4960                 4970                4980                4990                5000
TCA TAC CGG TCA AAC AAC ACA GGC TCT CGA AAA CGG GCT AAC CGC TCC AAG
```

FIG. 7Q

```
5010          5020          5030          5040          5050          5060
   AAT CTG TCA CGC AGA CGA GCA AGT CCT AAA TGT TTT TTC ACT CTC TTC GGG

                 5070          5080          5090          5100
   GCC AAG TTC AGC ATG TAT CGG ATT TTC TGC TTA CAC CTT T
```

FIG. 7R

```
Ad2     MSKEIPTPYMWSYQPQMGLAAGAAQDYSTRINYMSAGPHMISRVNGIRAH   50

BAV3        LIKQPVVGTTHV-----------------------EMPRNEVLEQH   23
            :. :  . ::                          .::    :
Ad2     RNRILLEQAAITTTPRNNLNPRSWPAALVYQESPAPTTVVLPRDAQAEVQ  100

BAV3    LTSHGAQIAGGG-----AAGDYFKSPTSARTLIPLTASCL------RPDG   62
        .:  :::.:::      . :            : :    .      ::::
Ad2     MTNSGAQLAGGFRHRVRSPGQGITHLKIRGRGIQLNDESVSSSLGLRPDG  150

BAV3    VFQLGGGSRSSFNPLQTDFAFHALPSRPRHGGIGSRQFVEEFVPAVYLNP  112
         ::.::  :::: : :.  .  .  : :: ::::. ::.:::::.:: ::
Ad2     TFQIGGAGRSSFTPRQAILTLQTSSSEPRSGGIGTLQFIEEFVPSVYFNP  200

BAV3    YSGPPDSYPDQFIRHYNVYSNSVSGYS  139
        .::::  ::::::  .     :  ::
Ad2     FSGPPGHYPDQFIPNFDAVKDSADGYD  227
```

FIG. 8A

```
BAV3    M------EPDGVHAEQQFILNQISCANTALQRQREELASLVMLHACKRGL   77
        :      : ::. .::  .      : .  ::   ::  .: :: ::::.
Ad5     MTDTLDLEMDGIITEQRLL--ERRRAAAEQQRMNQELQDMVNLHQCKRGI   48

BAV3    FCPVKTYKLSLNASASEHSLHFEKSPSRFTLVNTHAGASVRVALHHQGAS  127
        :: ::  :..  . .. : : .     :  ::       . .. :   .
Ad5     FCLVKQAKVTYDSNTTGHRLSYKLPTKRQKLVVMVGEKPITITQHSVETE   98

BAV3    GSIRCSCSHAECLPVLLKTLCAFNFLD       154
        : :   :   : :  :.::::    :
Ad5     GCIHSPCQGPEDLCTLIKTLCGLKDLIPFN    128
```

FIG. 8B

```
BAV3    - MKRSVPQD--FNLVYPYKAKR-----PNIMPPFFDRNGFVENQEATLAML -43
          :::. : .  :: :::: .       : . :::   ::: :     :..
Ad2     - MKRARPSEDTFNPVYPYDTETGPPTVPFLTPPFVSPNGFQESPPGVLSLR -50

BAV3    - VEKPLTFDKE-GALTLGVGRGIRINPAGLLETNDLASAVFPPLASDEAGN -92
          :  ::  :   : :.: .: :. .  :: :  .. ...
Ad2     - VSEPL--DTSHGMLALKMGSGLTLDKAGNLTSQNVTTV------------ -86

BAV3    - VTLNMSDGLYTKDNKLAVKVGPGLSLDSNNALQVHTGDGLTVTDDKVSLN -142
               .  :      ...     :.. .  :: : :   : ::   .:..
Ad2     - -----TQPLKKTKSNISLDTSAPLTI-TSGALTVATTAPLIVTSGALSVQ -130

BAV3    - TQAPLSTTSAGLSLLLGPSLHLGEEERLTVNTGAGLQISNNALAVKVGSG -192
          .::::.                  . .:.. :   . .:   ::.   .
Ad2     - SQAPLT----------------VQDSKLSIATKGPITVSDGKLALQTSAP -164

BAV3    - ITVDAQNQLAASLGDGLESRDNKTVVKAGPGLTITNQALTVATGNGLQVN -242
          ..      :. .                       .  :: :::  : .:
Ad2     - LSGSDSDTLTVT----------------------ASPPLTTATGS-LGIN -191

BAV3    - PEGQLQLNITAGQGLNFANNSLAVELGSGLHFPPGQNQVSLYPGDGIDIR -292
           :  . .:          :  . . .   :
Ad2     - MEDPIYVN----------NGKIGIKISGPLQVAQ---------------- -215

BAV3    - DNRVTVPAGPGLRMLNHQLAVASGDGLEVHSDTLRLKLSHGLTFENGAVR -342
                                        :::: .    :.: :. ..:
Ad2     - -----------------------------NSDTLTVVTGPGVTVEQNSLR -236
```

FIG. 8C-I

```
BAV3   - AKLGPGLGTDDSGRSVVRTGRGLRVANGQVQIFSGRGTAIGTDSSLTLNI -392
         .:.   .: : :    ..:: :.:. :    .         . . : : .
Ad2    - TKVAGAIGYDSSNNMEIKTGGGMRINNNL--LILDVDYPFDAQTKLRLKL -284

BAV3   - RAPLQFSGPALTASLQGSGPITYNSNNGTFGLSIGPGMWVDQNRLQVNPG -442
                         : ::.  :.                   : .:
Ad2    - ----------------GQGPLYINASHN----------------LDINYN -302

BAV3   - AGLVFQGNNLVPNLADPLAISDSKISLSLGPGLTQASNALTLSLGNGLEF -492
          ::                   :  .  :   .  .:         :: :
Ad2    - RGLYL--------------FNASNNTKKLEVSIKKSS---------GLNF -329

BAV3   - SNQAVAIKAGRGLRFESSSQALESSLTVGNGLTLTDTVIRPNLGDGLEVR -542
          : .:: ::.:: :.. .
Ad2    - DNTAIAINAGKGLEFDTNT------------------------------- -348

BAV3   - DNKIIVKLGANLRFENGAVTAGTVNPSAPEAPPTLTAEPPLRASNSHLQL -592

Ad2    - -------------------------------------------------- -348

BAV3   - SLSEGLVVHNNALALQLGDGMEVNQHGLTLRVGSGLQMRDGILTVTPSGT -642
                           .  ..:   .  ..:::.            :.
Ad2    - -----------------SESPDIN--PIKTKIGSGID-------YNENGA -372

BAV3   - PIEPRLTAPLTQTENGIGLALGAGLELDESALQVKVGPGMRLNPVEKYVT -692
          :                  :::::  : :
Ad2    - MIT----------------KLGAGLSFDNSG------------------- -387
```

FIG. 8C-2

```
BAV3   - LLLGPGLSFGQPANRTNYDVRVSVEPPMVFGQRGQLTFLVGHGLHIQNSK -742
               .. :        : ....                        :.
Ad2    - -----AITIG-----NKNDDKLTLWTTPDPSP---------------NCR -412

BAV3   - LQLNLGQGLRTDPVTNQLEVPLGQGLEIADESQVRVKLGDGLQFDSQARI -792
         .                             .    . :        ::
Ad2    - IHSD------------------------NDCKFTLVLT---KCGSQVLA -434

BAV3   - TTAPNMVTETLWTGTGSNANVTWRGYTAPGSKLFLSLTRFSTGLVLGNMT -842
         : :    :.  : .::. : :.          .::        :... :.
Ad2    - TVAALAVSGDLSSMTGTVASVS----------IFLRFDQ--NGVLMENSS -472

BAV3   - IDSNASFGQYINAGHEQIECFILLDNQGNLKEGSNLQGTWEVKNNPSASK -892
         .                            : . :           :: .
Ad2    - LKKHY---------------------WNFRNGNS------TNANPYTNA -494

BAV3   - AAFLPSTALYPILNESRGSLPGKNLVGMQAILGGGGTCTVIA-TLNGRRS -941
            :.:    ::    .       :.:    . :      ... ::::
Ad2    - VGFMPNLLAYP---KTQSQTAKNNIVSQVYLHGDKTKPMILTITLNGTSE -541

BAV3   - NNYPAGQSII---FVWQ-EFNTIARQPLNHSTLTFSYWT -976
             .  :     : :  :    .       . :::: .
Ad2    - STETSEVSTYSMSFTWSWESGKYTTETFATNSYTFSYIAQE -582
```

FIG. 8C-3

SEQUENCE LISTING

```
<160> NUMBER OF SEQ ID NOS: 34

<210> SEQ ID NO 1
<211> LENGTH: 4060
<212> TYPE: DNA
<213> ORGANISM: Bovine adenovirus type 3
<220> FEATURE:
<221> NAME/KEY: CDS
<222> LOCATION: join (606..1215, 1323..1345)

<400> SEQUENCE: 1

catcatcaat aatctacagt acactgatgg cagcggtcca actgccaatc atttttgcca     60

cgtcatttat gacgcaacga cggcgagcgt ggcgtgctga cgtaactgtg ggcggagcg     120

cgtcgcggag gcggcggcgc tgggcggggc tgagggcggc gggggcggcg cgcggggcgg    180

cgcgcggggc ggggcgaggg gcggagttcc gcacccgcta cgtcattttc agacattttt    240

tagcaaattt gcgccttttg caagcatttt tctcacattt caggtattta gagggcggat    300

ttttggtgtt cgtacttccg tgtcacatag ttcactgtca atcttcatta cggcttagac    360
```

-continued

```
aaattttcgg cgtcttttcc gggtttatgt ccccggtcac ctttatgact gtgtgaaaca    420

cacctgccca ttgtttaccc ttggtcagtt ttttcgtctc ctagggtggg aacatcaaga    480

acaaatttgc cgagtaattg tgcacctttt tccgcgttag gactgcgttt cacacgtaga    540

cagacttttt ctcattttct cacactccgt cgtccgcttc agagctctgc gtcttcgctg    600

ccacc atg aag tac ctg gtc ctc gtt ctc aac gac ggc atg agt cga att    650
      Met Lys Tyr Leu Val Leu Val Leu Asn Asp Gly Met Ser Arg Ile
        1               5                  10                  15

gaa aaa gct ctc ctg tgc agc gat ggt gag gtg gat tta gag tgt cat      698
Glu Lys Ala Leu Leu Cys Ser Asp Gly Glu Val Asp Leu Glu Cys His
                20                  25                  30

gag gta ctt ccc cct tct ccc gcg cct gtc ccc gct tct gtg tca ccc      746
Glu Val Leu Pro Pro Ser Pro Ala Pro Val Pro Ala Ser Val Ser Pro
            35                  40                  45

gtg agg agt cct cct cct ctg tct ccg gtg ttt cct ccg tct ccg cca      794
Val Arg Ser Pro Pro Pro Leu Ser Pro Val Phe Pro Pro Ser Pro Pro
        50                  55                  60

gcc ccg ctt gtg aat cca gag gcg agt tcg ctg ctg cag cag tat cgg      842
Ala Pro Leu Val Asn Pro Glu Ala Ser Ser Leu Leu Gln Gln Tyr Arg
    65                  70                  75

aga gag ctg tta gag agg agc ctg ctc cga acg gcc gaa ggt cag cag      890
Arg Glu Leu Leu Glu Arg Ser Leu Leu Arg Thr Ala Glu Gly Gln Gln
 80                  85                  90                  95

cgt gca gtg tgt cca tgt gag cgg ttg ccc gtg gaa gag gat gag tgt      938
Arg Ala Val Cys Pro Cys Glu Arg Leu Pro Val Glu Glu Asp Glu Cys
                100                 105                 110

ctg aat gcc gta aat ttg ctg ttt cct gat ccc tgg cta aat gca gct      986
Leu Asn Ala Val Asn Leu Leu Phe Pro Asp Pro Trp Leu Asn Ala Ala
            115                 120                 125

gaa aat ggg ggt gat att ttt aag tct ccg gct atg tct cca gaa ccg     1034
Glu Asn Gly Gly Asp Ile Phe Lys Ser Pro Ala Met Ser Pro Glu Pro
        130                 135                 140

tgg ata gat ttg tct agc tac gat agc gat gta gaa gag gtg act agt     1082
Trp Ile Asp Leu Ser Ser Tyr Asp Ser Asp Val Glu Glu Val Thr Ser
    145                 150                 155

cac ttt ttt ctg gat tgc cct gaa gac ccc agt cgg gag tgt tca tct     1130
His Phe Phe Leu Asp Cys Pro Glu Asp Pro Ser Arg Glu Cys Ser Ser
160                 165                 170                 175

tgt ggg ttt cat cag gct caa agc gga att cca ggc att atg tgc agt     1178
Cys Gly Phe His Gln Ala Gln Ser Gly Ile Pro Gly Ile Met Cys Ser
                180                 185                 190

ttg tgc tac atg cgc caa acc tac cat tgc atc tat agtaagtaca          1224
Leu Cys Tyr Met Arg Gln Thr Tyr His Cys Ile Tyr
            195                 200

ttctgtaaaa gaacatcttg gtgatttcta ggtattgttt agggattaac tgggtggagt   1284

gatcttaatc cggcataacc aaatacatgt tttcacag  gt cca gtt tct gaa gag   1339
                                          Ser Pro Val Ser Glu Glu
                                                  205

gaa atg tgagtcatgt tgactttggc gcgcaagagg aaatgtgagt catgttgact      1395
Glu Met
210

ttggcgcgcc ctacggtgac tttaaagcaa tttgaggatc actttttgt tagtcgctat    1455

aaagtagtca cggagtcttc atggatcact taagcgttct tttggatttg aagctgcttc   1515

gctctatcgt agcgggggct tcaaatcgca ctggagtgtg gaagaggcgg ctgtggctgg   1575

gacgcctgac tcaactggtc catgatacct gcgtagagaa cgagagcata tttctcaatt   1635
```

-continued

```
ctctgccagg gaatgaagct tttttaaggt tgcttcggag cggctatttt gaagtgtttg   1695
acgtgtttgt ggtgcctgag ctgcatctgg acactccggg tcgagtggtc gccgctcttg   1755
ctctgctggt gttcatcctc aacgatttag acgctaattc tgcttcttca ggctttgatt   1815
caggttttct cgtggaccgt ctctgcgtgc cgctatggct gaaggccagg gcgttcaaga   1875
tcacccagag ctccaggagc acttcgcagc cttcctcgtc gcccgacaag acgacccaga   1935
ctaccagcca gtagacgggg acagcccacc ccgggctagc ctggaggagg ctgaacagag   1995
cagcactcgt ttcgagcaca tcagttaccg agacgtggtg gatgacttca atagatgcca   2055
tgatgttttt tatgagaggt acagttttga ggacataaag agctacgagg ctttgcctga   2115
ggacaatttg gagcagctca tagctatgca tgctaaaatc aagctgctgc ccggtcggga   2175
gtatgagttg actcaacctt tgaacataac atcttgcgcc tatgtgctcg gaaatggggc   2235
tactattagg gtaacagggg aagcctcccc ggctattaga gtgggggcca tggccgtggg   2295
tccgtgtgta acaggaatga ctggggtgac ttttgtgaat tgtaggtttg agagagagtc   2355
aacaattagg gggtccctga tacgagcttc aactcacgtg ctgtttcatg gctgttattt   2415
tatgggaatt atgggcactt gtattgaggt gggggcggga gcttacattc ggggttgtga   2475
gtttgtgggc tgttaccggg gaatctgttc tacttctaac agagatatta aggtgaggca   2535
gtgcaacttt gacaaatgct tactgggtat tacttgtaag gggactatc gtctttcggg    2595
aaatgtgtgt tctgagactt tctgctttgc tcatttagag ggagagggtt tggttaaaaa   2655
caacacagtc aagtccccta gtcgctggac cagcgagtct ggcttttcca tgataacttg   2715
tgcagacggc agggttacgc ctttgggttc cctccacatt gtgggcaacc gttgtaggcg   2775
ttggccaacc atgcagggga atgtgtttat catgtctaaa ctgtatctgg gcaacagaat   2835
agggactgta gccctgcccc agtgtgcttt ctacaagtcc agcatttgtt tggaggagag   2895
ggcgacaaac aagctggtct tggcttgtgc ttttgagaat aatgtactgg tgtacaaagt   2955
gctgagacgg gagagtccct caaccgtgaa aatgtgtgtt tgtgggactt ctcattatgc   3015
aaagcctttg acactggcaa ttatttcttc agatattcgg gctaatcgat acatgtacac   3075
tgtggactca acagagttca cttctgacga ggattaaaag tgggcggggc caagaggggt   3135
ataaataggt ggggaggttg aggggagccg tagtttctgt tttcccaga ctgggggga     3195
caacatggcc gaggaagggc gcatttatgt gccttatgta actgcccgcc tgcccaagtg   3255
gtcgggttcg gtgcaggata agacgggctc gaacatgttg gggggtgtgg tactccctcc   3315
taattcacag gcgcaccgga cggagaccgt gggcactgag gccaccagag acaacctgca   3375
cgccgaggga gcgcgtcgtc ctgaggatca gacgccctac atgatcttgg tggaggactc   3435
tctgggaggt ttgaagaggc gaatggactt gctggaagaa tctaatcagc agctgctggc   3495
aactctcaac cgtctccgta caggactcgc tgcctatgtg caggctaacc ttgtgggcgg   3555
ccaagttaac cccttttgttt aaataaaaat acactcatac agtttattat gctgtcaata  3615
aaattcttta tttttcctgt gataataccg tgtccagcgt gctctgtcaa taagggtcct   3675
atgcatcctg agaagggcct catataccca tggcatgaat attaagatac atgggcataa   3735
ggccctcaga agggttgagg tagagccact gcagactttc gtggggaggt aaggtgttgt   3795
aaataatcca gtcatactga ctgtgctggg cgtggaagga aaagatgtct tttagaagaa   3855
gggtgattgg caaagggagg ctcttagtgt aggtattgat aaatctgttc agttgggagg   3915
gatgcattcg gggctaata aggtggagtt tagcctgaat cttaaggttg gcaatgttgc    3975
```

-continued

```
cccctaggtc tttgcgagga ttcatgttgt gcagtaccac aaaaacagag tagcctgtgc   4035

atttggggaa tttatcatga agctt                                         4060


<210> SEQ ID NO 2
<211> LENGTH: 211
<212> TYPE: PRT
<213> ORGANISM: Bovine adenovirus type 3

<400> SEQUENCE: 2

Met Lys Tyr Leu Val Leu Val Leu Asn Asp Gly Met Ser Arg Ile Glu
  1               5                  10                  15

Lys Ala Leu Leu Cys Ser Asp Gly Glu Val Asp Leu Glu Cys His Glu
             20                  25                  30

Val Leu Pro Pro Ser Pro Ala Pro Val Pro Ala Ser Val Ser Pro Val
         35                  40                  45

Arg Ser Pro Pro Pro Leu Ser Pro Val Phe Pro Pro Ser Pro Pro Ala
     50                  55                  60

Pro Leu Val Asn Pro Glu Ala Ser Ser Leu Leu Gln Gln Tyr Arg Arg
 65                  70                  75                  80

Glu Leu Leu Glu Arg Ser Leu Leu Arg Thr Ala Glu Gly Gln Gln Arg
                 85                  90                  95

Ala Val Cys Pro Cys Glu Arg Leu Pro Val Glu Glu Asp Glu Cys Leu
            100                 105                 110

Asn Ala Val Asn Leu Leu Phe Pro Asp Pro Trp Leu Asn Ala Ala Glu
        115                 120                 125

Asn Gly Gly Asp Ile Phe Lys Ser Pro Ala Met Ser Pro Glu Pro Trp
    130                 135                 140

Ile Asp Leu Ser Ser Tyr Asp Ser Asp Val Glu Glu Val Thr Ser His
145                 150                 155                 160

Phe Phe Leu Asp Cys Pro Glu Asp Pro Ser Arg Glu Cys Ser Ser Cys
                165                 170                 175

Gly Phe His Gln Ala Gln Ser Gly Ile Pro Gly Ile Met Cys Ser Leu
            180                 185                 190

Cys Tyr Met Arg Gln Thr Tyr His Cys Ile Tyr Ser Pro Val Ser Glu
        195                 200                 205

Glu Glu Met
    210


<210> SEQ ID NO 3
<211> LENGTH: 4060
<212> TYPE: DNA
<213> ORGANISM: Bovine adenovirus type 3
<220> FEATURE:
<221> NAME/KEY: CDS
<222> LOCATION: (1476)..(1946)

<400> SEQUENCE: 3

catcatcaat aatctacagt acactgatgg cagcggtcca actgccaatc atttttgcca     60

cgtcatttat gacgcaacga cggcgagcgt ggcgtgctga cgtaactgtg ggcggagcg    120

cgtcgcggag gcggcggcgc tgggcggggc tgagggcggc gggggcggcg cgcggggcgg    180

cgcgcggggc ggggcgaggg gcggagttcc gcacccgcta cgtcattttc agacattttt    240

tagcaaattt gcgccttttg caagcatttt tctcacattt caggtattta gagggcggat    300

ttttggtgtt cgtacttccg tgtcacatag ttcactgtca atcttcatta cggcttagac    360

aaattttcgg cgtcttttcc gggtttatgt ccccggtcac ctttatgact gtgtgaaaca    420
```

-continued

```
cacctgccca ttgtttaccc ttggtcagtt ttttcgtctc ctagggtggg aacatcaaga    480

acaaatttgc cgagtaattg tgcacctttt tccgcgttag gactgcgttt cacacgtaga    540

cagacttttt ctcattttct cacactccgt cgtccgcttc agagctctgc gtcttcgctg    600

ccaccatgaa gtacctggtc ctcgttctca acgacggcat gagtcgaatt gaaaaagctc    660

tcctgtgcag cgatggtgag gtggatttag agtgtcatga ggtacttccc ccttctcccg    720

cgcctgtccc cgcttctgtg tcacccgtga ggagtcctcc tcctctgtct ccggtgtttc    780

ctccgtctcc gccagccccg cttgtgaatc cagaggcgag ttcgctgctg cagcagtatc    840

ggagagagct gttagagagg agcctgctcc gaacggccga aggtcagcag cgtgcagtgt    900

gtccatgtga gcggttgccc gtggaagagg atgagtgtct gaatgccgta aatttgctgt    960

ttcctgatcc ctggctaaat gcagctgaaa atgggggtga tatttttaag tctccggcta   1020

tgtctccaga accgtggata gatttgtcta gctacgatag cgatgtagaa gaggtgacta   1080

gtcacttttt tctggattgc cctgaagacc ccagtcggga gtgttcatct tgtgggtttc   1140

atcaggctca aagcggaatt ccaggcatta tgtgcagttt gtgctacatg cgccaaacct   1200

accattgcat ctatagtaag tacattctgt aaaagaacat cttggtgatt tctaggtatt   1260

gtttagggat taactgggtg gagtgatctt aatccggcat aaccaaatac atgttttcac   1320

aggtccagtt tctgaagagg aaatgtgagt catgttgact ttggcgcgca agaggaaatg   1380

tgagtcatgt tgactttggc gcgccctacg gtgactttaa agcaatttga ggatcacttt   1440

tttgttagtc gctataaagt agtcacggag tcttc atg gat cac tta agc gtt      1493
                                       Met Asp His Leu Ser Val
                                         1               5

ctt ttg gat ttg aag ctg ctt cgc tct atc gta gcg ggg gct tca aat     1541
Leu Leu Asp Leu Lys Leu Leu Arg Ser Ile Val Ala Gly Ala Ser Asn
             10                  15                  20

cgc act gga gtg tgg aag agg cgg ctg tgg ctg gga cgc ctg act caa     1589
Arg Thr Gly Val Trp Lys Arg Arg Leu Trp Leu Gly Arg Leu Thr Gln
         25                  30                  35

ctg gtc cat gat acc tgc gta gag aac gag agc ata ttt ctc aat tct     1637
Leu Val His Asp Thr Cys Val Glu Asn Glu Ser Ile Phe Leu Asn Ser
     40                  45                  50

ctg cca ggg aat gaa gct ttt tta agg ttg ctt cgg agc ggc tat ttt     1685
Leu Pro Gly Asn Glu Ala Phe Leu Arg Leu Leu Arg Ser Gly Tyr Phe
 55                  60                  65                  70

gaa gtg ttt gac gtg ttt gtg gtg cct gag ctg cat ctg gac act ccg     1733
Glu Val Phe Asp Val Phe Val Val Pro Glu Leu His Leu Asp Thr Pro
                 75                  80                  85

ggt cga gtg gtc gcc gct ctt gct ctg ctg gtg ttc atc ctc aac gat     1781
Gly Arg Val Val Ala Ala Leu Ala Leu Leu Val Phe Ile Leu Asn Asp
             90                  95                 100

tta gac gct aat tct gct tct tca ggc ttt gat tca ggt ttt ctc gtg     1829
Leu Asp Ala Asn Ser Ala Ser Ser Gly Phe Asp Ser Gly Phe Leu Val
        105                 110                 115

gac cgt ctc tgc gtg ccg cta tgg ctg aag gcc agg gcg ttc aag atc     1877
Asp Arg Leu Cys Val Pro Leu Trp Leu Lys Ala Arg Ala Phe Lys Ile
    120                 125                 130

acc cag agc tcc agg agc act tcg cag cct tcc tcg tcg ccc gac aag     1925
Thr Gln Ser Ser Arg Ser Thr Ser Gln Pro Ser Ser Ser Pro Asp Lys
135                 140                 145                 150

acg acc cag act acc agc cag tagacgggga cagcccaccc cgggctagcc        1976
Thr Thr Gln Thr Thr Ser Gln
                155
```

-continued

```
tggaggaggc tgaacagagc agcactcgtt tcgagcacat cagttaccga gacgtggtgg   2036

atgacttcaa tagatgccat gatgtttttt atgagaggta cagttttgag gacataaaga   2096

gctacgaggc tttgcctgag gacaatttgg agcagctcat agctatgcat gctaaaatca   2156

agctgctgcc cggtcgggag tatgagttga ctcaaccttt gaacataaca tcttgcgcct   2216

atgtgctcgg aaatggggct actattaggg taacagggga agcctccccg gctattagag   2276

tgggggccat ggccgtgggt ccgtgtgtaa caggaatgac tggggtgact tttgtgaatt   2336

gtaggtttga gagagagtca acaattaggg ggtccctgat acgagcttca actcacgtgc   2396

tgtttcatgg ctgttatttt atgggaatta tgggcacttg tattgaggtg gggggcgggag  2456

cttacattcg gggttgtgag tttgtgggct gttaccgggg aatctgttct acttctaaca   2516

gagatattaa ggtgaggcag tgcaactttg acaaatgctt actgggtatt acttgtaagg   2576

gggactatcg tctttcggga aatgtgtgtt ctgagacttt ctgctttgct catttagagg   2636

gagagggttt ggttaaaaac aacacagtca agtcccctag tcgctggacc agcgagtctg   2696

gcttttccat gataacttgt gcagacggca gggttacgcc tttgggttcc ctccacattg   2756

tgggcaaccg ttgtaggcgt tggccaacca tgcaggggaa tgtgtttatc atgtctaaac   2816

tgtatctggg caacagaata gggactgtag ccctgcccca gtgtgctttc tacaagtcca   2876

gcatttgttt ggaggagagg gcgacaaaca agctggtctt ggcttgtgct tttgagaata   2936

atgtactggt gtacaaagtg ctgagacggg agagtccctc aaccgtgaaa atgtgtgttt   2996

gtgggacttc tcattatgca aagcctttga cactggcaat tatttcttca gatattcggg   3056

ctaatcgata catgtacact gtggactcaa cagagttcac ttctgacgag gattaaaagt   3116

gggcggggcc aagaggggta taaataggtg gggaggttga ggggagccgt agtttctgtt   3176

tttcccagac tgggggggac aacatggccg aggaagggcg catttatgtg ccttatgtaa   3236

ctgcccgcct gcccaagtgg tcgggttcgg tgcaggataa gacgggctcg aacatgttgg   3296

ggggtgtggt actccctcct aattcacagg cgcaccggac ggagaccgtg ggcactgagg   3356

ccaccagaga caacctgcac gccgagggag cgcgtcgtcc tgaggatcag acgccctaca   3416

tgatcttggt ggaggactct ctgggaggtt tgaagaggcg aatggacttg ctggaagaat   3476

ctaatcagca gctgctggca actctcaacc gtctccgtac aggactcgct gcctatgtgc   3536

aggctaacct tgtgggcggc caagttaacc cctttgttta aataaaaata cactcataca   3596

gtttattatg ctgtcaataa aattctttat ttttcctgtg ataataccgt gtccagcgtg   3656

ctctgtcaat aagggtccta tgcatcctga gaagggcctc atatacccat ggcatgaata   3716

ttaagataca tgggcataag gccctcagaa gggttgaggt agagccactg cagactttcg   3776

tggggaggta aggtgttgta aataatccag tcatactgac tgtgctgggc gtggaaggaa   3836

aagatgtctt ttagaagaag ggtgattggc aaagggaggc tcttagtgta ggtattgata   3896

aatctgttca gttgggaggg atgcattcgg gggctaataa ggtggagttt agcctgaatc   3956

ttaaggttgg caatgttgcc ccctaggtct ttgcgaggat tcatgttgtg cagtaccaca   4016

aaaacagagt agcctgtgca tttggggaat ttatcatgaa gctt                    4060
```

<210> SEQ ID NO 4
<211> LENGTH: 157
<212> TYPE: PRT
<213> ORGANISM: Bovine adenovirus type 3

<400> SEQUENCE: 4

-continued

```
Met Asp His Leu Ser Val Leu Leu Asp Leu Lys Leu Leu Arg Ser Ile
  1               5                  10                  15

Val Ala Gly Ala Ser Asn Arg Thr Gly Val Trp Lys Arg Arg Leu Trp
             20                  25                  30

Leu Gly Arg Leu Thr Gln Leu Val His Asp Thr Cys Val Glu Asn Glu
         35                  40                  45

Ser Ile Phe Leu Asn Ser Leu Pro Gly Asn Glu Ala Phe Leu Arg Leu
     50                  55                  60

Leu Arg Ser Gly Tyr Phe Glu Val Phe Asp Val Phe Val Val Pro Glu
 65                  70                  75                  80

Leu His Leu Asp Thr Pro Gly Arg Val Val Ala Ala Leu Ala Leu Leu
                 85                  90                  95

Val Phe Ile Leu Asn Asp Leu Asp Ala Asn Ser Ala Ser Ser Gly Phe
            100                 105                 110

Asp Ser Gly Phe Leu Val Asp Arg Leu Cys Val Pro Leu Trp Leu Lys
        115                 120                 125

Ala Arg Ala Phe Lys Ile Thr Gln Ser Ser Arg Ser Thr Ser Gln Pro
    130                 135                 140

Ser Ser Ser Pro Asp Lys Thr Thr Gln Thr Thr Ser Gln
145                 150                 155
```

<210> SEQ ID NO 5
<211> LENGTH: 4060
<212> TYPE: DNA
<213> ORGANISM: Bovine adenovirus type 3
<220> FEATURE:
<221> NAME/KEY: CDS
<222> LOCATION: (1850)..(3109)

<400> SEQUENCE: 5

```
catcatcaat aatctacagt acactgatgg cagcggtcca actgccaatc atttttgcca     60

cgtcatttat gacgcaacga cggcgagcgt ggcgtgctga cgtaactgtg gggcggagcg    120

cgtcgcggag gcggcggcgc tgggcggggc tgagggcggc gggggcggcg cgcggggcgg    180

cgcgcggggc ggggcgaggg gcggagttcc gcacccgcta cgtcattttc agacattttt    240

tagcaaattt gcgccttttg caagcatttt tctcacattt caggtattta gagggcggat    300

ttttggtgtt cgtacttccg tgtcacatag ttcactgtca atcttcatta cggcttagac    360

aaattttcgg cgtcttttcc gggtttatgt ccccggtcac ctttatgact gtgtgaaaca    420

cacctgccca ttgtttaccc ttggtcagtt ttttcgtctc ctagggtggg aacatcaaga    480

acaaatttgc cgagtaattg tgcacctttt tccgcgttag gactgcgttt cacacgtaga    540

cagacttttt ctcattttct cacactccgt cgtccgcttc agagctctgc gtcttcgctg    600

ccaccatgaa gtacctggtc ctcgttctca acgacggcat gagtcgaatt gaaaaagctc    660

tcctgtgcag cgatggtgag gtggatttag agtgtcatga ggtacttccc ccttctcccg    720

cgcctgtccc cgcttctgtg tcacccgtga ggagtcctcc tcctctgtct ccggtgtttc    780

ctccgtctcc gccagccccg cttgtgaatc cagaggcgag ttcgctgctg cagcagtatc    840

ggagagagct gttagagagg agcctgctcc gaacggccga aggtcagcag cgtgcagtgt    900

gtccatgtga gcggttgccc gtggaagagg atgagtgtct gaatgccgta aatttgctgt    960

ttcctgatcc ctggctaaat gcagctgaaa atgggggtga tatttttaag tctccggcta   1020

tgtctccaga accgtggata gatttgtcta gctacgatag cgatgtagaa gaggtgacta   1080

gtcacttttt tctggattgc cctgaagacc ccagtcggga gtgttcatct tgtgggtttc   1140
```

-continued

```
atcaggctca aagcggaatt ccaggcatta tgtgcagttt gtgctacatg cgccaaacct   1200

accattgcat ctatagtaag tacattctgt aaaagaacat cttggtgatt tctaggtatt   1260

gtttagggat taactgggtg gagtgatctt aatccggcat aaccaaatac atgttttcac   1320

aggtccagtt tctgaagagg aaatgtgagt catgttgact ttggcgcgca agaggaaatg   1380

tgagtcatgt tgactttggc gcgccctacg gtgactttaa agcaatttga ggatcacttt   1440

tttgttagtc gctataaagt agtcacggag tcttcatgga tcacttaagc gttcttttgg   1500

atttgaagct gcttcgctct atcgtagcgg gggcttcaaa tcgcactgga gtgtggaaga   1560

ggcggctgtg gctgggacgc ctgactcaac tggtccatga tacctgcgta gagaacgaga   1620

gcatatttct caattctctg ccagggaatg aagctttttt aaggttgctt cggagcggct   1680

attttgaagt gtttgacgtg tttgtggtgc ctgagctgca tctggacact ccgggtcgag   1740

tggtcgccgc tcttgctctg ctggtgttca tcctcaacga tttagacgct aattctgctt   1800

cttcaggctt tgattcaggt tttctcgtgg accgtctctg cgtgccgct atg gct gaa   1858
                                                      Met Ala Glu
                                                        1

ggc cag ggc gtt caa gat cac cca gag ctc cag gag cac ttc gca gcc      1906
Gly Gln Gly Val Gln Asp His Pro Glu Leu Gln Glu His Phe Ala Ala
      5                   10                  15

ttc ctc gtc gcc cga caa gac gac cca gac tac cag cca gta gac ggg      1954
Phe Leu Val Ala Arg Gln Asp Asp Pro Asp Tyr Gln Pro Val Asp Gly
 20                  25                  30                  35

gac agc cca ccc cgg gct agc ctg gag gag gct gaa cag agc agc act      2002
Asp Ser Pro Pro Arg Ala Ser Leu Glu Glu Ala Glu Gln Ser Ser Thr
                 40                  45                  50

cgt ttc gag cac atc agt tac cga gac gtg gtg gat gac ttc aat aga      2050
Arg Phe Glu His Ile Ser Tyr Arg Asp Val Val Asp Asp Phe Asn Arg
             55                  60                  65

tgc cat gat gtt ttt tat gag agg tac agt ttt gag gac ata aag agc      2098
Cys His Asp Val Phe Tyr Glu Arg Tyr Ser Phe Glu Asp Ile Lys Ser
         70                  75                  80

tac gag gct ttg cct gag gac aat ttg gag cag ctc ata gct atg cat      2146
Tyr Glu Ala Leu Pro Glu Asp Asn Leu Glu Gln Leu Ile Ala Met His
     85                  90                  95

gct aaa atc aag ctg ctg ccc ggt cgg gag tat gag ttg act caa cct      2194
Ala Lys Ile Lys Leu Leu Pro Gly Arg Glu Tyr Glu Leu Thr Gln Pro
100                 105                 110                 115

ttg aac ata aca tct tgc gcc tat gtg ctc gga aat ggg gct act att      2242
Leu Asn Ile Thr Ser Cys Ala Tyr Val Leu Gly Asn Gly Ala Thr Ile
                120                 125                 130

agg gta aca ggg gaa gcc tcc ccg gct att aga gtg ggg gcc atg gcc      2290
Arg Val Thr Gly Glu Ala Ser Pro Ala Ile Arg Val Gly Ala Met Ala
            135                 140                 145

gtg ggt ccg tgt gta aca gga atg act ggg gtg act ttt gtg aat tgt      2338
Val Gly Pro Cys Val Thr Gly Met Thr Gly Val Thr Phe Val Asn Cys
        150                 155                 160

agg ttt gag aga gag tca aca att agg ggg tcc ctg ata cga gct tca      2386
Arg Phe Glu Arg Glu Ser Thr Ile Arg Gly Ser Leu Ile Arg Ala Ser
    165                 170                 175

act cac gtg ctg ttt cat ggc tgt tat ttt atg gga att atg ggc act      2434
Thr His Val Leu Phe His Gly Cys Tyr Phe Met Gly Ile Met Gly Thr
180                 185                 190                 195

tgt att gag gtg ggg gcg gga gct tac att cgg ggt tgt gag ttt gtg      2482
Cys Ile Glu Val Gly Ala Gly Ala Tyr Ile Arg Gly Cys Glu Phe Val
                200                 205                 210
```

-continued

```
ggc tgt tac cgg gga atc tgt tct act tct aac aga gat att aag gtg     2530
Gly Cys Tyr Arg Gly Ile Cys Ser Thr Ser Asn Arg Asp Ile Lys Val
            215                 220                 225

agg cag tgc aac ttt gac aaa tgc tta ctg ggt att act tgt aag ggg     2578
Arg Gln Cys Asn Phe Asp Lys Cys Leu Leu Gly Ile Thr Cys Lys Gly
        230                 235                 240

gac tat cgt ctt tcg gga aat gtg tgt tct gag act ttc tgc ttt gct     2626
Asp Tyr Arg Leu Ser Gly Asn Val Cys Ser Glu Thr Phe Cys Phe Ala
    245                 250                 255

cat tta gag gga gag ggt ttg gtt aaa aac aac aca gtc aag tcc cct     2674
His Leu Glu Gly Glu Gly Leu Val Lys Asn Asn Thr Val Lys Ser Pro
260                 265                 270                 275

agt cgc tgg acc agc gag tct ggc ttt tcc atg ata act tgt gca gac     2722
Ser Arg Trp Thr Ser Glu Ser Gly Phe Ser Met Ile Thr Cys Ala Asp
                280                 285                 290

ggc agg gtt acg cct ttg ggt tcc ctc cac att gtg ggc aac cgt tgt     2770
Gly Arg Val Thr Pro Leu Gly Ser Leu His Ile Val Gly Asn Arg Cys
            295                 300                 305

agg cgt tgg cca acc atg cag ggg aat gtg ttt atc atg tct aaa ctg     2818
Arg Arg Trp Pro Thr Met Gln Gly Asn Val Phe Ile Met Ser Lys Leu
        310                 315                 320

tat ctg ggc aac aga ata ggg act gta gcc ctg ccc cag tgt gct ttc     2866
Tyr Leu Gly Asn Arg Ile Gly Thr Val Ala Leu Pro Gln Cys Ala Phe
    325                 330                 335

tac aag tcc agc att tgt ttg gag gag agg gcg aca aac aag ctg gtc     2914
Tyr Lys Ser Ser Ile Cys Leu Glu Glu Arg Ala Thr Asn Lys Leu Val
340                 345                 350                 355

ttg gct tgt gct ttt gag aat aat gta ctg gtg tac aaa gtg ctg aga     2962
Leu Ala Cys Ala Phe Glu Asn Asn Val Leu Val Tyr Lys Val Leu Arg
                360                 365                 370

cgg gag agt ccc tca acc gtg aaa atg tgt gtt tgt ggg act tct cat     3010
Arg Glu Ser Pro Ser Thr Val Lys Met Cys Val Cys Gly Thr Ser His
            375                 380                 385

tat gca aag cct ttg aca ctg gca att att tct tca gat att cgg gct     3058
Tyr Ala Lys Pro Leu Thr Leu Ala Ile Ile Ser Ser Asp Ile Arg Ala
        390                 395                 400

aat cga tac atg tac act gtg gac tca aca gag ttc act tct gac gag     3106
Asn Arg Tyr Met Tyr Thr Val Asp Ser Thr Glu Phe Thr Ser Asp Glu
    405                 410                 415

gat taaaagtggg cggggccaag aggggtataa ataggtgggg aggttgaggg          3159
Asp
420

gagccgtagt ttctgttttt cccagactgg gggggacaac atggccgagg aagggcgcat   3219

ttatgtgcct tatgtaactg cccgcctgcc caagtggtcg ggttcggtgc aggataagac   3279

gggctcgaac atgttggggg gtgtggtact ccctcctaat tcacaggcgc accggacgga   3339

gaccgtgggc actgaggcca ccagagacaa cctgcacgcc gagggagcgc gtcgtcctga   3399

ggatcagacg ccctacatga tcttggtgga ggactctctg ggaggtttga agaggcgaat   3459

ggacttgctg gaagaatcta atcagcagct gctggcaact ctcaaccgtc tccgtacagg   3519

actcgctgcc tatgtgcagg ctaaccttgt gggcggccaa gttaacccct ttgtttaaat   3579

aaaaatacac tcatacagtt tattatgctg tcaataaaat tctttatttt tcctgtgata   3639

ataccgtgtc cagcgtgctc tgtcaataag ggtcctatgc atcctgagaa gggcctcata   3699

tacccatggc atgaatatta agatacatgg gcataaggcc ctcagaaggg ttgaggtaga   3759

gccactgcag actttcgtgg ggaggtaagg tgttgtaaat aatccagtca tactgactgt   3819

gctgggcgtg gaaggaaaag atgtctttta gaagaagggt gattggcaaa gggaggctct   3879
```

-continued

```
tagtgtaggt attgataaat ctgttcagtt gggagggatg cattcggggg ctaataaggt   3939

ggagtttagc ctgaatctta aggttggcaa tgttgccccc taggtctttg cgaggattca   3999

tgttgtgcag taccacaaaa acagagtagc ctgtgcattt ggggaattta tcatgaagct   4059

t                                                                   4060


<210> SEQ ID NO 6
<211> LENGTH: 420
<212> TYPE: PRT
<213> ORGANISM: Bovine adenovirus type 3

<400> SEQUENCE: 6

Met Ala Glu Gly Gln Gly Val Gln Asp His Pro Glu Leu Gln Glu His
  1               5                  10                  15

Phe Ala Ala Phe Leu Val Ala Arg Gln Asp Asp Pro Asp Tyr Gln Pro
             20                  25                  30

Val Asp Gly Asp Ser Pro Pro Arg Ala Ser Leu Glu Glu Ala Glu Gln
         35                  40                  45

Ser Ser Thr Arg Phe Glu His Ile Ser Tyr Arg Asp Val Val Asp Asp
     50                  55                  60

Phe Asn Arg Cys His Asp Val Phe Tyr Glu Arg Tyr Ser Phe Glu Asp
 65                  70                  75                  80

Ile Lys Ser Tyr Glu Ala Leu Pro Glu Asp Asn Leu Glu Gln Leu Ile
                 85                  90                  95

Ala Met His Ala Lys Ile Lys Leu Leu Pro Gly Arg Glu Tyr Glu Leu
            100                 105                 110

Thr Gln Pro Leu Asn Ile Thr Ser Cys Ala Tyr Val Leu Gly Asn Gly
        115                 120                 125

Ala Thr Ile Arg Val Thr Gly Glu Ala Ser Pro Ala Ile Arg Val Gly
    130                 135                 140

Ala Met Ala Val Gly Pro Cys Val Thr Gly Met Thr Gly Val Thr Phe
145                 150                 155                 160

Val Asn Cys Arg Phe Glu Arg Glu Ser Thr Ile Arg Gly Ser Leu Ile
                165                 170                 175

Arg Ala Ser Thr His Val Leu Phe His Gly Cys Tyr Phe Met Gly Ile
            180                 185                 190

Met Gly Thr Cys Ile Glu Val Gly Ala Gly Ala Tyr Ile Arg Gly Cys
        195                 200                 205

Glu Phe Val Gly Cys Tyr Arg Gly Ile Cys Ser Thr Ser Asn Arg Asp
    210                 215                 220

Ile Lys Val Arg Gln Cys Asn Phe Asp Lys Cys Leu Leu Gly Ile Thr
225                 230                 235                 240

Cys Lys Gly Asp Tyr Arg Leu Ser Gly Asn Val Cys Ser Glu Thr Phe
                245                 250                 255

Cys Phe Ala His Leu Glu Gly Glu Gly Leu Val Lys Asn Asn Thr Val
            260                 265                 270

Lys Ser Pro Ser Arg Trp Thr Ser Glu Ser Gly Phe Ser Met Ile Thr
        275                 280                 285

Cys Ala Asp Gly Arg Val Thr Pro Leu Gly Ser Leu His Ile Val Gly
    290                 295                 300

Asn Arg Cys Arg Arg Trp Pro Thr Met Gln Gly Asn Val Phe Ile Met
305                 310                 315                 320

Ser Lys Leu Tyr Leu Gly Asn Arg Ile Gly Thr Val Ala Leu Pro Gln
                325                 330                 335
```

-continued

Cys Ala Phe Tyr Lys Ser Ser Ile Cys Leu Glu Glu Arg Ala Thr Asn
340 345 350

Lys Leu Val Leu Ala Cys Ala Phe Glu Asn Asn Val Leu Val Tyr Lys
355 360 365

Val Leu Arg Arg Glu Ser Pro Ser Thr Val Lys Met Cys Val Cys Gly
370 375 380

Thr Ser His Tyr Ala Lys Pro Leu Thr Leu Ala Ile Ile Ser Ser Asp
385 390 395 400

Ile Arg Ala Asn Arg Tyr Met Tyr Thr Val Asp Ser Thr Glu Phe Thr
405 410 415

Ser Asp Glu Asp
420

<210> SEQ ID NO 7
<211> LENGTH: 4060
<212> TYPE: DNA
<213> ORGANISM: Bovine adenovirus type 3
<220> FEATURE:
<221> NAME/KEY: CDS
<222> LOCATION: (3200)..(3574)

<400> SEQUENCE: 7
catcatcaat aatctacagt acactgatgg cagcggtcca actgccaatc atttttgcca 60
cgtcatttat gacgcaacga cggcgagcgt ggcgtgctga cgtaactgtg ggcggagcg 120 cgtcgcggag gcggcggcgc tgggcggggc tgagggcggc gggggcggcg cgcggggcgg 180
cgcgcggggc ggggcgaggg gcggagttcc gcacccgcta cgtcattttc agacattttt 240
tagcaaattt gcgccttttg caagcatttt tctcacattt caggtattta gagggcggat 300
ttttggtgtt cgtacttccg tgtcacatag ttcactgtca atcttcatta cggcttagac 360
aaattttcgg cgtcttttcc gggtttatgt ccccggtcac ctttatgact gtgtgaaaca 420
cacctgccca ttgtttaccc ttggtcagtt ttttcgtctc ctagggtggg aacatcaaga 480
acaaatttgc cgagtaattg tgcacctttt tccgcgttag gactgcgttt cacacgtaga 540
cagacttttt ctcattttct cacactccgt cgtccgcttc agagctctgc gtcttcgctg 600
ccaccatgaa gtacctggtc ctcgttctca acgacggcat gagtcgaatt gaaaaagctc 660
tcctgtgcag cgatggtgag gtggatttag agtgtcatga ggtacttccc ccttctcccg 720
cgcctgtccc cgcttctgtg tcacccgtga ggagtcctcc tcctctgtct ccggtgtttc 780
ctccgtctcc gccagccccg cttgtgaatc cagaggcgag ttcgctgctg cagcagtatc 840
ggagagagct gttagagagg agcctgctcc gaacggccga aggtcagcag cgtgcagtgt 900
gtccatgtga gcggttgccc gtggaagagg atgagtgtct gaatgccgta aatttgctgt 960
ttcctgatcc ctggctaaat gcagctgaaa atgggggtga tatttttaag tctccggcta 1020
tgtctccaga accgtggata gatttgtcta gctacgatag cgatgtagaa gaggtgacta 1080
gtcacttttt tctggattgc cctgaagacc ccagtcggga gtgttcatct tgtgggtttc 1140
atcaggctca aagcggaatt ccaggcatta tgtgcagttt gtgctacatg cgccaaacct 1200
accattgcat ctatagtaag tacattctgt aaaagaacat cttggtgatt tctaggtatt 1260
gtttagggat taactgggtg gagtgatctt aatccggcat aaccaaatac atgttttcac 1320
aggtccagtt tctgaagagg aaatgtgagt catgttgact ttggcgcgca agaggaaatg 1380
tgagtcatgt tgactttggc gcgccctacg gtgactttaa agcaatttga ggatcacttt 1440
tttgttagtc gctataaagt agtcacggag tcttcatgga tcacttaagc gttcttttgg 1500

-continued

```
atttgaagct gcttcgctct atcgtagcgg gggcttcaaa tcgcactgga gtgtggaaga   1560

ggcggctgtg gctgggacgc ctgactcaac tggtccatga tacctgcgta gagaacgaga   1620

gcatatttct caattctctg ccagggaatg aagctttttt aaggttgctt cggagcggct   1680

attttgaagt gtttgacgtg tttgtggtgc ctgagctgca tctggacact ccgggtcgag   1740

tggtcgccgc tcttgctctg ctggtgttca tcctcaacga tttagacgct aattctgctt   1800

cttcaggctt tgattcaggt tttctcgtgg accgtctctg cgtgccgcta tggctgaagg   1860

ccagggcgtt caagatcacc cagagctcca ggagcacttc gcagccttcc tcgtcgcccg   1920

acaagacgac ccagactacc agccagtaga cggggacagc ccaccccggg ctagcctgga   1980

ggaggctgaa cagagcagca ctcgtttcga gcacatcagt taccgagacg tggtggatga   2040

cttcaataga tgccatgatg ttttttatga gaggtacagt tttgaggaca taaagagcta   2100

cgaggctttg cctgaggaca atttggagca gctcatagct atgcatgcta aaatcaagct   2160

gctgcccggt cgggagtatg agttgactca acctttgaac ataacatctt gcgcctatgt   2220

gctcggaaat ggggctacta ttagggtaac aggggaagcc tccccggcta ttagagtggg   2280

ggccatggcc gtgggtccgt gtgtaacagg aatgactggg gtgacttttg tgaattgtag   2340

gtttgagaga gagtcaacaa ttagggggtc cctgatacga gcttcaactc acgtgctgtt   2400

tcatggctgt tattttatgg gaattatggg cacttgtatt gaggtggggg cgggagctta   2460

cattcggggt tgtgagtttg tgggctgtta ccggggaatc tgttctactt ctaacagaga   2520

tattaaggtg aggcagtgca actttgacaa atgcttactg ggtattactt gtaaggggga   2580

ctatcgtctt tcgggaaatg tgtgttctga gactttctgc tttgctcatt tagagggaga   2640

gggtttggtt aaaaacaaca cagtcaagtc ccctagtcgc tggaccagcg agtctggctt   2700

ttccatgata acttgtgcag acggcagggt tacgcctttg ggttccctcc acattgtggg   2760

caaccgttgt aggcgttggc caaccatgca ggggaatgtg tttatcatgt ctaaactgta   2820

tctgggcaac agaataggga ctgtagccct gccccagtgt gctttctaca agtccagcat   2880

ttgtttggag gagagggcga caaacaagct ggtcttggct tgtgcttttg agaataatgt   2940

actggtgtac aaagtgctga gacgggagag tccctcaacc gtgaaaatgt gtgtttgtgg   3000

gacttctcat tatgcaaagc ctttgacact ggcaattatt tcttcagata ttcgggctaa   3060

tcgatacatg tacactgtgg actcaacaga gttcacttct gacgaggatt aaaagtgggc   3120

ggggccaaga ggggtataaa taggtgggga ggttgagggg agccgtagtt tctgtttttc   3180

ccagactggg ggggacaac atg gcc gag gaa ggg cgc att tat gtg cct tat    3232
                    Met Ala Glu Glu Gly Arg Ile Tyr Val Pro Tyr
                      1               5                  10

gta act gcc cgc ctg ccc aag tgg tcg ggt tcg gtg cag gat aag acg     3280
Val Thr Ala Arg Leu Pro Lys Trp Ser Gly Ser Val Gln Asp Lys Thr
            15                  20                  25

ggc tcg aac atg ttg ggg ggt gtg gta ctc cct cct aat tca cag gcg     3328
Gly Ser Asn Met Leu Gly Gly Val Val Leu Pro Pro Asn Ser Gln Ala
        30                  35                  40

cac cgg acg gag acc gtg ggc act gag gcc acc aga gac aac ctg cac     3376
His Arg Thr Glu Thr Val Gly Thr Glu Ala Thr Arg Asp Asn Leu His
    45                  50                  55

gcc gag gga gcg cgt cgt cct gag gat cag acg ccc tac atg atc ttg     3424
Ala Glu Gly Ala Arg Arg Pro Glu Asp Gln Thr Pro Tyr Met Ile Leu
 60                  65                  70                  75
```

-continued

```
gtg gag gac tct ctg gga ggt ttg aag agg cga atg gac ttg ctg gaa      3472
Val Glu Asp Ser Leu Gly Gly Leu Lys Arg Arg Met Asp Leu Leu Glu
                 80                  85                  90

gaa tct aat cag cag ctg ctg gca act ctc aac cgt ctc cgt aca gga      3520
Glu Ser Asn Gln Gln Leu Leu Ala Thr Leu Asn Arg Leu Arg Thr Gly
             95                 100                 105

ctc gct gcc tat gtg cag gct aac ctt gtg ggc ggc caa gtt aac ccc      3568
Leu Ala Ala Tyr Val Gln Ala Asn Leu Val Gly Gly Gln Val Asn Pro
        110                 115                 120

ttt gtt taaataaaaa tacactcata cagtttatta tgctgtcaat aaaattcttt      3624
Phe Val
    125

atttttcctg tgataatacc gtgtccagcg tgctctgtca ataagggtcc tatgcatcct   3684

gagaagggcc tcatataccc atggcatgaa tattaagata catgggcata aggccctcag   3744

aagggttgag gtagagccac tgcagacttt cgtggggagg taaggtgttg taaataatcc   3804

agtcatactg actgtgctgg gcgtggaagg aaaagatgtc ttttagaaga agggtgattg   3864

gcaaagggag gctcttagtg taggtattga taaatctgtt cagttgggag ggatgcattc   3924

gggggctaat aaggtggagt ttagcctgaa tcttaaggtt ggcaatgttg ccccctaggt   3984

ctttgcgagg attcatgttg tgcagtacca caaaaacaga gtagcctgtg catttgggga   4044

atttatcatg aagctt                                                   4060


<210> SEQ ID NO 8
<211> LENGTH: 125
<212> TYPE: PRT
<213> ORGANISM: Bovine adenovirus type 3

<400> SEQUENCE: 8

Met Ala Glu Glu Gly Arg Ile Tyr Val Pro Tyr Val Thr Ala Arg Leu
  1               5                  10                  15

Pro Lys Trp Ser Gly Ser Val Gln Asp Lys Thr Gly Ser Asn Met Leu
             20                  25                  30

Gly Gly Val Val Leu Pro Pro Asn Ser Gln Ala His Arg Thr Glu Thr
         35                  40                  45

Val Gly Thr Glu Ala Thr Arg Asp Asn Leu His Ala Glu Gly Ala Arg
     50                  55                  60

Arg Pro Glu Asp Gln Thr Pro Tyr Met Ile Leu Val Glu Asp Ser Leu
 65                  70                  75                  80

Gly Gly Leu Lys Arg Arg Met Asp Leu Leu Glu Glu Ser Asn Gln Gln
                 85                  90                  95

Leu Leu Ala Thr Leu Asn Arg Leu Arg Thr Gly Leu Ala Ala Tyr Val
            100                 105                 110

Gln Ala Asn Leu Val Gly Gly Gln Val Asn Pro Phe Val
        115                 120                 125


<210> SEQ ID NO 9
<211> LENGTH: 54
<212> TYPE: PRT
<213> ORGANISM: Human adenovirus type 5

<400> SEQUENCE: 9

Glu Glu Phe Val Leu Asp Tyr Val Glu His Pro Gly His Gly Cys Arg
  1               5                  10                  15

Ser Cys His Tyr His Arg Arg Asn Thr Gly Asp Pro Asp Ile Met Cys
             20                  25                  30
```

-continued

```
Ser Leu Cys Tyr Met Arg Thr Cys Gly Met Phe Val Tyr Ser Pro Val
         35                  40                  45

Ser Glu Pro Glu Pro Glu
     50


<210> SEQ ID NO 10
<211> LENGTH: 13
<212> TYPE: PRT
<213> ORGANISM: Human adenovirus type 5

<400> SEQUENCE: 10

Ile Asp Leu Thr Cys His Glu Ala Gly Phe Pro Pro Ser
  1               5                  10


<210> SEQ ID NO 11
<211> LENGTH: 19
<212> TYPE: PRT
<213> ORGANISM: Human adenovirus type 5

<400> SEQUENCE: 11

Leu Asp Phe Ser Thr Pro Gly Arg Ala Ala Ala Ala Val Ala Phe Leu
  1               5                  10                  15

Ser Phe Ile


<210> SEQ ID NO 12
<211> LENGTH: 7
<212> TYPE: PRT
<213> ORGANISM: Human adenovirus type 5

<400> SEQUENCE: 12

Gln Ser Ser Asn Ser Thr Ser
  1               5


<210> SEQ ID NO 13
<211> LENGTH: 347
<212> TYPE: PRT
<213> ORGANISM: Human adenovirus type 5

<400> SEQUENCE: 13

Gln Lys Tyr Ser Ile Glu Gln Leu Thr Thr Tyr Trp Leu Gln Pro Gly
  1               5                  10                  15

Asp Asp Phe Glu Glu Ala Ile Arg Val Tyr Ala Lys Val Ala Leu Arg
             20                  25                  30

Pro Asp Cys Lys Tyr Lys Ile Ser Lys Leu Val Asn Ile Arg Asn Cys
         35                  40                  45

Cys Tyr Ile Ser Gly Asn Gly Ala Glu Val Glu Ile Asp Thr Glu Asp
     50                  55                  60

Arg Val Ala Phe Arg Cys Ser Met Ile Asn Met Trp Pro Gly Val Leu
 65                  70                  75                  80

Gly Met Asp Gly Val Val Ile Met Asn Val Arg Phe Thr Gly Pro Asn
                 85                  90                  95

Phe Ser Gly Thr Val Phe Leu Ala Asn Thr Asn Leu Ile Leu His Gly
            100                 105                 110

Val Ser Phe Tyr Gly Phe Asn Asn Thr Cys Val Glu Ala Trp Thr Asp
        115                 120                 125

Val Arg Val Arg Gly Cys Ala Phe Tyr Cys Cys Trp Lys Gly Val Val
    130                 135                 140

Cys Arg Pro Lys Ser Arg Ala Ser Ile Lys Lys Cys Leu Phe Glu Arg
145                 150                 155                 160
```

-continued

```
Cys Thr Leu Gly Ile Leu Ser Glu Gly Asn Ser Arg Val Arg His Asn
                165                 170                 175

Val Ala Ser Asp Cys Gly Cys Phe Met Leu Val Lys Ser Val Ala Val
            180                 185                 190

Ile Lys His Asn Met Val Cys Gly Asn Cys Glu Asp Arg Ala Ser Gln
        195                 200                 205

Met Leu Thr Cys Ser Asp Gly Asn Cys His Leu Leu Lys Thr Ile His
    210                 215                 220

Val Ala Ser His Ser Arg Lys Ala Trp Pro Val Phe Glu His Asn Ile
225                 230                 235                 240

Leu His Arg Cys Ser Leu His Leu Gly Asn Arg Arg Gly Val Phe Leu
                245                 250                 255

Pro Tyr Gln Cys Asn Leu Ser His Thr Lys Ile Leu Leu Glu Pro Glu
            260                 265                 270

Ser Met Ser Lys Val Asn Leu Asn Gly Val Phe Asp Met Thr Met Lys
        275                 280                 285

Ile Trp Lys Val Leu Arg Tyr Asp Glu Thr Arg Thr Arg Cys Arg Pro
    290                 295                 300

Cys Glu Cys Gly Gly Lys His Ile Arg Asn Gln Pro Val Met Leu Asp
305                 310                 315                 320

Val Thr Glu Glu Leu Arg Pro Asp His Leu Val Leu Ala Cys His Arg
                325                 330                 335

Ala Glu Phe Gly Ser Ser Asp Glu Asp Thr Asp
            340                 345
```

<210> SEQ ID NO 14
<211> LENGTH: 140
<212> TYPE: PRT
<213> ORGANISM: Human adenovirus type 5

<400> SEQUENCE: 14

```
Met Ser Thr Asn Ser Phe Asp Gly Ser Ile Val Ser Ser Tyr Leu Thr
  1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
     50                  55                  60

Ala Ser Ala Ala Ala Ala Thr Ala Arg Gly Ile Val Thr Asp Phe Ala
 65                  70                  75                  80

Phe Leu Ser Pro Leu Ala Ser Ser Ala Ala Ser Arg Ser Ser Ala Arg
                 85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Pro Asn Ala Val
    130                 135                 140
```

<210> SEQ ID NO 15
<211> LENGTH: 5100
<212> TYPE: DNA
<213> ORGANISM: Bovine adenovirus type 3
<220> FEATURE:
<221> NAME/KEY: CDS -continued

<222> LOCATION: (2)..(418)

<400> SEQUENCE: 15

```
c ctc atc aaa caa ccc gtg gtg ggc acc acc cac gtg gaa atg cct cgc      49
  Leu Ile Lys Gln Pro Val Val Gly Thr Thr His Val Glu Met Pro Arg
    1               5                  10                  15

aac gaa gtc cta gaa caa cat ctg acc tca cat ggc gct caa atc gcg       97
Asn Glu Val Leu Glu Gln His Leu Thr Ser His Gly Ala Gln Ile Ala
                20                  25                  30

ggc gga ggc gct gcg ggc gat tac ttt aaa agc ccc act tca gct cga      145
Gly Gly Gly Ala Ala Gly Asp Tyr Phe Lys Ser Pro Thr Ser Ala Arg
        35                  40                  45

acc ctt atc ccg ctc acc gcc tcc tgc tta aga cca gat gga gtc ttt      193
Thr Leu Ile Pro Leu Thr Ala Ser Cys Leu Arg Pro Asp Gly Val Phe
    50                  55                  60

caa cta gga gga ggc tcg cgt tca tct ttc aac ccc ctg caa aca gat      241
Gln Leu Gly Gly Gly Ser Arg Ser Ser Phe Asn Pro Leu Gln Thr Asp
 65                  70                  75                  80

ttt gcc ttc cac gcc ctg ccc tcc aga ccg cgc cac ggg ggc ata gga      289
Phe Ala Phe His Ala Leu Pro Ser Arg Pro Arg His Gly Gly Ile Gly
                85                  90                  95

tcc agg cag ttt gta gag gaa ttt gtg ccc gcc gtc tac ctc aac ccc      337
Ser Arg Gln Phe Val Glu Glu Phe Val Pro Ala Val Tyr Leu Asn Pro
            100                 105                 110

tac tcg gga ccg ccg gac tct tat ccg gac cag ttt ata cgc cac tac      385
Tyr Ser Gly Pro Pro Asp Ser Tyr Pro Asp Gln Phe Ile Arg His Tyr
        115                 120                 125

aac gtg tac agc aac tct gtg agc ggt tat agc tgagattgta agactctcct    438
Asn Val Tyr Ser Asn Ser Val Ser Gly Tyr Ser
    130                 135

atctgtctct gtgctgcttt tccgcttcaa gccccacaag catgaagggg tttctgctca    498

tcttcagcct gcttgtgcat tgtcccctaa ttcatgttgg gaccattagc ttctatgctg    558

caaggcccgg gtctgagcct aacgcgactt atgtttgtga ctatggaagc gagtcagatt    618

acaaccccac cacggttctg tggttggctc gagagaccga tggctcctgg atctctgttc    678

ttttccgtca caacggctcc tcaactgcag cccccggggt cgtcgcgcac tttactgacc    738

acaacagcag cattgtggtg ccccagtatt acctcctcaa caactcactc tctaagctct    798

gctgctcata ccggcacaac gagcgttctc agtttacctg caaacaagct gacgtcccta    858

cctgtcacga gcccggcaag ccgctcaccc tccgcgtctc cccgcgctg ggaactgccc     918

accaagcagt cacttggttt tttcaaaatg tacccatagc tactgtttac cgaccttggg    978

gcaatgtaac ttggttttgt cctcccttca tgtgtacctt taatgtcagc ctgaactccc   1038

tacttattta caacttttct gacaaaaccg gggggcaata cacagctctc atgcactccg   1098

gacctgcttc cctctttcag ctctttaagc caacgacttg tgtcaccaag gtggaggacc   1158

cgccgtatgc caacgacccg gcctcgcctg tgtggcgccc actgcttttt gccttcgtcc   1218

tctgcaccgg ctgcgcggtg ttgttaaccg ccttcggtcc atcgattcta tccggtaccc   1278

gaaagcttat ctcagcccgc ttttggagtc ccgagcccta taccaccctc cactaacagt   1338

ccccccatgg agccagacgg agttcatgcc gagcagcagt ttatcctcaa tcagatttcc   1398

tgcgccaaca ctgccctcca gcgtcaaagg gaggaactag cttcccttgt catgttgcat   1458

gcctgtaagc gtggcctctt ttgtccagtc aaaacttaca agctcagcct caacgcctcg   1518

gccagcgagc acagcctgca ctttgaaaaa agtccctccc gattcaccct ggtcaacact   1578

cacgccggag cttctgtgcg agtggcccta caccaccagg gagcttccgg cagcatccgc   1638
```

-continued

```
tgttcctgtt cccacgccga gtgcctcccc gtcctcctca agaccctctg tgcctttaac   1698
tttttagatt agctgaaagc aaatataaaa tggtgtgctt accgtaattc tgttttgact   1758
tgtgtgcttg atttctcccc ctgcgccgta atccagtgcc cctcttcaaa actctcgtac   1818
cctatgcgat tcgcataggc atattttcta aaagctctga agtcaacatc actctcaaac   1878
acttctccgt tgtaggttac tttcatctac agataaagtc atccaccggt taacatcatg   1938
aagagaagtg tgccccagga ctttaatctt gtgtatccgt acaaggctaa gaggcccaac   1998
atcatgccgc cctttttga ccgcaatggc tttgttgaaa accaagaagc cacgctagcc   2058
atgcttgtgg aaaagccgct cacgttcgac aaggaaggtg cgctgaccct gggcgtcgga   2118
cgcggcatcc gcattaaccc cgcggggctt ctggagacaa acgacctcgc gtccgctgtc   2178
ttcccaccgc tggcctccga tgaggccggc aacgtcacgc tcaacatgtc tgacgggcta   2238
tatactaagg acaacaagct agctgtcaaa gtaggtcccg ggctgtccct cgactccaat   2298
aatgctctcc aggtccacac aggcgacggg ctcacggtaa ccgatgacaa ggtgtctcta   2358
aatacccaag ctcccctctc gaccaccagc gcgggcctct ccctacttct gggtcccagc   2418
ctccacttag gtgaggagga acgactaaca gtaaacaccg gagcgggcct ccaaattagc   2478
aataacgctc tggccgtaaa agtaggttca ggtatcaccg tagatgctca aaaccagctc   2538
gctgcatccc tgggggacgg tctagaaagc agagataata aaactgtcgt taaggctggg   2598
cccggactta caataactaa tcaagctctt actgttgcta ccgggaacgg ccttcaggtc   2658
aacccggaag ggcaactgca gctaaacatt actgccggtc agggcctcaa ctttgcaaac   2718
aacagcctcg ccgtggagct gggctcgggc ctgcattttc cccctggcca aaaccaagta   2778
agcctttatc ccggagatgg aatagacatc cgagataata gggtgactgt gcccgctggg   2838
ccaggcctga gaatgctcaa ccaccaactt gccgtagctt ccggagacgg tttagaagtc   2898
cacagcgaca ccctccggtt aaagctctcc cacggcctga catttgaaaa tggcgccgta   2958
cgagcaaaac taggaccagg acttggcaca gacgactctg gtcggtccgt ggttcgcaca   3018
ggtcgaggac ttagagttgc aaacggccaa gtccagatct tcagcggaag aggcaccgcc   3078
atcggcactg atagcagcct cactctcaac atccgggcgc ccctacaatt ttctggaccc   3138
gccttgactg ctagtttgca aggcagtggt ccgattactt acaacagcaa caatggcact   3198
ttcggtctct ctataggccc cggaatgtgg gtagaccaaa acagacttca ggtaaaccca   3258
ggcgctggtt tagtcttcca aggaaacaac cttgtcccaa accttgcgga tccgctggct   3318
atttccgaca gcaaaattag tctcagtctc ggtcccggcc tgacccaagc ttccaacgcc   3378
ctgactttaa gtttaggaaa cgggcttgaa ttctccaatc aagccgttgc tataaaagcg   3438
ggccggggct tacgctttga gtcttcctca caagctttag agagcagcct cacagtcgga   3498
aatggcttaa cgcttaccga tactgtgatc cgccccaacc taggggacgg cctagaggtc   3558
agagacaata aaatcattgt taagctgggc gcgaatcttc gttttgaaaa cggagccgta   3618
accgccggca ccgttaaccc ttctgcgccc gaggcaccac caactctcac tgcagaacca   3678
cccctccgag cctccaactc ccatcttcaa ctgtccctat cggagggctt ggttgtgcat   3738
aacaacgccc ttgctctcca actgggagac ggcatggaag taaatcagca cggacttact   3798
ttaagagtag gctcgggttt gcaaatgcgt gacggcattt taacagttac acccagcggc   3858
actcctattg agcccagact gactgcccca ctgactcaga cagagaatgg aatcgggctc   3918
gctctcggcg ccggcttgga attagacgag agcgcgctcc aagtaaaagt tgggcccggc   3978
```

-continued

```
atgcgcctga accctgtaga aaagtatgta accctgctcc tgggtcctgg ccttagtttt   4038

gggcagccgg ccaacaggac aaattatgat gtgcgcgttt ctgtggagcc ccccatggtt   4098

ttcggacagc gtggtcagct cacattttta gtgggtcacg gactacacat tcaaaattcc   4158

aaacttcagc tcaatttggg acaaggcctc agaactgacc ccgtcaccaa ccagctggaa   4218

gtgcccctcg gtcaaggttt ggaaattgca gacgaatccc aggttagggt taaattgggc   4278

gatggcctgc agtttgattc acaagctcgc atcactaccg ctcctaacat ggtcactgaa   4338

actctgtgga ccggaacagg cagtaatgct aatgttacat ggcggggcta cactgccccc   4398

ggcagcaaac tctttttgag tctcactcgg ttcagcactg gtctagtttt aggaaacatg   4458

actattgaca gcaatgcatc ctttgggcaa tacattaacg cgggacacga acagatcgaa   4518

tgctttatat tgttggacaa tcagggtaac ctaaaagaag gatctaactt gcaaggcact   4578

tgggaagtga agaacaaccc ctctgcttcc aaagctgctt ttttgccttc caccgcccta   4638

taccccatcc tcaacgaaag ccgagggagt cttcctggaa aaaatcttgt gggcatgcaa   4698

gccatactgg gaggcggggg cacttgcact gtgatagcca ccctcaatgg cagacgcagc   4758

aacaactatc ccgcgggcca gtccataatt ttcgtgtggc aagaattcaa caccatagcc   4818

cgccaacctc tgaaccactc tacacttact ttttcttact ggacttaaat aagttggaaa   4878

taaagagtta aactgaatgt ttaagtgcaa cagactttta ttggttttgg ctcacaacaa   4938

attacaacag catagacaag tcataccggt caaacaacac aggctctcga aaacgggcta   4998

accgctccaa gaatctgtca cgcagacgag caagtcctaa atgtttttttc actctcttcg   5058

gggccaagtt cagcatgtat cggattttct gcttacacct tt                      5100


<210> SEQ ID NO 16
<211> LENGTH: 139
<212> TYPE: PRT
<213> ORGANISM: Bovine adenovirus type 3

<400> SEQUENCE: 16

Leu Ile Lys Gln Pro Val Val Gly Thr Thr His Val Glu Met Pro Arg
  1               5                  10                  15

Asn Glu Val Leu Glu Gln His Leu Thr Ser His Gly Ala Gln Ile Ala
            20                  25                  30

Gly Gly Gly Ala Ala Gly Asp Tyr Phe Lys Ser Pro Thr Ser Ala Arg
        35                  40                  45

Thr Leu Ile Pro Leu Thr Ala Ser Cys Leu Arg Pro Asp Gly Val Phe
    50                  55                  60

Gln Leu Gly Gly Gly Ser Arg Ser Ser Phe Asn Pro Leu Gln Thr Asp
 65                  70                  75                  80

Phe Ala Phe His Ala Leu Pro Ser Arg Pro Arg His Gly Gly Ile Gly
                 85                  90                  95

Ser Arg Gln Phe Val Glu Glu Phe Val Pro Ala Val Tyr Leu Asn Pro
            100                 105                 110

Tyr Ser Gly Pro Pro Asp Ser Tyr Pro Asp Gln Phe Ile Arg His Tyr
        115                 120                 125

Asn Val Tyr Ser Asn Ser Val Ser Gly Tyr Ser
    130                 135


<210> SEQ ID NO 17
<211> LENGTH: 5100
<212> TYPE: DNA
<213> ORGANISM: Bovine adenovirus type 3
<220> FEATURE:
```

-continued

```
<221> NAME/KEY: CDS
<222> LOCATION: (408)..(1331)

<400> SEQUENCE: 17

cctcatcaaa caacccgtgg tgggcaccac ccacgtggaa atgcctcgca acgaagtcct     60

agaacaacat ctgacctcac atggcgctca aatcgcgggc ggaggcgctg cgggcgatta    120

ctttaaaagc cccacttcag ctcgaaccct tatcccgctc accgcctcct gcttaagacc    180

agatggagtc tttcaactag gaggaggctc gcgttcatct ttcaaccccc tgcaaacaga    240

ttttgccttc cacgccctgc cctccagacc gcgccacggg ggcataggat ccaggcagtt    300

tgtagaggaa tttgtgcccg ccgtctacct caacccctac tcgggaccgc cggactctta    360

tccggaccag tttatacgcc actacaacgt gtacagcaac tctgtga gcg gtt ata      416
                                                    Ala Val Ile
                                                      1

gct gag att gta aga ctc tcc tat ctg tct ctg tgc tgc ttt tcc gct      464
Ala Glu Ile Val Arg Leu Ser Tyr Leu Ser Leu Cys Cys Phe Ser Ala
      5                  10                  15

tca agc ccc aca agc atg aag ggg ttt ctg ctc atc ttc agc ctg ctt      512
Ser Ser Pro Thr Ser Met Lys Gly Phe Leu Leu Ile Phe Ser Leu Leu
 20                  25                  30                  35

gtg cat tgt ccc cta att cat gtt ggg acc att agc ttc tat gct gca      560
Val His Cys Pro Leu Ile His Val Gly Thr Ile Ser Phe Tyr Ala Ala
                 40                  45                  50

agg ccc ggg tct gag cct aac gcg act tat gtt tgt gac tat gga agc      608
Arg Pro Gly Ser Glu Pro Asn Ala Thr Tyr Val Cys Asp Tyr Gly Ser
             55                  60                  65

gag tca gat tac aac ccc acc acg gtt ctg tgg ttg gct cga gag acc      656
Glu Ser Asp Tyr Asn Pro Thr Thr Val Leu Trp Leu Ala Arg Glu Thr
         70                  75                  80

gat ggc tcc tgg atc tct gtt ctt ttc cgt cac aac ggc tcc tca act      704
Asp Gly Ser Trp Ile Ser Val Leu Phe Arg His Asn Gly Ser Ser Thr
     85                  90                  95

gca gcc ccc ggg gtc gtc gcg cac ttt act gac cac aac agc agc att      752
Ala Ala Pro Gly Val Val Ala His Phe Thr Asp His Asn Ser Ser Ile
100                 105                 110                 115

gtg gtg ccc cag tat tac ctc ctc aac aac tca ctc tct aag ctc tgc      800
Val Val Pro Gln Tyr Tyr Leu Leu Asn Asn Ser Leu Ser Lys Leu Cys
                120                 125                 130

tgc tca tac cgg cac aac gag cgt tct cag ttt acc tgc aaa caa gct      848
Cys Ser Tyr Arg His Asn Glu Arg Ser Gln Phe Thr Cys Lys Gln Ala
            135                 140                 145

gac gtc cct acc tgt cac gag ccc ggc aag ccg ctc acc ctc cgc gtc      896
Asp Val Pro Thr Cys His Glu Pro Gly Lys Pro Leu Thr Leu Arg Val
        150                 155                 160

tcc ccc gcg ctg gga act gcc cac caa gca gtc act tgg ttt ttt caa      944
Ser Pro Ala Leu Gly Thr Ala His Gln Ala Val Thr Trp Phe Phe Gln
    165                 170                 175

aat gta ccc ata gct act gtt tac cga cct tgg ggc aat gta act tgg      992
Asn Val Pro Ile Ala Thr Val Tyr Arg Pro Trp Gly Asn Val Thr Trp
180                 185                 190                 195

ttt tgt cct ccc ttc atg tgt acc ttt aat gtc agc ctg aac tcc cta     1040
Phe Cys Pro Pro Phe Met Cys Thr Phe Asn Val Ser Leu Asn Ser Leu
                200                 205                 210

ctt att tac aac ttt tct gac aaa acc ggg ggg caa tac aca gct ctc     1088
Leu Ile Tyr Asn Phe Ser Asp Lys Thr Gly Gly Gln Tyr Thr Ala Leu
            215                 220                 225
```

-continued

```
atg cac tcc gga cct gct tcc ctc ttt cag ctc ttt aag cca acg act      1136
Met His Ser Gly Pro Ala Ser Leu Phe Gln Leu Phe Lys Pro Thr Thr
        230                 235                 240

tgt gtc acc aag gtg gag gac ccg ccg tat gcc aac gac ccg gcc tcg      1184
Cys Val Thr Lys Val Glu Asp Pro Pro Tyr Ala Asn Asp Pro Ala Ser
    245                 250                 255

cct gtg tgg cgc cca ctg ctt ttt gcc ttc gtc ctc tgc acc ggc tgc      1232
Pro Val Trp Arg Pro Leu Leu Phe Ala Phe Val Leu Cys Thr Gly Cys
260                 265                 270                 275

gcg gtg ttg tta acc gcc ttc ggt cca tcg att cta tcc ggt acc cga      1280
Ala Val Leu Leu Thr Ala Phe Gly Pro Ser Ile Leu Ser Gly Thr Arg
                280                 285                 290

aag ctt atc tca gcc cgc ttt tgg agt ccc gag ccc tat acc acc ctc      1328
Lys Leu Ile Ser Ala Arg Phe Trp Ser Pro Glu Pro Tyr Thr Thr Leu
            295                 300                 305

cac taacagtccc cccatggagc cagacggagt tcatgccgag cagcagttta           1381
His

tcctcaatca gatttcctgc gccaacactg ccctccagcg tcaaagggag gaactagctt   1441

cccttgtcat gttgcatgcc tgtaagcgtg gcctcttttg tccagtcaaa acttacaagc   1501

tcagcctcaa cgcctcggcc agcgagcaca gcctgcactt tgaaaaaagt ccctcccgat   1561

tcaccctggt caacactcac gccggagctt ctgtgcgagt ggccctacac caccagggag   1621

cttccggcag catccgctgt tcctgttccc acgccgagtg cctccccgtc ctcctcaaga   1681

ccctctgtgc ctttaacttt ttagattagc tgaaagcaaa tataaaatgg tgtgcttacc   1741

gtaattctgt tttgacttgt gtgcttgatt tctccccctg cgccgtaatc cagtgcccct   1801

cttcaaaact ctcgtaccct atgcgattcg cataggcata ttttctaaaa gctctgaagt   1861

caacatcact ctcaaacact tctccgttgt aggttacttt catctacaga taaagtcatc   1921

caccggttaa catcatgaag agaagtgtgc cccaggactt taatcttgtg tatccgtaca   1981

aggctaagag gcccaacatc atgccgccct tttttgaccg caatggcttt gttgaaaacc   2041

aagaagccac gctagccatg cttgtggaaa agccgctcac gttcgacaag gaaggtgcgc   2101

tgaccctggg cgtcggacgc ggcatccgca ttaaccccgc ggggcttctg gagacaaacg   2161

acctcgcgtc cgctgtcttc ccaccgctgg cctccgatga ggccggcaac gtcacgctca   2221

acatgtctga cgggctatat actaaggaca acaagctagc tgtcaaagta ggtcccgggc   2281

tgtccctcga ctccaataat gctctccagg tccacacagg cgacgggctc acggtaaccg   2341

atgacaaggt gtctctaaat acccaagctc ccctctcgac caccagcgcg ggcctctccc   2401

tacttctggg tcccagcctc cacttaggtg aggaggaacg actaacagta aacaccggag   2461

cgggcctcca aattagcaat aacgctctgg ccgtaaaagt aggttcaggt atcaccgtag   2521

atgctcaaaa ccagctcgct gcatccctgg gggacggtct agaaagcaga gataataaaa   2581

ctgtcgttaa ggctgggccc ggacttacaa taactaatca agctcttact gttgctaccg   2641

ggaacggcct tcaggtcaac ccggaagggc aactgcagct aaacattact gccggtcagg   2701

gcctcaactt tgcaaacaac agcctcgccg tggagctggg ctcgggcctg cattttcccc   2761

ctggccaaaa ccaagtaagc ctttatcccg gagatggaat agacatccga gataataggg   2821

tgactgtgcc cgctgggcca ggcctgagaa tgctcaacca ccaacttgcc gtagcttccg   2881

gagacggttt agaagtccac agcgacaccc tccggttaaa gctctcccac ggcctgacat   2941

ttgaaaatgg cgccgtacga gcaaaactag gaccaggact tggcacagac gactctggtc   3001

ggtccgtggt tcgcacaggt cgaggactta gagttgcaaa cggccaagtc cagatcttca   3061
```

-continued

```
gcggaagagg caccgccatc ggcactgata gcagcctcac tctcaacatc cgggcgcccc   3121
tacaattttc tggacccgcc ttgactgcta gtttgcaagg cagtggtccg attacttaca   3181
acagcaacaa tggcactttc ggtctctcta taggccccgg aatgtgggta gaccaaaaca   3241
gacttcaggt aaacccaggc gctggtttag tcttccaagg aaacaacctt gtcccaaacc   3301
ttgcggatcc gctggctatt tccgacagca aaattagtct cagtctcggt cccggcctga   3361
cccaagcttc caacgccctg actttaagtt taggaaacgg gcttgaattc tccaatcaag   3421
ccgttgctat aaaagcgggc cggggcttac gctttgagtc ttcctcacaa gctttagaga   3481
gcagcctcac agtcggaaat ggcttaacgc ttaccgatac tgtgatccgc cccaacctag   3541
gggacggcct agaggtcaga gacaataaaa tcattgttaa gctgggcgcg aatcttcgtt   3601
ttgaaaacgg agccgtaacc gccggcaccg ttaacccttc tgcgcccgag gcaccaccaa   3661
ctctcactgc agaaccaccc ctccgagcct ccaactccca tcttcaactg tccctatcgg   3721
agggcttggt tgtgcataac aacgcccttg ctctccaact gggagacggc atggaagtaa   3781
atcagcacgg acttacttta agagtaggct cgggtttgca aatgcgtgac ggcattttaa   3841
cagttacacc cagcggcact cctattgagc ccagactgac tgccccactg actcagacag   3901
agaatggaat cgggctcgct ctcggcgccg gcttggaatt agacgagagc gcgctccaag   3961
taaaagttgg gcccggcatg cgcctgaacc ctgtagaaaa gtatgtaacc ctgctcctgg   4021
gtcctggcct tagttttggg cagccggcca acaggacaaa ttatgatgtg cgcgtttctg   4081
tggagccccc catggttttc ggacagcgtg gtcagctcac atttttagtg ggtcacggac   4141
tacacattca aaattccaaa cttcagctca atttgggaca aggcctcaga actgaccccg   4201
tcaccaacca gctggaagtg cccctcggtc aaggtttgga aattgcagac gaatcccagg   4261
ttagggttaa attgggcgat ggcctgcagt ttgattcaca agctcgcatc actaccgctc   4321
ctaacatggt cactgaaact ctgtggaccg gaacaggcag taatgctaat gttacatggc   4381
ggggctacac tgcccccggc agcaaactct ttttgagtct cactcggttc agcactggtc   4441
tagttttagg aaacatgact attgacagca atgcatcctt tgggcaatac attaacgcgg   4501
gacacgaaca gatcgaatgc tttatattgt tggacaatca gggtaaccta aaagaaggat   4561
ctaacttgca aggcacttgg gaagtgaaga acaacccctc tgcttccaaa gctgcttttt   4621
tgccttccac cgccctatac ccatcctca acgaaagccg agggagtctt cctggaaaaa    4681
atcttgtggg catgcaagcc atactgggag gcgggggcac ttgcactgtg atagccaccc   4741
tcaatggcag acgcagcaac aactatcccg cgggccagtc cataattttc gtgtggcaag   4801
aattcaacac catagcccgc caacctctga accactctac acttactttt tcttactgga   4861
cttaaataag ttggaaataa agagttaaac tgaatgttta agtgcaacag acttttattg   4921
gttttggctc acaacaaatt acaacagcat agacaagtca taccggtcaa acaacacagg   4981
ctctcgaaaa cggctaacc gctccaagaa tctgtcacgc agacgagcaa gtcctaaatg    5041
ttttttcact ctcttcgggg ccaagttcag catgtatcgg attttctgct tacacctttt   5100
```

<210> SEQ ID NO 18
<211> LENGTH: 308
<212> TYPE: PRT
<213> ORGANISM: Bovine adenovirus type 3

<400> SEQUENCE: 18

```
Ala Val Ile Ala Glu Ile Val Arg Leu Ser Tyr Leu Ser Leu Cys Cys
  1               5                  10                  15
```

-continued

Phe Ser Ala Ser Ser Pro Thr Ser Met Lys Gly Phe Leu Leu Ile Phe
20 25 30

Ser Leu Leu Val His Cys Pro Leu Ile His Val Gly Thr Ile Ser Phe
35 40 45

Tyr Ala Ala Arg Pro Gly Ser Glu Pro Asn Ala Thr Tyr Val Cys Asp
50 55 60

Tyr Gly Ser Glu Ser Asp Tyr Asn Pro Thr Thr Val Leu Trp Leu Ala
65 70 75 80

Arg Glu Thr Asp Gly Ser Trp Ile Ser Val Leu Phe Arg His Asn Gly
85 90 95

Ser Ser Thr Ala Ala Pro Gly Val Val Ala His Phe Thr Asp His Asn
100 105 110

Ser Ser Ile Val Val Pro Gln Tyr Tyr Leu Leu Asn Asn Ser Leu Ser
115 120 125

Lys Leu Cys Cys Ser Tyr Arg His Asn Glu Arg Ser Gln Phe Thr Cys
130 135 140

Lys Gln Ala Asp Val Pro Thr Cys His Glu Pro Gly Lys Pro Leu Thr
145 150 155 160

Leu Arg Val Ser Pro Ala Leu Gly Thr Ala His Gln Ala Val Thr Trp
165 170 175

Phe Phe Gln Asn Val Pro Ile Ala Thr Val Tyr Arg Pro Trp Gly Asn
180 185 190

Val Thr Trp Phe Cys Pro Pro Phe Met Cys Thr Phe Asn Val Ser Leu
195 200 205

Asn Ser Leu Leu Ile Tyr Asn Phe Ser Asp Lys Thr Gly Gly Gln Tyr
210 215 220

Thr Ala Leu Met His Ser Gly Pro Ala Ser Leu Phe Gln Leu Phe Lys
225 230 235 240

Pro Thr Thr Cys Val Thr Lys Val Glu Asp Pro Pro Tyr Ala Asn Asp
245 250 255

Pro Ala Ser Pro Val Trp Arg Pro Leu Leu Phe Ala Phe Val Leu Cys
260 265 270

Thr Gly Cys Ala Val Leu Leu Thr Ala Phe Gly Pro Ser Ile Leu Ser
275 280 285

Gly Thr Arg Lys Leu Ile Ser Ala Arg Phe Trp Ser Pro Glu Pro Tyr
290 295 300

Thr Thr Leu His
305

<210> SEQ ID NO 19
<211> LENGTH: 5100
<212> TYPE: DNA
<213> ORGANISM: Bovine adenovirus type 3
<220> FEATURE:
<221> NAME/KEY: CDS
<222> LOCATION: (529)..(954)

<400> SEQUENCE: 19
cctcatcaaa caacccgtgg tgggcaccac ccacgtggaa atgcctcgca acgaagtcct 60
agaacaacat ctgacctcac atggcgctca aatcgcgggc ggaggcgctg cgggcgatta 120
ctttaaaagc cccacttcag ctcgaaccct tatcccgctc accgcctcct gcttaagacc 180
agatggagtc tttcaactag gaggaggctc gcgttcatct ttcaaccccc tgcaaacaga 240
ttttgccttc cacgccctgc cctccagacc gcgccacggg ggcataggat ccaggcagtt 300
tgtagaggaa tttgtgcccg ccgtctacct caacccctac tcgggaccgc cggactctta 360

-continued

```
tccggaccag tttatacgcc actacaacgt gtacagcaac tctgtgagcg gttatagctg    420

agattgtaag actctcctat ctgtctctgt gctgcttttc cgcttcaagc cccacaagca    480

tgaaggggtt tctgctcatc ttcagcctgc ttgtgcattg tcccctaa ttc atg ttg     537
                                                     Phe Met Leu
                                                       1

gga cca tta gct tct atg ctg caa ggc ccg ggt ctg agc cta acg cga      585
Gly Pro Leu Ala Ser Met Leu Gln Gly Pro Gly Leu Ser Leu Thr Arg
      5                  10                  15

ctt atg ttt gtg act atg gaa gcg agt cag att aca acc cca cca cgg      633
Leu Met Phe Val Thr Met Glu Ala Ser Gln Ile Thr Thr Pro Pro Arg
 20                  25                  30                  35

ttc tgt ggt tgg ctc gag aga ccg atg gct cct gga tct ctg ttc ttt      681
Phe Cys Gly Trp Leu Glu Arg Pro Met Ala Pro Gly Ser Leu Phe Phe
                 40                  45                  50

tcc gtc aca acg gct cct caa ctg cag ccc ccg ggg tcg tcg cgc act      729
Ser Val Thr Thr Ala Pro Gln Leu Gln Pro Pro Gly Ser Ser Arg Thr
             55                  60                  65

tta ctg acc aca aca gca gca ttg tgg tgc ccc agt att acc tcc tca      777
Leu Leu Thr Thr Thr Ala Ala Leu Trp Cys Pro Ser Ile Thr Ser Ser
         70                  75                  80

aca act cac tct cta agc tct gct gct cat acc ggc aca acg agc gtt      825
Thr Thr His Ser Leu Ser Ser Ala Ala His Thr Gly Thr Thr Ser Val
     85                  90                  95

ctc agt tta cct gca aac aag ctg acg tcc cta cct gtc acg agc ccg      873
Leu Ser Leu Pro Ala Asn Lys Leu Thr Ser Leu Pro Val Thr Ser Pro
100                 105                 110                 115

gca agc cgc tca ccc tcc gcg tct ccc ccg cgc tgg gaa ctg ccc acc      921
Ala Ser Arg Ser Pro Ser Ala Ser Pro Pro Arg Trp Glu Leu Pro Thr
                120                 125                 130

aag cag tca ctt ggt ttt ttc aaa atg tac cca tagctactgt ttaccgacct    974
Lys Gln Ser Leu Gly Phe Phe Lys Met Tyr Pro
            135                 140

tggggcaatg taacttggtt ttgtcctccc ttcatgtgta cctttaatgt cagcctgaac   1034

tccctactta tttacaactt ttctgacaaa accggggggc aatacacagc tctcatgcac   1094

tccggacctg cttccctctt tcagctcttt aagccaacga cttgtgtcac caaggtggag   1154

gacccgccgt atgccaacga cccggcctcg cctgtgtggc gcccactgct ttttgccttc   1214

gtcctctgca ccggctgcgc ggtgttgtta accgccttcg gtccatcgat tctatccggt   1274

acccgaaagc ttatctcagc ccgcttttgg agtcccgagc cctataccac cctccactaa   1334

cagtcccccc atggagccag acggagttca tgccgagcag cagtttatcc tcaatcagat   1394

ttcctgcgcc aacactgccc tccagcgtca aagggaggaa ctagcttccc ttgtcatgtt   1454

gcatgcctgt aagcgtggcc tcttttgtcc agtcaaaact tacaagctca gcctcaacgc   1514

ctcggccagc gagcacagcc tgcactttga aaaaagtccc tcccgattca ccctggtcaa   1574

cactcacgcc ggagcttctg tgcgagtggc cctacaccac cagggagctt ccggcagcat   1634

ccgctgttcc tgttcccacg ccgagtgcct ccccgtcctc ctcaagaccc tctgtgcctt   1694

taacttttta gattagctga aagcaaatat aaaatggtgt gcttaccgta attctgtttt   1754

gacttgtgtg cttgatttct ccccctgcgc cgtaatccag tgcccctctt caaaactctc   1814

gtaccctatg cgattcgcat aggcatattt tctaaaagct ctgaagtcaa catcactctc   1874

aaacacttct ccgttgtagg ttactttcat ctacagataa agtcatccac cggttaacat   1934

catgaagaga agtgtgcccc aggactttaa tcttgtgtat ccgtacaagg ctaagaggcc   1994
```

-continued

```
caacatcatg ccgccctttt ttgaccgcaa tggctttgtt gaaaaccaag aagccacgct   2054
agccatgctt gtggaaaagc cgctcacgtt cgacaaggaa ggtgcgctga ccctgggcgt   2114
cggacgcggc atccgcatta accccgcggg gcttctggag acaaacgacc tcgcgtccgc   2174
tgtcttccca ccgctggcct ccgatgaggc cggcaacgtc acgctcaaca tgtctgacgg   2234
gctatatact aaggacaaca agctagctgt caaagtaggt cccgggctgt ccctcgactc   2294
caataatgct ctccaggtcc acacaggcga cgggctcacg gtaaccgatg acaaggtgtc   2354
tctaaatacc caagctcccc tctcgaccac cagcgcgggc ctctccctac ttctgggtcc   2414
cagcctccac ttaggtgagg aggaacgact aacagtaaac accggagcgg gcctccaaat   2474
tagcaataac gctctggccg taaaagtagg ttcaggtatc accgtagatg ctcaaaacca   2534
gctcgctgca tccctggggg acggtctaga aagcagagat aataaaactg tcgttaaggc   2594
tgggcccgga cttacaataa ctaatcaagc tcttactgtt gctaccggga acggccttca   2654
ggtcaacccg gaagggcaac tgcagctaaa cattactgcc ggtcagggcc tcaactttgc   2714
aaacaacagc ctcgccgtgg agctgggctc gggcctgcat tttcccccctg gccaaaacca   2774
agtaagcctt tatcccggag atggaataga catccgagat aatagggtga ctgtgcccgc   2834
tgggccaggc ctgagaatgc tcaaccacca acttgccgta gcttccggag acggtttaga   2894
agtccacagc gacaccctcc ggttaaagct ctcccacggc ctgacatttg aaaatggcgc   2954
cgtacgagca aaactaggac caggacttgg cacagacgac tctggtcggt ccgtggttcg   3014
cacaggtcga ggacttagag ttgcaaacgg ccaagtccag atcttcagcg gaagaggcac   3074
cgccatcggc actgatagca gcctcactct caacatccgg gcgcccctac aattttctgg   3134
acccgccttg actgctagtt tgcaaggcag tggtccgatt acttacaaca gcaacaatgg   3194
cactttcggt ctctctatag gccccggaat gtgggtagac caaaacagac ttcaggtaaa   3254
cccaggcgct ggtttagtct tccaaggaaa caaccttgtc ccaaaccttg cggatccgct   3314
ggctatttcc gacagcaaaa ttagtctcag tctcggtccc ggcctgaccc aagcttccaa   3374
cgccctgact ttaagtttag gaaacgggct tgaattctcc aatcaagccg ttgctataaa   3434
agcgggccgg ggcttacgct ttgagtcttc ctcacaagct ttagagagca gcctcacagt   3494
cggaaatggc ttaacgctta ccgatactgt gatccgcccc aacctagggg acggcctaga   3554
ggtcagagac aataaaatca ttgttaagct gggcgcgaat cttcgttttg aaaacggagc   3614
cgtaaccgcc ggcaccgtta acccttctgc gcccgaggca ccaccaactc tcactgcaga   3674
accacccctc cgagcctcca actcccatct tcaactgtcc ctatcggagg gcttggttgt   3734
gcataacaac gcccttgctc tccaactggg agacggcatg gaagtaaatc agcacggact   3794
tactttaaga gtaggctcgg gtttgcaaat gcgtgacggc attttaacag ttacacccag   3854
cggcactcct attgagccca gactgactgc cccactgact cagacagaga atggaatcgg   3914
gctcgctctc ggcgccggct tggaattaga cgagagcgcg ctccaagtaa aagttgggcc   3974
cggcatgcgc ctgaaccctg tagaaaagta tgtaaccctg ctcctgggtc ctggccttag   4034
ttttgggcag ccggccaaca ggacaaatta tgatgtgcgc gtttctgtgg agccccccat   4094
ggttttcgga cagcgtggtc agctcacatt tttagtgggt cacggactac acattcaaaa   4154
ttccaaactt cagctcaatt tgggacaagg cctcagaact gaccccgtca ccaaccagct   4214
ggaagtgccc ctcggtcaag gtttggaaat tgcagacgaa tcccaggtta gggttaaatt   4274
gggcgatggc ctgcagtttg attcacaagc tcgcatcact accgctccta acatggtcac   4334
tgaaactctg tggaccggaa caggcagtaa tgctaatgtt acatggcggg gctacactgc   4394
```

-continued

```
ccccggcagc aaactctttt tgagtctcac tcggttcagc actggtctag ttttaggaaa   4454

catgactatt gacagcaatg catcctttgg gcaatacatt aacgcgggac acgaacagat   4514

cgaatgcttt atattgttgg acaatcaggg taacctaaaa gaaggatcta acttgcaagg   4574

cacttgggaa gtgaagaaca acccctctgc ttccaaagct gctttttttgc cttccaccgc  4634

cctatacccc atcctcaacg aaagccgagg gagtcttcct ggaaaaaatc ttgtgggcat   4694

gcaagccata ctgggaggcg ggggcacttg cactgtgata gccaccctca atggcagacg   4754

cagcaacaac tatcccgcgg gccagtccat aattttcgtg tggcaagaat tcaacaccat   4814

agcccgccaa cctctgaacc actctacact tactttttct tactggactt aaataagttg   4874

gaaataaaga gttaaactga atgtttaagt gcaacagact tttattggtt ttggctcaca   4934

acaaattaca acagcataga caagtcatac cggtcaaaca acacaggctc tcgaaaacgg   4994

gctaaccgct ccaagaatct gtcacgcaga cgagcaagtc ctaaatgttt tttcactctc   5054

ttcggggcca agttcagcat gtatcggatt ttctgcttac accttt                  5100
```

<210> SEQ ID NO 20
<211> LENGTH: 142
<212> TYPE: PRT
<213> ORGANISM: Bovine adenovirus type 3

<400> SEQUENCE: 20

```
Phe Met Leu Gly Pro Leu Ala Ser Met Leu Gln Gly Pro Gly Leu Ser
  1               5                  10                  15

Leu Thr Arg Leu Met Phe Val Thr Met Glu Ala Ser Gln Ile Thr Thr
             20                  25                  30

Pro Pro Arg Phe Cys Gly Trp Leu Glu Arg Pro Met Ala Pro Gly Ser
         35                  40                  45

Leu Phe Phe Ser Val Thr Thr Ala Pro Gln Leu Gln Pro Pro Gly Ser
     50                  55                  60

Ser Arg Thr Leu Leu Thr Thr Thr Ala Ala Leu Trp Cys Pro Ser Ile
 65                  70                  75                  80

Thr Ser Ser Thr Thr His Ser Leu Ser Ser Ala Ala His Thr Gly Thr
                 85                  90                  95

Thr Ser Val Leu Ser Leu Pro Ala Asn Lys Leu Thr Ser Leu Pro Val
            100                 105                 110

Thr Ser Pro Ala Ser Arg Ser Pro Ser Ala Ser Pro Pro Arg Trp Glu
        115                 120                 125

Leu Pro Thr Lys Gln Ser Leu Gly Phe Phe Lys Met Tyr Pro
    130                 135                 140
```

<210> SEQ ID NO 21
<211> LENGTH: 5100
<212> TYPE: DNA
<213> ORGANISM: Bovine adenovirus type 3
<220> FEATURE:
<221> NAME/KEY: CDS
<222> LOCATION: (1246)..(1707)

<400> SEQUENCE: 21

```
cctcatcaaa caacccgtgg tgggcaccac ccacgtggaa atgcctcgca acgaagtcct     60

agaacaacat ctgacctcac atggcgctca aatcgcgggc ggaggcgctg cgggcgatta    120

ctttaaaagc cccacttcag ctcgaaccct tatcccgctc accgcctcct gcttaagacc    180

agatggagtc tttcaactag gaggaggctc gcgttcatct ttcaaccccc tgcaaacaga    240
```

-continued

```
ttttgccttc cacgccctgc cctccagacc gcgccacggg ggcataggat ccaggcagtt    300

tgtagaggaa tttgtgcccg ccgtctacct caacccctac tcgggaccgc cggactctta    360

tccggaccag tttatacgcc actacaacgt gtacagcaac tctgtgagcg gttatagctg    420

agattgtaag actctcctat ctgtctctgt gctgcttttc cgcttcaagc cccacaagca    480

tgaaggggtt tctgctcatc ttcagcctgc ttgtgcattg tcccctaatt catgttggga    540

ccattagctt ctatgctgca aggcccgggt ctgagcctaa cgcgacttat gtttgtgact    600

atggaagcga gtcagattac aaccccacca cggttctgtg gttggctcga gagaccgatg    660

gctcctggat ctctgttctt ttccgtcaca acggctcctc aactgcagcc cccggggtcg    720

tcgcgcactt tactgaccac aacagcagca ttgtggtgcc ccagtattac ctcctcaaca    780

actcactctc taagctctgc tgctcatacc ggcacaacga gcgttctcag tttacctgca    840

aacaagctga cgtccctacc tgtcacgagc ccggcaagcc gctcaccctc cgcgtctccc    900

ccgcgctggg aactgcccac caagcagtca cttggttttt tcaaaatgta cccatagcta    960

ctgtttaccg accttggggc aatgtaactt ggttttgtcc tcccttcatg tgtaccttta   1020

atgtcagcct gaactcccta cttatttaca actttctgga caaaaccggg ggcaatacaa   1080

cagctctcat gcactccgga cctgcttccc tctttcagct ctttaagcca acgacttgtg   1140

tcaccaaggt ggaggacccg ccgtatgcca acgacccggc ctcgcctgtg tggcgcccac   1200

tgctttttgc cttcgtcctc tgcaccggct gcgcggtgtt gttaa ccg cct tcg gtc   1257
                                                  Pro Pro Ser Val
                                                    1

cat cga ttc tat ccg gta ccc gaa agc tta tct cag ccc gct ttt gga     1305
His Arg Phe Tyr Pro Val Pro Glu Ser Leu Ser Gln Pro Ala Phe Gly
  5                  10                  15                  20

gtc ccg agc cct ata cca ccc tcc act aac agt ccc ccc atg gag cca     1353
Val Pro Ser Pro Ile Pro Pro Ser Thr Asn Ser Pro Pro Met Glu Pro
                 25                  30                  35

gac gga gtt cat gcc gag cag cag ttt atc ctc aat cag att tcc tgc     1401
Asp Gly Val His Ala Glu Gln Gln Phe Ile Leu Asn Gln Ile Ser Cys
             40                  45                  50

gcc aac act gcc ctc cag cgt caa agg gag gaa cta gct tcc ctt gtc     1449
Ala Asn Thr Ala Leu Gln Arg Gln Arg Glu Glu Leu Ala Ser Leu Val
         55                  60                  65

atg ttg cat gcc tgt aag cgt ggc ctc ttt tgt cca gtc aaa act tac     1497
Met Leu His Ala Cys Lys Arg Gly Leu Phe Cys Pro Val Lys Thr Tyr
     70                  75                  80

aag ctc agc ctc aac gcc tcg gcc agc gag cac agc ctg cac ttt gaa     1545
Lys Leu Ser Leu Asn Ala Ser Ala Ser Glu His Ser Leu His Phe Glu
 85                  90                  95                 100

aaa agt ccc tcc cga ttc acc ctg gtc aac act cac gcc gga gct tct     1593
Lys Ser Pro Ser Arg Phe Thr Leu Val Asn Thr His Ala Gly Ala Ser
                105                 110                 115

gtg cga gtg gcc cta cac cac cag gga gct tcc ggc agc atc cgc tgt     1641
Val Arg Val Ala Leu His His Gln Gly Ala Ser Gly Ser Ile Arg Cys
            120                 125                 130

tcc tgt tcc cac gcc gag tgc ctc ccc gtc ctc ctc aag acc ctc tgt     1689
Ser Cys Ser His Ala Glu Cys Leu Pro Val Leu Leu Lys Thr Leu Cys
        135                 140                 145

gcc ttt aac ttt tta gat tagctgaaag caaatataaa atggtgtgct            1737
Ala Phe Asn Phe Leu Asp
    150

taccgtaatt ctgttttgac ttgtgtgctt gatttctccc cctgcgccgt aatccagtgc   1797

ccctcttcaa aactctcgta ccctatgcga ttcgcatagg catattttct aaaagctctg   1857
```

-continued

```
aagtcaacat cactctcaaa cacttctccg ttgtaggtta ctttcatcta cagataaagt   1917
catccaccgg ttaacatcat gaagagaagt gtgccccagg actttaatct tgtgtatccg   1977
tacaaggcta agaggcccaa catcatgccg cccttttttg accgcaatgg ctttgttgaa   2037
aaccaagaag ccacgctagc catgcttgtg gaaaagccgc tcacgttcga caaggaaggt   2097
gcgctgaccc tgggcgtcgg acgcggcatc cgcattaacc ccgcggggct tctggagaca   2157
aacgacctcg cgtccgctgt cttcccaccg ctggcctccg atgaggccgg caacgtcacg   2217
ctcaacatgt ctgacgggct atatactaag gacaacaagc tagctgtcaa agtaggtccc   2277
gggctgtccc tcgactccaa taatgctctc caggtccaca caggcgacgg gctcacggta   2337
accgatgaca aggtgtctct aaatacccaa gctcccctct cgaccaccag cgcgggcctc   2397
tccctacttc tgggtcccag cctccactta ggtgaggagg aacgactaac agtaaacacc   2457
ggagcgggcc tccaaattag caataacgct ctggccgtaa aagtaggttc aggtatcacc   2517
gtagatgctc aaaaccagct cgctgcatcc ctgggggacg gtctagaaag cagagataat   2577
aaaactgtcg ttaaggctgg gcccggactt acaataacta atcaagctct tactgttgct   2637
accgggaacg gccttcaggt caacccggaa gggcaactgc agctaaacat tactgccggt   2697
cagggcctca actttgcaaa caacagcctc gccgtggagc tgggctcggg cctgcatttt   2757
cccccctggcc aaaaccaagt aagcctttat cccggagatg gaatagacat ccgagataat   2817
agggtgactg tgcccgctgg gccaggcctg agaatgctca accaccaact tgccgtagct   2877
tccggagacg gtttagaagt ccacagcgac accctccggt taaagctctc ccacggcctg   2937
acatttgaaa atggcgccgt acgagcaaaa ctaggaccag gacttggcac agacgactct   2997
ggtcggtccg tggttcgcac aggtcgagga cttagagttg caaacggcca agtccagatc   3057
ttcagcggaa gaggcaccgc catcggcact gatagcagcc tcactctcaa catccgggcg   3117
cccctacaat tttctggacc cgccttgact gctagtttgc aaggcagtgg tccgattact   3177
tacaacagca acaatggcac tttcggtctc tctataggcc ccggaatgtg ggtagaccaa   3237
aacagacttc aggtaaaccc aggcgctggt ttagtcttcc aaggaaacaa ccttgtccca   3297
aaccttgcgg atccgctggc tatttccgac agcaaaatta gtctcagtct cggtcccggc   3357
ctgacccaag cttccaacgc cctgacttta agtttaggaa acgggcttga attctccaat   3417
caagccgttg ctataaaagc gggccggggc ttacgctttg agtcttcctc acaagcttta   3477
gagagcagcc tcacagtcgg aaatggctta acgcttaccg atactgtgat ccgccccaac   3537
ctaggggacg gcctagaggt cagagacaat aaaatcattg ttaagctggg cgcgaatctt   3597
cgttttgaaa acggagccgt aaccgccggc accgttaacc cttctgcgcc cgaggcacca   3657
ccaactctca ctgcagaacc acccctccga gcctccaact cccatcttca actgtcccta   3717
tcggagggct tggttgtgca taacaacgcc cttgctctcc aactgggaga cggcatggaa   3777
gtaaatcagc acggacttac tttaagagta ggctcgggtt tgcaaatgcg tgacggcatt   3837
ttaacagtta cacccagcgg cactcctatt gagcccagac tgactgcccc actgactcag   3897
acagagaatg gaatcgggct cgctctcggc gccggcttgg aattagacga gagcgcgctc   3957
caagtaaaag ttgggcccgg catgcgcctg aaccctgtag aaaagtatgt aaccctgctc   4017
ctgggtcctg gccttagttt tgggcagccg gccaacagga caaattatga tgtgcgcgtt   4077
tctgtggagc cccccatggt tttcggacag cgtggtcagc tcacattttt agtgggtcac   4137
ggactacaca ttcaaaattc caaacttcag ctcaatttgg gacaaggcct cagaactgac   4197
```

-continued cccgtcacca accagctgga agtgcccctc ggtcaaggtt tggaaattgc agacgaatcc 4257 caggttaggg ttaaattggg cgatggcctg cagtttgatt cacaagctcg catcactacc 4317 gctcctaaca tggtcactga aactctgtgg accggaacag gcagtaatgc taatgttaca 4377 tggcggggct acactgcccc cggcagcaaa ctctttttga gtctcactcg gttcagcact 4437 ggtctagttt taggaaacat gactattgac agcaatgcat cctttgggca atacattaac 4497 gcgggacacg aacagatcga atgctttata ttgttggaca atcagggtaa cctaaaagaa 4557 ggatctaact tgcaaggcac ttgggaagtg aagaacaacc cctctgcttc caaagctgct 4617 tttttgcctt ccaccgccct ataccccatc ctcaacgaaa gccgagggag tcttcctgga 4677 aaaaatcttg tgggcatgca agccatactg ggaggcgggg gcacttgcac tgtgatagcc 4737 accctcaatg gcagacgcag caacaactat cccgcgggcc agtccataat tttcgtgtgg 4797 caagaattca acaccatagc ccgccaacct ctgaaccact ctacacttac tttttcttac 4857 tggacttaaa taagttggaa ataaagagtt aaactgaatg tttaagtgca acagactttt 4917 attggttttg gctcacaaca aattacaaca gcatagacaa gtcataccgg tcaaacaaca 4977 caggctctcg aaaacgggct aaccgctcca agaatctgtc acgcagacga gcaagtccta 5037 aatgtttttt cactctcttc ggggccaagt tcagcatgta tcggattttc tgcttacacc 5097 ttt 5100

<210> SEQ ID NO 22
<211> LENGTH: 154
<212> TYPE: PRT
<213> ORGANISM: Bovine adenovirus type 3

<400> SEQUENCE: 22

Pro Pro Ser Val His Arg Phe Tyr Pro Val Pro Glu Ser Leu Ser Gln
1 5 10 15

Pro Ala Phe Gly Val Pro Ser Pro Ile Pro Pro Ser Thr Asn Ser Pro
20 25 30

Pro Met Glu Pro Asp Gly Val His Ala Glu Gln Gln Phe Ile Leu Asn
35 40 45

Gln Ile Ser Cys Ala Asn Thr Ala Leu Gln Arg Gln Arg Glu Glu Leu
50 55 60

Ala Ser Leu Val Met Leu His Ala Cys Lys Arg Gly Leu Phe Cys Pro
65 70 75 80

Val Lys Thr Tyr Lys Leu Ser Leu Asn Ala Ser Ala Ser Glu His Ser
85 90 95

Leu His Phe Glu Lys Ser Pro Ser Arg Phe Thr Leu Val Asn Thr His
100 105 110

Ala Gly Ala Ser Val Arg Val Ala Leu His His Gln Gly Ala Ser Gly
115 120 125

Ser Ile Arg Cys Ser Cys Ser His Ala Glu Cys Leu Pro Val Leu Leu
130 135 140

Lys Thr Leu Cys Ala Phe Asn Phe Leu Asp
145 150

<210> SEQ ID NO 23
<211> LENGTH: 5100
<212> TYPE: DNA
<213> ORGANISM: Bovine adenovirus type 3
<220> FEATURE:
<221> NAME/KEY: CDS -continued

<222> LOCATION: (1439)..(1702)

<400> SEQUENCE: 23

```
cctcatcaaa caacccgtgg tgggcaccac ccacgtggaa atgcctcgca acgaagtcct     60
agaacaacat ctgacctcac atggcgctca aatcgcgggc ggaggcgctg cgggcgatta    120
ctttaaaagc cccacttcag ctcgaaccct tatcccgctc accgcctcct gcttaagacc    180
agatggagtc tttcaactag gaggaggctc gcgttcatct ttcaaccccc tgcaaacaga    240
ttttgccttc cacgccctgc cctccagacc gcgccacggg ggcataggat ccaggcagtt    300
tgtagaggaa tttgtgcccg ccgtctacct caacccctac tcgggaccgc cggactctta    360
tccggaccag tttatacgcc actacaacgt gtacagcaac tctgtgagcg gttatagctg    420
agattgtaag actctcctat ctgtctctgt gctgcttttc cgcttcaagc cccacaagca    480
tgaaggggtt tctgctcatc ttcagcctgc ttgtgcattg tcccctaatt catgttggga    540
ccattagctt ctatgctgca aggcccgggt ctgagcctaa cgcgacttat gtttgtgact    600
atggaagcga gtcagattac aaccccacca cggttctgtg gttggctcga gagaccgatg    660
gctcctggat ctctgttctt ttccgtcaca acggctcctc aactgcagcc cccggggtcg    720
tcgcgcactt tactgaccac aacagcagca ttgtggtgcc ccagtattac ctcctcaaca    780
actcactctc taagctctgc tgctcatacc ggcacaacga gcgttctcag tttacctgca    840
aacaagctga cgtccctacc tgtcacgagc ccggcaagcc gctcaccctc cgcgtctccc    900
ccgcgctggg aactgcccac caagcagtca cttggttttt tcaaaatgta cccatagcta    960
ctgtttaccg accttggggc aatgtaactt ggttttgtcc tcccttcatg tgtaccttta   1020
atgtcagcct gaactcccta cttatttaca acttttctga caaaaccggg ggcaataca    1080
cagctctcat gcactccgga cctgcttccc tctttcagct ctttaagcca acgacttgtg   1140
tcaccaaggt ggaggacccg ccgtatgcca acgacccggc ctcgcctgtg tggcgcccac   1200
tgctttttgc cttcgtcctc tgcaccggct gcgcggtgtt gttaaccgcc ttcggtccat   1260
cgattctatc cggtacccga aagcttatct cagcccgctt ttggagtccc gagccctata   1320
ccaccctcca ctaacagtcc ccccatggag ccagacggag ttcatgccga gcagcagttt   1380
atcctcaatc agatttcctg cgccaacact gccctccagc gtcaaaggga ggaactag     1438

ctt ccc ttg tca tgt tgc atg cct gta agc gtg gcc tct ttt gtc cag     1486
Leu Pro Leu Ser Cys Cys Met Pro Val Ser Val Ala Ser Phe Val Gln
  1               5                  10                  15

tca aaa ctt aca agc tca gcc tca acg cct cgg cca gcg agc aca gcc     1534
Ser Lys Leu Thr Ser Ser Ala Ser Thr Pro Arg Pro Ala Ser Thr Ala
             20                  25                  30

tgc act ttg aaa aaa gtc cct ccc gat tca ccc tgg tca aca ctc acg     1582
Cys Thr Leu Lys Lys Val Pro Pro Asp Ser Pro Trp Ser Thr Leu Thr
         35                  40                  45

ccg gag ctt ctg tgc gag tgg ccc tac acc acc agg gag ctt ccg gca     1630
Pro Glu Leu Leu Cys Glu Trp Pro Tyr Thr Thr Arg Glu Leu Pro Ala
     50                  55                  60

gca tcc gct gtt cct gtt ccc acg ccg agt gcc tcc ccg tcc tcc tca     1678
Ala Ser Ala Val Pro Val Pro Thr Pro Ser Ala Ser Pro Ser Ser Ser
 65                  70                  75                  80

aga ccc tct gtg cct tta act ttt tagattagct gaaagcaaat ataaaatggt    1732
Arg Pro Ser Val Pro Leu Thr Phe
                 85

gtgcttaccg taattctgtt ttgacttgtg tgcttgattt ctccccctgc gccgtaatcc   1792

agtgcccctc ttcaaaactc tcgtacccta tgcgattcgc ataggcatat tttctaaaag   1852
```

-continued ctctgaagtc aacatcactc tcaaacactt ctccgttgta ggttactttc atctacagat 1912 aaagtcatcc accggttaac atcatgaaga gaagtgtgcc ccaggacttt aatcttgtgt 1972 atccgtacaa ggctaagagg cccaacatca tgccgccctt ttttgaccgc aatggctttg 2032 ttgaaaacca agaagccacg ctagccatgc ttgtggaaaa gccgctcacg ttcgacaagg 2092 aaggtgcgct gaccctgggc gtcggacgcg gcatccgcat taaccccgcg gggcttctgg 2152 agacaaacga cctcgcgtcc gctgtcttcc caccgctggc ctccgatgag gccggcaacg 2212 tcacgctcaa catgtctgac gggctatata ctaaggacaa caagctagct gtcaaagtag 2272 gtcccgggct gtccctcgac tccaataatg ctctccaggt ccacacaggc gacgggctca 2332 cggtaaccga tgacaaggtg tctctaaata cccaagctcc cctctcgacc accagcgcgg 2392 gcctctccct acttctgggt cccagcctcc acttaggtga ggaggaacga ctaacagtaa 2452 acaccggagc gggcctccaa attagcaata acgctctggc cgtaaaagta ggttcaggta 2512 tcaccgtaga tgctcaaaac cagctcgctg catccctggg ggacggtcta gaaagcagag 2572 ataataaaac tgtcgttaag gctgggcccg gacttacaat aactaatcaa gctcttactg 2632 ttgctaccgg gaacggcctt caggtcaacc cggaagggca actgcagcta aacattactg 2692 ccggtcaggg cctcaacttt gcaaacaaca gcctcgccgt ggagctgggc tcgggcctgc 2752 attttccccc tggccaaaac caagtaagcc tttatcccgg agatggaata gacatccgag 2812 ataatagggt gactgtgccc gctgggccag gcctgagaat gctcaaccac caacttgccg 2872 tagcttccgg agacggttta gaagtccaca gcgacaccct ccggttaaag ctctcccacg 2932 gcctgacatt tgaaaatggc gccgtacgag caaaactagg accaggactt ggcacagacg 2992 actctggtcg gtccgtggtt cgcacaggtc gaggacttag agttgcaaac ggccaagtcc 3052 agatcttcag cggaagaggc accgccatcg gcactgatag cagcctcact ctcaacatcc 3112 gggcgcccct acaattttct ggacccgcct tgactgctag tttgcaaggc agtggtccga 3172 ttacttacaa cagcaacaat ggcactttcg gtctctctat aggccccgga atgtgggtag 3232 accaaaacag acttcaggta aacccaggcg ctggtttagt cttccaagga aacaaccttg 3292 tcccaaacct tgcggatccg ctggctattt ccgacagcaa aattagtctc agtctcggtc 3352 ccggcctgac ccaagcttcc aacgccctga ctttaagttt aggaaacggg cttgaattct 3412 ccaatcaagc cgttgctata aaagcgggcc ggggcttacg ctttgagtct tcctcacaag 3472 ctttagagag cagcctcaca gtcggaaatg gcttaacgct taccgatact gtgatccgcc 3532 ccaacctagg ggacggccta gaggtcagag acaataaaat cattgttaag ctgggcgcga 3592 atcttcgttt tgaaaacgga gccgtaaccg ccggcaccgt taacccttct gcgcccgagg 3652 caccaccaac tctcactgca gaaccacccc tccgagcctc caactcccat cttcaactgt 3712 ccctatcgga gggcttggtt gtgcataaca acgcccttgc tctccaactg ggagacggca 3772 tggaagtaaa tcagcacgga cttactttaa gagtaggctc gggtttgcaa atgcgtgacg 3832 gcattttaac agttacaccc agcggcactc ctattgagcc cagactgact gccccactga 3892 ctcagacaga gaatggaatc gggctcgctc tcggcgccgg cttggaatta gacgagagcg 3952 cgctccaagt aaaagttggg cccggcatgc gcctgaaccc tgtagaaaag tatgtaaccc 4012 tgctcctggg tcctggcctt agttttgggc agccggccaa caggacaaat tatgatgtgc 4072 gcgtttctgt ggagcccccc atggttttcg gacagcgtgg tcagctcaca tttttagtgg 4132 gtcacggact acacattcaa aattccaaac ttcagctcaa tttgggacaa ggcctcagaa 4192

-continued

```
ctgaccccgt caccaaccag ctggaagtgc ccctcggtca aggtttggaa attgcagacg   4252

aatcccaggt tagggttaaa ttgggcgatg gcctgcagtt tgattcacaa gctcgcatca   4312

ctaccgctcc taacatggtc actgaaactc tgtggaccgg aacaggcagt aatgctaatg   4372

ttacatggcg gggctacact gcccccggca gcaaactctt tttgagtctc actcggttca   4432

gcactggtct agttttagga aacatgacta ttgacagcaa tgcatccttt gggcaataca   4492

ttaacgcggg acacgaacag atcgaatgct ttatattgtt ggacaatcag ggtaacctaa   4552

aagaaggatc taacttgcaa ggcacttggg aagtgaagaa caacccctct gcttccaaag   4612

ctgctttttt gccttccacc gccctatacc ccatcctcaa cgaaagccga gggagtcttc   4672

ctggaaaaaa tcttgtgggc atgcaagcca tactgggagg cgggggcact tgcactgtga   4732

tagccaccct caatggcaga cgcagcaaca actatcccgc gggccagtcc ataattttcg   4792

tgtggcaaga attcaacacc atagcccgcc aacctctgaa ccactctaca cttacttttt   4852

cttactggac ttaaataagt tggaaataaa gagttaaact gaatgtttaa gtgcaacaga   4912

cttttattgg ttttggctca caacaaatta caacagcata gacaagtcat accggtcaaa   4972

caacacaggc tctcgaaaac gggctaaccg ctccaagaat ctgtcacgca gacgagcaag   5032

tcctaaatgt tttttcactc tcttcggggc caagttcagc atgtatcgga ttttctgctt   5092

acaccttt                                                            5100
```

<210> SEQ ID NO 24
<211> LENGTH: 88
<212> TYPE: PRT
<213> ORGANISM: Bovine adenovirus type 3

<400> SEQUENCE: 24

```
Leu Pro Leu Ser Cys Cys Met Pro Val Ser Val Ala Ser Phe Val Gln
  1               5                  10                  15

Ser Lys Leu Thr Ser Ser Ala Ser Thr Pro Arg Pro Ala Ser Thr Ala
             20                  25                  30

Cys Thr Leu Lys Lys Val Pro Pro Asp Ser Pro Trp Ser Thr Leu Thr
         35                  40                  45

Pro Glu Leu Leu Cys Glu Trp Pro Tyr Thr Thr Arg Glu Leu Pro Ala
     50                  55                  60

Ala Ser Ala Val Pro Val Pro Thr Pro Ser Ala Ser Pro Ser Ser Ser
 65                  70                  75                  80

Arg Pro Ser Val Pro Leu Thr Phe
                 85
```

<210> SEQ ID NO 25
<211> LENGTH: 5100
<212> TYPE: DNA
<213> ORGANISM: Bovine adenovirus type 3
<220> FEATURE:
<221> NAME/KEY: CDS
<222> LOCATION: (1915)..(4863)

<400> SEQUENCE: 25

```
cctcatcaaa caacccgtgg tgggcaccac ccacgtggaa atgcctcgca acgaagtcct     60

agaacaacat ctgacctcac atggcgctca aatcgcgggc ggaggcgctg cgggcgatta    120

ctttaaaagc ccccacttcag ctcgaaccct tatcccgctc accgcctcct gcttaagacc    180

agatggagtc tttcaactag gaggaggctc gcgttcatct ttcaaccccc tgcaaacaga    240

ttttgccttc cacgccctgc cctccagacc gcgccacggg ggcataggat ccaggcagtt    300
```

-continued

```
tgtagaggaa tttgtgcccg ccgtctacct caacccctac tcgggaccgc cggactctta    360

tccggaccag tttatacgcc actacaacgt gtacagcaac tctgtgagcg gttatagctg    420

agattgtaag actctcctat ctgtctctgt gctgcttttc cgcttcaagc cccacaagca    480

tgaaggggtt tctgctcatc ttcagcctgc ttgtgcattg tcccctaatt catgttggga    540

ccattagctt ctatgctgca aggcccgggt ctgagcctaa cgcgacttat gtttgtgact    600

atggaagcga gtcagattac aaccccacca cggttctgtg gttggctcga gagaccgatg    660

gctcctggat ctctgttctt ttccgtcaca acggctcctc aactgcagcc cccggggtcg    720

tcgcgcactt tactgaccac aacagcagca ttgtggtgcc ccagtattac ctcctcaaca    780

actcactctc taagctctgc tgctcatacc ggcacaacga gcgttctcag tttacctgca    840

aacaagctga cgtccctacc tgtcacgagc ccggcaagcc gctcaccctc cgcgtctccc    900

ccgcgctggg aactgcccac caagcagtca cttggttttt tcaaaatgta cccatagcta    960

ctgtttaccg accttggggc aatgtaactt ggttttgtcc tcccttcatg tgtaccttta   1020

atgtcagcct gaactcccta cttatttaca acttttctga caaaaccggg gggcaataca   1080

cagctctcat gcactccgga cctgcttccc tctttcagct ctttaagcca acgacttgtg   1140

tcaccaaggt ggaggacccg ccgtatgcca acgacccggc ctcgcctgtg tggcgcccac   1200

tgctttttgc cttcgtcctc tgcaccggct gcgcggtgtt gttaaccgcc ttcggtccat   1260

cgattctatc cggtacccga aagcttatct cagcccgctt ttggagtccc gagccctata   1320

ccaccctcca ctaacagtcc ccccatggag ccagacggag ttcatgccga gcagcagttt   1380

atcctcaatc agatttcctg cgccaacact gccctccagc gtcaaaggga ggaactagct   1440

tcccttgtca tgttgcatgc ctgtaagcgt ggcctctttt gtccagtcaa aacttacaag   1500

ctcagcctca acgcctcggc cagcgagcac agcctgcact ttgaaaaaag tccctcccga   1560

ttcaccctgg tcaacactca cgccggagct tctgtgcgag tggccctaca ccaccaggga   1620

gcttccggca gcatccgctg ttcctgttcc cacgccgagt gcctccccgt cctcctcaag   1680

accctctgtg cctttaactt tttagattag ctgaaagcaa atataaaatg gtgtgcttac   1740

cgtaattctg ttttgacttg tgtgcttgat ttctccccct gcgccgtaat ccagtgcccc   1800

tcttcaaaac tctcgtaccc tatgcgattc gcataggcat atttctaaa agctctgaag   1860

tcaacatcac tctcaaacac ttctccgttg taggttactt tcatctacag ataa agt     1917
                                                            Ser
                                                              1

cat cca ccg gtt aac atc atg aag aga agt gtg ccc cag gac ttt aat     1965
His Pro Pro Val Asn Ile Met Lys Arg Ser Val Pro Gln Asp Phe Asn
            5                   10                  15

ctt gtg tat ccg tac aag gct aag agg ccc aac atc atg ccg ccc ttt     2013
Leu Val Tyr Pro Tyr Lys Ala Lys Arg Pro Asn Ile Met Pro Pro Phe
        20                  25                  30

ttt gac cgc aat ggc ttt gtt gaa aac caa gaa gcc acg cta gcc atg     2061
Phe Asp Arg Asn Gly Phe Val Glu Asn Gln Glu Ala Thr Leu Ala Met
    35                  40                  45

ctt gtg gaa aag ccg ctc acg ttc gac aag gaa ggt gcg ctg acc ctg     2109
Leu Val Glu Lys Pro Leu Thr Phe Asp Lys Glu Gly Ala Leu Thr Leu
 50                 55                  60                  65

ggc gtc gga cgc ggc atc cgc att aac ccc gcg ggg ctt ctg gag aca     2157
Gly Val Gly Arg Gly Ile Arg Ile Asn Pro Ala Gly Leu Leu Glu Thr
                70                  75                  80

aac gac ctc gcg tcc gct gtc ttc cca ccg ctg gcc tcc gat gag gcc     2205
Asn Asp Leu Ala Ser Ala Val Phe Pro Pro Leu Ala Ser Asp Glu Ala
            85                  90                  95
```

-continued

```
ggc aac gtc acg ctc aac atg tct gac ggg cta tat act aag gac aac     2253
Gly Asn Val Thr Leu Asn Met Ser Asp Gly Leu Tyr Thr Lys Asp Asn
        100                 105                 110

aag cta gct gtc aaa gta ggt ccc ggg ctg tcc ctc gac tcc aat aat     2301
Lys Leu Ala Val Lys Val Gly Pro Gly Leu Ser Leu Asp Ser Asn Asn
    115                 120                 125

gct ctc cag gtc cac aca ggc gac ggg ctc acg gta acc gat gac aag     2349
Ala Leu Gln Val His Thr Gly Asp Gly Leu Thr Val Thr Asp Asp Lys
130                 135                 140                 145

gtg tct cta aat acc caa gct ccc ctc tcg acc acc agc gcg ggc ctc     2397
Val Ser Leu Asn Thr Gln Ala Pro Leu Ser Thr Thr Ser Ala Gly Leu
                150                 155                 160

tcc cta ctt ctg ggt ccc agc ctc cac tta ggt gag gag gaa cga cta     2445
Ser Leu Leu Leu Gly Pro Ser Leu His Leu Gly Glu Glu Glu Arg Leu
            165                 170                 175

aca gta aac acc gga gcg ggc ctc caa att agc aat aac gct ctg gcc     2493
Thr Val Asn Thr Gly Ala Gly Leu Gln Ile Ser Asn Asn Ala Leu Ala
        180                 185                 190

gta aaa gta ggt tca ggt atc acc gta gat gct caa aac cag ctc gct     2541
Val Lys Val Gly Ser Gly Ile Thr Val Asp Ala Gln Asn Gln Leu Ala
    195                 200                 205

gca tcc ctg ggg gac ggt cta gaa agc aga gat aat aaa act gtc gtt     2589
Ala Ser Leu Gly Asp Gly Leu Glu Ser Arg Asp Asn Lys Thr Val Val
210                 215                 220                 225

aag gct ggg ccc gga ctt aca ata act aat caa gct ctt act gtt gct     2637
Lys Ala Gly Pro Gly Leu Thr Ile Thr Asn Gln Ala Leu Thr Val Ala
                230                 235                 240

acc ggg aac ggc ctt cag gtc aac ccg gaa ggg caa ctg cag cta aac     2685
Thr Gly Asn Gly Leu Gln Val Asn Pro Glu Gly Gln Leu Gln Leu Asn
            245                 250                 255

att act gcc ggt cag ggc ctc aac ttt gca aac aac agc ctc gcc gtg     2733
Ile Thr Ala Gly Gln Gly Leu Asn Phe Ala Asn Asn Ser Leu Ala Val
        260                 265                 270

gag ctg ggc tcg ggc ctg cat ttt ccc cct ggc caa aac caa gta agc     2781
Glu Leu Gly Ser Gly Leu His Phe Pro Pro Gly Gln Asn Gln Val Ser
    275                 280                 285

ctt tat ccc gga gat gga ata gac atc cga gat aat agg gtg act gtg     2829
Leu Tyr Pro Gly Asp Gly Ile Asp Ile Arg Asp Asn Arg Val Thr Val
290                 295                 300                 305

ccc gct ggg cca ggc ctg aga atg ctc aac cac caa ctt gcc gta gct     2877
Pro Ala Gly Pro Gly Leu Arg Met Leu Asn His Gln Leu Ala Val Ala
                310                 315                 320

tcc gga gac ggt tta gaa gtc cac agc gac acc ctc cgg tta aag ctc     2925
Ser Gly Asp Gly Leu Glu Val His Ser Asp Thr Leu Arg Leu Lys Leu
            325                 330                 335

tcc cac ggc ctg aca ttt gaa aat ggc gcc gta cga gca aaa cta gga     2973
Ser His Gly Leu Thr Phe Glu Asn Gly Ala Val Arg Ala Lys Leu Gly
        340                 345                 350

cca gga ctt ggc aca gac gac tct ggt cgg tcc gtg gtt cgc aca ggt     3021
Pro Gly Leu Gly Thr Asp Asp Ser Gly Arg Ser Val Val Arg Thr Gly
    355                 360                 365

cga gga ctt aga gtt gca aac ggc caa gtc cag atc ttc agc gga aga     3069
Arg Gly Leu Arg Val Ala Asn Gly Gln Val Gln Ile Phe Ser Gly Arg
370                 375                 380                 385

ggc acc gcc atc ggc act gat agc agc ctc act ctc aac atc cgg gcg     3117
Gly Thr Ala Ile Gly Thr Asp Ser Ser Leu Thr Leu Asn Ile Arg Ala
                390                 395                 400
```

-continued

```
ccc cta caa ttt tct gga ccc gcc ttg act gct agt ttg caa ggc agt      3165
Pro Leu Gln Phe Ser Gly Pro Ala Leu Thr Ala Ser Leu Gln Gly Ser
            405                 410                 415

ggt ccg att act tac aac agc aac aat ggc act ttc ggt ctc tct ata      3213
Gly Pro Ile Thr Tyr Asn Ser Asn Asn Gly Thr Phe Gly Leu Ser Ile
        420                 425                 430

ggc ccc gga atg tgg gta gac caa aac aga ctt cag gta aac cca ggc      3261
Gly Pro Gly Met Trp Val Asp Gln Asn Arg Leu Gln Val Asn Pro Gly
    435                 440                 445

gct ggt tta gtc ttc caa gga aac aac ctt gtc cca aac ctt gcg gat      3309
Ala Gly Leu Val Phe Gln Gly Asn Asn Leu Val Pro Asn Leu Ala Asp
450                 455                 460                 465

ccg ctg gct att tcc gac agc aaa att agt ctc agt ctc ggt ccc ggc      3357
Pro Leu Ala Ile Ser Asp Ser Lys Ile Ser Leu Ser Leu Gly Pro Gly
                470                 475                 480

ctg acc caa gct tcc aac gcc ctg act tta agt tta gga aac ggg ctt      3405
Leu Thr Gln Ala Ser Asn Ala Leu Thr Leu Ser Leu Gly Asn Gly Leu
            485                 490                 495

gaa ttc tcc aat caa gcc gtt gct ata aaa gcg ggc cgg ggc tta cgc      3453
Glu Phe Ser Asn Gln Ala Val Ala Ile Lys Ala Gly Arg Gly Leu Arg
        500                 505                 510

ttt gag tct tcc tca caa gct tta gag agc agc ctc aca gtc gga aat      3501
Phe Glu Ser Ser Ser Gln Ala Leu Glu Ser Ser Leu Thr Val Gly Asn
    515                 520                 525

ggc tta acg ctt acc gat act gtg atc cgc ccc aac cta ggg gac ggc      3549
Gly Leu Thr Leu Thr Asp Thr Val Ile Arg Pro Asn Leu Gly Asp Gly
530                 535                 540                 545

cta gag gtc aga gac aat aaa atc att gtt aag ctg ggc gcg aat ctt      3597
Leu Glu Val Arg Asp Asn Lys Ile Ile Val Lys Leu Gly Ala Asn Leu
                550                 555                 560

cgt ttt gaa aac gga gcc gta acc gcc ggc acc gtt aac cct tct gcg      3645
Arg Phe Glu Asn Gly Ala Val Thr Ala Gly Thr Val Asn Pro Ser Ala
            565                 570                 575

ccc gag gca cca cca act ctc act gca gaa cca ccc ctc cga gcc tcc      3693
Pro Glu Ala Pro Pro Thr Leu Thr Ala Glu Pro Pro Leu Arg Ala Ser
        580                 585                 590

aac tcc cat ctt caa ctg tcc cta tcg gag ggc ttg gtt gtg cat aac      3741
Asn Ser His Leu Gln Leu Ser Leu Ser Glu Gly Leu Val Val His Asn
    595                 600                 605

aac gcc ctt gct ctc caa ctg gga gac ggc atg gaa gta aat cag cac      3789
Asn Ala Leu Ala Leu Gln Leu Gly Asp Gly Met Glu Val Asn Gln His
610                 615                 620                 625

gga ctt act tta aga gta ggc tcg ggt ttg caa atg cgt gac ggc att      3837
Gly Leu Thr Leu Arg Val Gly Ser Gly Leu Gln Met Arg Asp Gly Ile
                630                 635                 640

tta aca gtt aca ccc agc ggc act cct att gag ccc aga ctg act gcc      3885
Leu Thr Val Thr Pro Ser Gly Thr Pro Ile Glu Pro Arg Leu Thr Ala
            645                 650                 655

cca ctg act cag aca gag aat gga atc ggg ctc gct ctc ggc gcc ggc      3933
Pro Leu Thr Gln Thr Glu Asn Gly Ile Gly Leu Ala Leu Gly Ala Gly
        660                 665                 670

ttg gaa tta gac gag agc gcg ctc caa gta aaa gtt ggg ccc ggc atg      3981
Leu Glu Leu Asp Glu Ser Ala Leu Gln Val Lys Val Gly Pro Gly Met
    675                 680                 685

cgc ctg aac cct gta gaa aag tat gta acc ctg ctc ctg ggt cct ggc      4029
Arg Leu Asn Pro Val Glu Lys Tyr Val Thr Leu Leu Leu Gly Pro Gly
690                 695                 700                 705

ctt agt ttt ggg cag ccg gcc aac agg aca aat tat gat gtg cgc gtt      4077
Leu Ser Phe Gly Gln Pro Ala Asn Arg Thr Asn Tyr Asp Val Arg Val
                710                 715                 720
```

-continued

```
tct gtg gag ccc ccc atg gtt ttc gga cag cgt ggt cag ctc aca ttt     4125
Ser Val Glu Pro Pro Met Val Phe Gly Gln Arg Gly Gln Leu Thr Phe
            725                 730                 735

tta gtg ggt cac gga cta cac att caa aat tcc aaa ctt cag ctc aat     4173
Leu Val Gly His Gly Leu His Ile Gln Asn Ser Lys Leu Gln Leu Asn
        740                 745                 750

ttg gga caa ggc ctc aga act gac ccc gtc acc aac cag ctg gaa gtg     4221
Leu Gly Gln Gly Leu Arg Thr Asp Pro Val Thr Asn Gln Leu Glu Val
    755                 760                 765

ccc ctc ggt caa ggt ttg gaa att gca gac gaa tcc cag gtt agg gtt     4269
Pro Leu Gly Gln Gly Leu Glu Ile Ala Asp Glu Ser Gln Val Arg Val
770                 775                 780                 785

aaa ttg ggc gat ggc ctg cag ttt gat tca caa gct cgc atc act acc     4317
Lys Leu Gly Asp Gly Leu Gln Phe Asp Ser Gln Ala Arg Ile Thr Thr
                790                 795                 800

gct cct aac atg gtc act gaa act ctg tgg acc gga aca ggc agt aat     4365
Ala Pro Asn Met Val Thr Glu Thr Leu Trp Thr Gly Thr Gly Ser Asn
            805                 810                 815

gct aat gtt aca tgg cgg ggc tac act gcc ccc ggc agc aaa ctc ttt     4413
Ala Asn Val Thr Trp Arg Gly Tyr Thr Ala Pro Gly Ser Lys Leu Phe
        820                 825                 830

ttg agt ctc act cgg ttc agc act ggt cta gtt tta gga aac atg act     4461
Leu Ser Leu Thr Arg Phe Ser Thr Gly Leu Val Leu Gly Asn Met Thr
    835                 840                 845

att gac agc aat gca tcc ttt ggg caa tac att aac gcg gga cac gaa     4509
Ile Asp Ser Asn Ala Ser Phe Gly Gln Tyr Ile Asn Ala Gly His Glu
850                 855                 860                 865

cag atc gaa tgc ttt ata ttg ttg gac aat cag ggt aac cta aaa gaa     4557
Gln Ile Glu Cys Phe Ile Leu Leu Asp Asn Gln Gly Asn Leu Lys Glu
                870                 875                 880

gga tct aac ttg caa ggc act tgg gaa gtg aag aac aac ccc tct gct     4605
Gly Ser Asn Leu Gln Gly Thr Trp Glu Val Lys Asn Asn Pro Ser Ala
            885                 890                 895

tcc aaa gct gct ttt ttg cct tcc acc gcc cta tac ccc atc ctc aac     4653
Ser Lys Ala Ala Phe Leu Pro Ser Thr Ala Leu Tyr Pro Ile Leu Asn
        900                 905                 910

gaa agc cga ggg agt ctt cct gga aaa aat ctt gtg ggc atg caa gcc     4701
Glu Ser Arg Gly Ser Leu Pro Gly Lys Asn Leu Val Gly Met Gln Ala
    915                 920                 925

ata ctg gga ggc ggg ggc act tgc act gtg ata gcc acc ctc aat ggc     4749
Ile Leu Gly Gly Gly Gly Thr Cys Thr Val Ile Ala Thr Leu Asn Gly
930                 935                 940                 945

aga cgc agc aac aac tat ccc gcg ggc cag tcc ata att ttc gtg tgg     4797
Arg Arg Ser Asn Asn Tyr Pro Ala Gly Gln Ser Ile Ile Phe Val Trp
                950                 955                 960

caa gaa ttc aac acc ata gcc cgc caa cct ctg aac cac tct aca ctt     4845
Gln Glu Phe Asn Thr Ile Ala Arg Gln Pro Leu Asn His Ser Thr Leu
            965                 970                 975

act ttt tct tac tgg act taaataagtt ggaaataaag agttaaactg            4893
Thr Phe Ser Tyr Trp Thr
        980

aatgtttaag tgcaacagac ttttattggt tttggctcac aacaaattac aacagcatag   4953

acaagtcata ccggtcaaac aacacaggct ctcgaaaacg ggctaaccgc tccaagaatc   5013

tgtcacgcag acgagcaagt cctaaatgtt ttttcactct cttcggggcc aagttcagca   5073

tgtatcggat tttctgctta cacctttt                                      5100
```

-continued

<210> SEQ ID NO 26
<211> LENGTH: 983
<212> TYPE: PRT
<213> ORGANISM: Bovine adenovirus type 3

<400> SEQUENCE: 26

```
Ser His Pro Pro Val Asn Ile Met Lys Arg Ser Val Pro Gln Asp Phe
  1               5                  10                  15

Asn Leu Val Tyr Pro Tyr Lys Ala Lys Arg Pro Asn Ile Met Pro Pro
             20                  25                  30

Phe Phe Asp Arg Asn Gly Phe Val Glu Asn Gln Glu Ala Thr Leu Ala
         35                  40                  45

Met Leu Val Glu Lys Pro Leu Thr Phe Asp Lys Glu Gly Ala Leu Thr
     50                  55                  60

Leu Gly Val Gly Arg Gly Ile Arg Ile Asn Pro Ala Gly Leu Leu Glu
 65                  70                  75                  80

Thr Asn Asp Leu Ala Ser Ala Val Phe Pro Pro Leu Ala Ser Asp Glu
                 85                  90                  95

Ala Gly Asn Val Thr Leu Asn Met Ser Asp Gly Leu Tyr Thr Lys Asp
            100                 105                 110

Asn Lys Leu Ala Val Lys Val Gly Pro Gly Leu Ser Leu Asp Ser Asn
        115                 120                 125

Asn Ala Leu Gln Val His Thr Gly Asp Gly Leu Thr Val Thr Asp Asp
    130                 135                 140

Lys Val Ser Leu Asn Thr Gln Ala Pro Leu Ser Thr Thr Ser Ala Gly
145                 150                 155                 160

Leu Ser Leu Leu Leu Gly Pro Ser Leu His Leu Gly Glu Glu Glu Arg
                165                 170                 175

Leu Thr Val Asn Thr Gly Ala Gly Leu Gln Ile Ser Asn Asn Ala Leu
            180                 185                 190

Ala Val Lys Val Gly Ser Gly Ile Thr Val Asp Ala Gln Asn Gln Leu
        195                 200                 205

Ala Ala Ser Leu Gly Asp Gly Leu Glu Ser Arg Asp Asn Lys Thr Val
    210                 215                 220

Val Lys Ala Gly Pro Gly Leu Thr Ile Thr Asn Gln Ala Leu Thr Val
225                 230                 235                 240

Ala Thr Gly Asn Gly Leu Gln Val Asn Pro Glu Gly Gln Leu Gln Leu
                245                 250                 255

Asn Ile Thr Ala Gly Gln Gly Leu Asn Phe Ala Asn Asn Ser Leu Ala
            260                 265                 270

Val Glu Leu Gly Ser Gly Leu His Phe Pro Pro Gly Gln Asn Gln Val
        275                 280                 285

Ser Leu Tyr Pro Gly Asp Gly Ile Asp Ile Arg Asp Asn Arg Val Thr
    290                 295                 300

Val Pro Ala Gly Pro Gly Leu Arg Met Leu Asn His Gln Leu Ala Val
305                 310                 315                 320

Ala Ser Gly Asp Gly Leu Glu Val His Ser Asp Thr Leu Arg Leu Lys
                325                 330                 335

Leu Ser His Gly Leu Thr Phe Glu Asn Gly Ala Val Arg Ala Lys Leu
            340                 345                 350

Gly Pro Gly Leu Gly Thr Asp Asp Ser Gly Arg Ser Val Val Arg Thr
        355                 360                 365

Gly Arg Gly Leu Arg Val Ala Asn Gly Gln Val Gln Ile Phe Ser Gly
    370                 375                 380
```

-continued

```
Arg Gly Thr Ala Ile Gly Thr Asp Ser Ser Leu Thr Leu Asn Ile Arg
385                 390                 395                 400

Ala Pro Leu Gln Phe Ser Gly Pro Ala Leu Thr Ala Ser Leu Gln Gly
                405                 410                 415

Ser Gly Pro Ile Thr Tyr Asn Ser Asn Asn Gly Thr Phe Gly Leu Ser
            420                 425                 430

Ile Gly Pro Gly Met Trp Val Asp Gln Asn Arg Leu Gln Val Asn Pro
        435                 440                 445

Gly Ala Gly Leu Val Phe Gln Gly Asn Asn Leu Val Pro Asn Leu Ala
    450                 455                 460

Asp Pro Leu Ala Ile Ser Asp Ser Lys Ile Ser Leu Ser Leu Gly Pro
465                 470                 475                 480

Gly Leu Thr Gln Ala Ser Asn Ala Leu Thr Leu Ser Leu Gly Asn Gly
                485                 490                 495

Leu Glu Phe Ser Asn Gln Ala Val Ala Ile Lys Ala Gly Arg Gly Leu
            500                 505                 510

Arg Phe Glu Ser Ser Ser Gln Ala Leu Glu Ser Ser Leu Thr Val Gly
        515                 520                 525

Asn Gly Leu Thr Leu Thr Asp Thr Val Ile Arg Pro Asn Leu Gly Asp
    530                 535                 540

Gly Leu Glu Val Arg Asp Asn Lys Ile Ile Val Lys Leu Gly Ala Asn
545                 550                 555                 560

Leu Arg Phe Glu Asn Gly Ala Val Thr Ala Gly Thr Val Asn Pro Ser
                565                 570                 575

Ala Pro Glu Ala Pro Pro Thr Leu Thr Ala Glu Pro Pro Leu Arg Ala
            580                 585                 590

Ser Asn Ser His Leu Gln Leu Ser Leu Ser Glu Gly Leu Val Val His
        595                 600                 605

Asn Asn Ala Leu Ala Leu Gln Leu Gly Asp Gly Met Glu Val Asn Gln
    610                 615                 620

His Gly Leu Thr Leu Arg Val Gly Ser Gly Leu Gln Met Arg Asp Gly
625                 630                 635                 640

Ile Leu Thr Val Thr Pro Ser Gly Thr Pro Ile Glu Pro Arg Leu Thr
                645                 650                 655

Ala Pro Leu Thr Gln Thr Glu Asn Gly Ile Gly Leu Ala Leu Gly Ala
            660                 665                 670

Gly Leu Glu Leu Asp Glu Ser Ala Leu Gln Val Lys Val Gly Pro Gly
        675                 680                 685

Met Arg Leu Asn Pro Val Glu Lys Tyr Val Thr Leu Leu Leu Gly Pro
    690                 695                 700

Gly Leu Ser Phe Gly Gln Pro Ala Asn Arg Thr Asn Tyr Asp Val Arg
705                 710                 715                 720

Val Ser Val Glu Pro Pro Met Val Phe Gly Gln Arg Gly Gln Leu Thr
                725                 730                 735

Phe Leu Val Gly His Gly Leu His Ile Gln Asn Ser Lys Leu Gln Leu
            740                 745                 750

Asn Leu Gly Gln Gly Leu Arg Thr Asp Pro Val Thr Asn Gln Leu Glu
        755                 760                 765

Val Pro Leu Gly Gln Gly Leu Glu Ile Ala Asp Glu Ser Gln Val Arg
    770                 775                 780

Val Lys Leu Gly Asp Gly Leu Gln Phe Asp Ser Gln Ala Arg Ile Thr
785                 790                 795                 800
```

-continued

```
Thr Ala Pro Asn Met Val Thr Glu Thr Leu Trp Thr Gly Thr Gly Ser
                805                 810                 815

Asn Ala Asn Val Thr Trp Arg Gly Tyr Thr Ala Pro Gly Ser Lys Leu
            820                 825                 830

Phe Leu Ser Leu Thr Arg Phe Ser Thr Gly Leu Val Leu Gly Asn Met
        835                 840                 845

Thr Ile Asp Ser Asn Ala Ser Phe Gly Gln Tyr Ile Asn Ala Gly His
    850                 855                 860

Glu Gln Ile Glu Cys Phe Ile Leu Leu Asp Asn Gln Gly Asn Leu Lys
865                 870                 875                 880

Glu Gly Ser Asn Leu Gln Gly Thr Trp Glu Val Lys Asn Asn Pro Ser
                885                 890                 895

Ala Ser Lys Ala Ala Phe Leu Pro Ser Thr Ala Leu Tyr Pro Ile Leu
            900                 905                 910

Asn Glu Ser Arg Gly Ser Leu Pro Gly Lys Asn Leu Val Gly Met Gln
        915                 920                 925

Ala Ile Leu Gly Gly Gly Gly Thr Cys Thr Val Ile Ala Thr Leu Asn
    930                 935                 940

Gly Arg Arg Ser Asn Asn Tyr Pro Ala Gly Gln Ser Ile Ile Phe Val
945                 950                 955                 960

Trp Gln Glu Phe Asn Thr Ile Ala Arg Gln Pro Leu Asn His Ser Thr
                965                 970                 975

Leu Thr Phe Ser Tyr Trp Thr
            980


<210> SEQ ID NO 27
<211> LENGTH: 227
<212> TYPE: PRT
<213> ORGANISM: Human adenovirus type 2

<400> SEQUENCE: 27

Met Ser Lys Glu Ile Pro Thr Pro Tyr Met Trp Ser Tyr Gln Pro Gln
  1               5                  10                  15

Met Gly Leu Ala Ala Gly Ala Ala Gln Asp Tyr Ser Thr Arg Ile Asn
             20                  25                  30

Tyr Met Ser Ala Gly Pro His Met Ile Ser Arg Val Asn Gly Ile Arg
         35                  40                  45

Ala His Arg Asn Arg Ile Leu Leu Glu Gln Ala Ala Ile Thr Thr Thr
     50                  55                  60

Pro Arg Asn Asn Leu Asn Pro Arg Ser Trp Pro Ala Ala Leu Val Tyr
 65                  70                  75                  80

Gln Glu Ser Pro Ala Pro Thr Thr Val Val Leu Pro Arg Asp Ala Gln
                 85                  90                  95

Ala Glu Val Gln Met Thr Asn Ser Gly Ala Gln Leu Ala Gly Gly Phe
            100                 105                 110

Arg His Arg Val Arg Ser Pro Gly Gln Gly Ile Thr His Leu Lys Ile
        115                 120                 125

Arg Gly Arg Gly Ile Gln Leu Asn Asp Glu Ser Val Ser Ser Ser Leu
    130                 135                 140

Gly Leu Arg Pro Asp Gly Thr Phe Gln Ile Gly Gly Ala Gly Arg Ser
145                 150                 155                 160

Ser Phe Thr Pro Arg Gln Ala Ile Leu Thr Leu Gln Thr Ser Ser Ser
                165                 170                 175

Glu Pro Arg Ser Gly Gly Ile Gly Thr Leu Gln Phe Ile Glu Glu Phe
            180                 185                 190
```

-continued

```
Val Pro Ser Val Tyr Phe Asn Pro Phe Ser Gly Pro Pro Gly His Tyr
        195                 200                 205

Pro Asp Gln Phe Ile Pro Asn Phe Asp Ala Val Lys Asp Ser Ala Asp
    210                 215                 220

Gly Tyr Asp
225


<210> SEQ ID NO 28
<211> LENGTH: 128
<212> TYPE: PRT
<213> ORGANISM: Human adenovirus type 5

<400> SEQUENCE: 28

Met Thr Asp Thr Leu Asp Leu Glu Met Asp Gly Ile Ile Thr Glu Gln
  1               5                  10                  15

Arg Leu Leu Glu Arg Arg Arg Ala Ala Ala Glu Gln Gln Arg Met Asn
             20                  25                  30

Gln Glu Leu Gln Asp Met Val Asn Leu His Gln Cys Lys Arg Gly Ile
         35                  40                  45

Phe Cys Leu Val Lys Gln Ala Lys Val Thr Tyr Asp Ser Asn Thr Thr
     50                  55                  60

Gly His Arg Leu Ser Tyr Lys Leu Pro Thr Lys Arg Gln Lys Leu Val
 65                  70                  75                  80

Val Met Val Gly Glu Lys Pro Ile Thr Ile Thr Gln His Ser Val Glu
                 85                  90                  95

Thr Glu Gly Cys Ile His Ser Pro Cys Gln Gly Pro Glu Asp Leu Cys
            100                 105                 110

Thr Leu Ile Lys Thr Leu Cys Gly Leu Lys Asp Leu Ile Pro Phe Asn
        115                 120                 125


<210> SEQ ID NO 29
<211> LENGTH: 582
<212> TYPE: PRT
<213> ORGANISM: Human adenovirus type 2

<400> SEQUENCE: 29

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
             20                  25                  30

Phe Val Ser Pro Asn Gly Phe Gln Glu Ser Pro Pro Gly Val Leu Ser
         35                  40                  45

Leu Arg Val Ser Glu Pro Leu Asp Thr Ser His Gly Met Leu Ala Leu
     50                  55                  60

Lys Met Gly Ser Gly Leu Thr Leu Asp Lys Ala Gly Asn Leu Thr Ser
 65                  70                  75                  80

Gln Asn Val Thr Thr Val Thr Gln Pro Leu Lys Lys Thr Lys Ser Asn
                 85                  90                  95

Ile Ser Leu Asp Thr Ser Ala Pro Leu Thr Ile Thr Ser Gly Ala Leu
            100                 105                 110

Thr Val Ala Thr Thr Ala Pro Leu Ile Val Thr Ser Gly Ala Leu Ser
        115                 120                 125

Val Gln Ser Gln Ala Pro Leu Thr Val Gln Asp Ser Lys Leu Ser Ile
    130                 135                 140

Ala Thr Lys Gly Pro Ile Thr Val Ser Asp Gly Lys Leu Ala Leu Gln
145                 150                 155                 160
```

-continued

```
Thr Ser Ala Pro Leu Ser Gly Ser Asp Ser Asp Thr Leu Thr Val Thr
                165                 170                 175

Ala Ser Pro Pro Leu Thr Thr Ala Thr Gly Ser Leu Gly Ile Asn Met
            180                 185                 190

Glu Asp Pro Ile Tyr Val Asn Asn Gly Lys Ile Gly Ile Lys Ile Ser
        195                 200                 205

Gly Pro Leu Gln Val Ala Gln Asn Ser Asp Thr Leu Thr Val Val Thr
    210                 215                 220

Gly Pro Gly Val Thr Val Glu Gln Asn Ser Leu Arg Thr Lys Val Ala
225                 230                 235                 240

Gly Ala Ile Gly Tyr Asp Ser Ser Asn Asn Met Glu Ile Lys Thr Gly
                245                 250                 255

Gly Gly Met Arg Ile Asn Asn Asn Leu Leu Ile Leu Asp Val Asp Tyr
            260                 265                 270

Pro Phe Asp Ala Gln Thr Lys Leu Arg Leu Lys Leu Gly Gln Gly Pro
        275                 280                 285

Leu Tyr Ile Asn Ala Ser His Asn Leu Asp Ile Asn Tyr Asn Arg Gly
    290                 295                 300

Leu Tyr Leu Phe Asn Ala Ser Asn Asn Thr Lys Lys Leu Glu Val Ser
305                 310                 315                 320

Ile Lys Lys Ser Ser Gly Leu Asn Phe Asp Asn Thr Ala Ile Ala Ile
                325                 330                 335

Asn Ala Gly Lys Gly Leu Glu Phe Asp Thr Asn Thr Ser Glu Ser Pro
            340                 345                 350

Asp Ile Asn Pro Ile Lys Thr Lys Ile Gly Ser Gly Ile Asp Tyr Asn
        355                 360                 365

Glu Asn Gly Ala Met Ile Thr Lys Leu Gly Ala Gly Leu Ser Phe Asp
    370                 375                 380

Asn Ser Gly Ala Ile Thr Ile Gly Asn Lys Asn Asp Asp Lys Leu Thr
385                 390                 395                 400

Leu Trp Thr Thr Pro Asp Pro Ser Pro Asn Cys Arg Ile His Ser Asp
                405                 410                 415

Asn Asp Cys Lys Phe Thr Leu Val Leu Thr Lys Cys Gly Ser Gln Val
            420                 425                 430

Leu Ala Thr Val Ala Ala Leu Ala Val Ser Gly Asp Leu Ser Ser Met
        435                 440                 445

Thr Gly Thr Val Ala Ser Val Ser Ile Phe Leu Arg Phe Asp Gln Asn
    450                 455                 460

Gly Val Leu Met Glu Asn Ser Ser Leu Lys Lys His Tyr Trp Asn Phe
465                 470                 475                 480

Arg Asn Gly Asn Ser Thr Asn Ala Asn Pro Tyr Thr Asn Ala Val Gly
                485                 490                 495

Phe Met Pro Asn Leu Leu Ala Tyr Pro Lys Thr Gln Ser Gln Thr Ala
            500                 505                 510

Lys Asn Asn Ile Val Ser Gln Val Tyr Leu His Gly Asp Lys Thr Lys
        515                 520                 525

Pro Met Ile Leu Thr Ile Thr Leu Asn Gly Thr Ser Glu Ser Thr Glu
    530                 535                 540

Thr Ser Glu Val Ser Thr Tyr Ser Met Ser Phe Thr Trp Ser Trp Glu
545                 550                 555                 560
```

-continued

```
Ser Gly Lys Tyr Thr Thr Glu Thr Phe Ala Thr Asn Ser Tyr Thr Phe
                565                 570                 575

Ser Tyr Ile Ala Gln Glu
            580


<210> SEQ ID NO 30
<211> LENGTH: 21
<212> TYPE: PRT
<213> ORGANISM: Artificial
<220> FEATURE:
<221> NAME/KEY: Modified-sites
<222> LOCATION: 2, 3, 5-17, 19-20
<223> OTHER INFORMATION: Xaa can be any amino acid; consensus
      metal-binding sequence

<400> SEQUENCE: 30

Cys Xaa Xaa Cys Xaa Xaa Xaa Xaa Xaa Xaa Xaa Xaa Xaa Xaa Xaa Xaa
  1               5                  10                  15

Xaa Cys Xaa Xaa Cys
             20


<210> SEQ ID NO 31
<211> LENGTH: 7
<212> TYPE: PRT
<213> ORGANISM: Bovine adenovirus type 3; human adenovirus type 5
<220> FEATURE:
<221> NAME/KEY: Modified-site
<222> LOCATION: (4)
<223> OTHER INFORMATION: Xaa can be any amino acid; region of homology

<400> SEQUENCE: 31

Gln Ser Ser Xaa Ser Thr Ser
  1               5


<210> SEQ ID NO 32
<211> LENGTH: 27
<212> TYPE: PRT
<213> ORGANISM: Bovine adenovirus type 3

<400> SEQUENCE: 32

Pro Leu Leu Phe Ala Phe Val Leu Cys Thr Gly Cys Ala Val Leu Leu
  1               5                  10                  15

Thr Ala Phe Gly Pro Ser Ile Leu Ser Gly Thr
             20                  25


<210> SEQ ID NO 33
<211> LENGTH: 57
<212> TYPE: PRT
<213> ORGANISM: Bovine adenovirus type 3

<400> SEQUENCE: 33

Glu Glu Val Thr Ser His Phe Phe Leu Asp Cys Pro Glu Asp Pro Ser
  1               5                  10                  15

Arg Glu Cys Ser Ser Cys Gly Phe His Gln Ala Gln Ser Gly Ile Pro
             20                  25                  30

Gly Ile Met Cys Ser Leu Cys Tyr Met Arg Gln Thr Tyr His Cys Ile
         35                  40                  45

Tyr Ser Pro Val Ser Glu Glu Glu Met
     50                  55


<210> SEQ ID NO 34
<211> LENGTH: 12
<212> TYPE: PRT
```

-continued

```
<213> ORGANISM: Bovine adenovirus type 3

<400> SEQUENCE: 34

Val Asp Leu Glu Cys His Glu Val Leu Pro Pro Ser
  1               5                  10
```

BOVINE ADENOVIRUS EXPRESSION VECTOR SYSTEM

CROSS-REFERENCE TO RELATED APPLICATIONS

This application is a continuation of U.S. patent application Ser. No. 08/164,292, filed Dec. 9, 1993, now U.S. Pat. No. 5,820,868.

TECHNICAL FIELD

The present invention relates novel bovine adenovirus (BAV) expression vector systems in which one or both of the early region 1 (E1) and the early region 3 (E3) gene deletions are replaced by a foreign gene and novel recombinant mammalian cell lines stably transformed with BAV E1 sequences, and therefore, expresses E1 gene products, to allow a bovine adenovirus with an E1 gene deletion replaced by a foreign gene to replicate therein. These materials are used in production of recombinant BAV expressing heterologous (antigenic) polypeptides or fragments for the purpose of live recombinant virus or subunit vaccines or for other therapies.

BACKGROUND OF THE INVENTION

The adenoviruses cause enteric or respiratory infection in humans as well as in domestic and laboratory animals.

The bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4, 5, 6, 7 and 8.

BAV3 was first isolated in 1965 and is the best characterized of the BAV genotypes and contains a genome of approximately 35 kb (Kurokawa et al (1978) *J. Virol.* 28:212–218). The locations of hexon (Hu et al (1984) *J. Viol.* 49:604–608) and proteinase (Cai et al., (1990) *Nuc. Acids Res.*, 18:5568), genes in the BAV3 genome have been identified and sequenced. However, the location and sequences of other genes such as early region 1 (E1) and 3 (E3) in the BAV genome have not been reported.

In the human adenovirus (HAd) genome there are two important regions: E1 and E3 in which foreign genes can be inserted to generate recombinant adenoviruses (Berkner and Sharp (1984) *Nuc. Acid Res.*, 12:1925–1941 and Haj-Ahmad and Graham (1986) *J. Virol.*, 57:267–274). E1 proteins are essential for virus replication in tissue culture, however, conditional-helper adenovirus recombinants containing foreign DNA in the E1 region, can be generated in a cell line which constitutively expresses E1 (Graham et al., (1977) *J. Gen. Virol.*, 36:59–72). In contrast, E3 gene products of HAd 2 and HAd 5 are not required for in vitro or in vivo infectious virion production, but have an important role in host immune responses to virus infection (Andersson et al (1985) *Cell* 43:215–222; Burgert et al (1987) *EMBO J.* 6:2019–2026; Carlin et al (1989) *Cell* 57:135–144; Ginsberg et al (1989) *PNAS, USA* 86:3823–3827; Gooding et al (1988) *Cell* 53:341–346; Tollefson et al (1991) *J. Virol.* 65:3095–3105; Wold and Gooding (1989) *Mol. Biol. Med.* 6:433–452 and Wold and Gooding (1991) *Virology* 184:1–8). The E3-19 kiloDalton (kDa) glycoprotein (gpl9) of human adenovirus type 2 (HAd2) binds to the heavy chain of a number of class 1 major histocompatibility complex (MHC) antigens in the endoplasmic reticulum thus inhibiting their transport to the plasma membrane (Andersson et al. (1985) *Cell* 43:215–222; Burgert and Kvist, (1985) *Cell* 41:987–997; Burgert and Kvist, (1987) *EMBO J.* 6:2019–2026). The E3-14.7 kDa protein of HAd2 or HAd5 prevents lysis of virus-infected mouse cells by tumor necrosis factor (TNF) (Gooding et al. (1988) *Cell* 53:341–346). In addition, the E3-10.4 kDa and E3-14.5 kDa proteins form a complex to induce endosomal-mediated internalization and degradation of the epidermal growth factor receptor (EGF-R) in virus-infected cells (Carlin et al. *Cell* 57:135–144; Tollefson et al. (1991) *J. Virol.* 65:3095–3105). The helper-independent recombinant adenoviruses having foreign genes in the E3 region replicate and express very well in every permissive cell line (Chanda et al (1990) *Virology* 175:535–547; Dewar et al (1989) *J. Virol.* 63:129–136; Johnson et al (1988) *Virology* 164:1–14; Lubeck et al (1989) *PNAS, USA* 86:6763–6767; McDermott et al (1989) *Virology* 169:244–247; Mittal et al (1993) *Virus Res.* 28:67–90; Morin et al (1987) *PNAS, USA* 84:4626–4630; Prevec et al (1990) *J. Inf. Dis.* 161:27–30; Prevec et al (1989) *J. Gen. Virol.* 70:429–434; Schneider et al (1989) *J. Gen. Virol.* 70:417–427 and Yuasa et al (1991) *J. Gen. Virol.* 72:1927–1934). Based on the above studies and the suggestion that adenoviruses can package approximately 105% of the wild-type (wt) adenovirus genome (Bett et al (1993) *J. Virol.* 67:5911–5921 and Ghosh-Choudhury et al (1987) *EMBO. J.* 6:1733–1739), an insertion of up to 1.8 kb foreign DNA can be packaged into adenovirus particles for use as an expression vector for foreign proteins without any compensating deletion.

It is assumed that an indigenous adenovirus vector would be better suited for use as a live recombinant virus vaccine in different animal species compared to an adenovirus of human origin. Non-human adenovirus-based expression vectors have not been reported so far. If like HAds E3, the E3 regions in other adenoviruses are not essential for virus replication in cultured cells, adenovirus recombinants containing foreign gene inserts in the E3 region could be generated.

BAV3 is a common pathogen of cattle usually resulting in subclinical infection though occasionally associated with a more serious respiratory tract infection (Darbyshire et al., 1966 *Res. Vet Sci* 7:81–93; Mattson et al., 1988 *J. Vet Res* 49:67–69). BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418; M. Hitt, personal communication). Cross hybridization was observed between BAV3 and human adenovirus type 2 (HAd2) (Hu et al., 1984 *J. Virol.* 49:604–608) in most regions of the genome including some regions near but not at the left end of the genome.

The E1A gene products of the group C human adenoviruses have been very extensively studied and shown to mediate transactivation of both viral and cellular genes (Berk et al., 1979 *Cell* 17:935–944; Jones and Shenk, 1979 *Cell* 16:683–689; Nevins, 1981 *Cell* 26:213–220; Nevins, 1982 *Cell* 29:913–919; reviewed in Berk, 1986 *Ann. Res. Genet* 20:45–79), to effect transformation of cells in culture (reviewed in Graham, F. L. (1984) "Transformation by and oncogenicity of human adenoviruses. In:The Adenoviruses." H. S. Ginsberg, Editor. Plenum Press, New York; Branton et al., 1985 *Biochim. Biophys. Acta* 780:67–94) and induce cell DNA synthesis and mitosis (Zerler et al., 1987 *Mol. Cell*

*Biol.* 7:821–929; Bellet et al., 1989 *J. Virol.* 63:303–310; Howe et al., 1990 PNAS, USA 87:5883–5887; Howe and Bayley, 1992 *Virology* 186:15–24). The E1A transcription unit comprises two coding sequences separated by an intron region which is deleted from all processed E1A transcripts. In the two largest mRNA species produced from the E1A transcription unit, the first coding regions is further subdivided into exon 1, a sequence found in both the 12s and 13s mRNA species, and the unique region, which is found only in the 13s mRNA species. By comparisons between E1A proteins of human and simian adenoviruses three regions of somewhat conserved protein sequence (CR) have been defined (Kimelman et al., 1985 *J. Virol.* 53:399–409). CR1 and CR2 are encoded in exon 1, while CR3 is encoded in the unique sequence and a small portion of exon 2. Binding sites for a number of cellular proteins including the retinoblastoma protein Rb, cyclin A and an associated protein kinase $p33^{cdk2}$, and other, as yet unassigned, proteins have been defined in exon 1 encoded regions of E1A proteins (Yee and Branton, 1985 *Virology* 147:142–153; Harlow et al., 1986 *Mol. Cell Biol.* 6:1579–1589; Barbeau et al., 1992 *Biochem. Cell Biol.* 70:1123–1134). Interaction of E1A with these cellular proteins has been implicated as the mechanism through which E1A participates in immortalization and oncogenic transformation (Egan et al, 1989 *Oncogene* 4:383–388; Whyte et al., 1988 *Nature* 334:124–129; Whyte et al, 1988 *J. Virol.* 62:257–265). While E1A alone may transform or immortalize cells in culture, the coexpression of both E1A and either the E1B-19 k protein or the E1B-55 k protein separately or together is usually required for high frequency transformation of rodent cells in culture (reviewed in Graham, 1984 supra; Branton et al., 1985 supra; McLorie et al., 1991 *J. Gen Virol.* 72:1467–1471).

Transactivation of other viral early genes in permissive infection of human cells is principally mediated by the amino acid sequence encoded in the CR3 region of E1A (Lillie et al., 1986 *Cell* 46:1043–1051). Conserved cysteine residues in a $CysX_2CysX_{13}CysX_2Cys$ sequence motif (SEQ ID NO:30) in the unique region are associated with metal ion binding activity (Berg, 1986 supra) and are essential for transactivation activity (Jelsma et al., 1988 *Virology* 163:494–502; Culp et al., 1988 *PNAS, USA* 85:6450–6454). As well, the amino acids in CR3 which are immediately amino (N)-terminal to the metal binding domain have been shown to be important in transcription activation, while those immediately carboxy (C)-terminal to the metal binding domain are important in forming associations with the promoter region (Lillie and Green, 1989 *Nature* 338:39–44; see FIG. 3).

The application of genetic engineering has resulted in several attempts to prepare adenovirus expression systems for obtaining vaccines. Examples of such research include the disclosures in U.S. Pat. No. 4,510,245 on an adenovirus major late promoter for expression in a yeast host; U.S. Pat. No. 4,920,209 on a live recombinant adenovirus type 7 with a gene coding for hepatitis-B surface antigen located at a deleted early region 3; European patent 389 286 on a non-defective human adenovirus 5 recombinant expression system in human cells for HCMV major envelope glycoprotein; WO 91/11525 on live non-pathogenic immunogenic viable canine adenovirus in a cell expressing E1a proteins; French patent 2 642 767 on vectors containing a leader and/or promoter from the E3 of adenovirus 2.

The selection of a suitable virus to act as a vector for foreign gene expression, and the identification of a suitable non-essential region as a site for insertion of the gene pose a challenge. In particular, the insertion site must be non-essential for the viable replication of the virus and its effective operation in tissue culture and also in vivo. Moreover, the insertion site must be capable of accepting new genetic material, whilst ensuring that the virus continues to replicate. An essential region of a virus genome can also be utilized for foreign gene insertion if the recombinant virus is grown in a cell line which complements the function of that particular essential region in trans.

The present inventors have now identified suitable regions in the BAV genome and have succeeded in inserting foreign genes to generate BAV recombinants.

DISCLOSURE OF THE INVENTION

The present invention relates to novel bovine adenovirus expression vector systems in which part or all of one or both of the E1 and E3 gene regions are deleted and to recombinant mammalian cell lines of bovine origin transformed with the BAV E1 sequences, and thus, constitutively express the E1 gene products to allow bovine adenovirus, having a deletion of part or all of the E1 gene region replaced by a heterologous nucleotide sequence encoding a foreign gene or fragment thereof, to replicate therein and use of these materials in production of heterologous (antigenic) polypeptides or fragments thereof.

The invention also related to a method of preparing a live recombinant virus or subunit vaccines for producing antibodies or cell mediated immunity to an infectious organism in a mammal, such as bovine, which comprises inserting into the bovine adenovirus genome the gene or fragment coding for the antigen which corresponds to said antibodies or induces said cell mediated immunity, together with or without an effective promoter therefore, to produce BAV recombinants.

Generally, the foreign gene construct is cloned into a nucleotide sequence which represents only a part of the entire viral genome having one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted so that the recombinant vector can express more than one foreign protein. The foreign gene can have additions, deletions or substitutions to enhance expression and/or immunological effects of the expressed protein.

The invention also includes an expression system comprising an bovine adenovirus expression vector wherein heterologous nucleotide sequences with or without any exogenous regulatory elements, replace the E1 gene region and/or part or all of the E3 gene region.

The invention also includes (A) a recombinant vector system comprising the entire BAV DNA and a plasmid or two plasmids capable of generating a recombinant virus by in vivo recombination following cotransfection of a suitable cell line comprising BAV DNA representing the entire wild-type BAV genome and a plasmid comprising a bovine adenovirus left or right end sequences containing the E1 or E3 gene regions, respectively, with a heterologous nucleotide sequence encoding a foreign gene or fragment thereof substituted for part or all of the E1 or E3 gene regions; (B) a live recombinant bovine adenovirus vector (BAV) system selected from the group consisting of: (a) a system wherein part or all of the E1 gene region is replaced by a heterologous nucleotide sequence encoding a foreign gene or fragment thereof; (b) a system wherein a part or all of the E3 gene region is replaced by a heterologous nucleotide sequence encoding a foreign gene or fragment thereof; and (c) a system wherein part or all of the E1 gene region and part or all of the E3 gene region are deleted and a heterologous nucleotide sequence encoding a foreign gene or fragment thereof is inserted into at least one of the deletions; (C) a recombinant bovine adenovirus (BAV) comprising a deletion of part or all of E1 gene region, a deletion of part or all of E3 gene region or deletion of both, and inserted into at least one deletion a heterologous nucleotide sequence coding for an antigenic determinant of a disease causing organism; (D) a recombinant bovine adenovirus expression system comprising a deletion of part or all of E1, a deletion of part or all of E3, or both deletions, and inserted into at least one deletion a heterologous nucleotide sequence coding for a foreign gene or fragment thereof under control of an expression promoter: or (E) a recombinant bovine adenovirus (BAV) for producing an immune response in a mammalian host comprising: (1) BAV recombinant containing a heterologous nucleotide sequence coding for an antigenic determinant needed to obtain the desired immune response in association with or without (2) an effective promoter to provide expression of said antigenic determinant in immunogenic quantities for use as a live recombinant virus or recombinant protein or subunit vaccine; (F) a mutant bovine adenovirus (BAV) comprising a deletion of part or all of E1 and/or a deletion of part or all of E3.

Recombinant mammalian cell lines stably transformed with BAV E1 gene region sequences, said recombinant cell lines thereby capable of allowing replication therein of a bovine adenovirus comprising a deletion of part or all of the E1 or E3 gene regions replaced by a heterologous or homologous nucleotide sequence encoding a foreign gene or fragment thereof. The invention also includes production, isolation and purification of polypeptides or fragments thereof, such as growth factors, receptors and other cellular proteins from recombinant bovine cell lines expressing BAV E1 gene products.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in a target organ or tissue.

Another aspect of the invention provides a virus vaccine composition which comprises the recombinant virus or recombinant protein in association with or without a pharmaceutically acceptable carrier. The recombinant virus vaccine can be formulated for administration by an oral dosage (e.g. as an enteric coated tablet), by injection or otherwise. More specifically, these include a vaccine for protecting a mammalian host against infection comprising a live recombinant adenovirus or recombinant protein produced by the recombinant adenovirus of the invention wherein the foreign gene or fragment encodes an antigen and formulated with or without a pharmaceutically acceptable carrier.

The invention also includes methods of producing antibodies or cell mediated immunity in a mammal including (1) a method for eliciting an immune response in a mammalian host against an infection comprising: administering a vaccine comprising a live BAV recombinant of the invention wherein the foreign gene or fragment encodes an antigen with or without a pharmaceutically acceptable carrier, and (2) a method for eliciting an immune response in a mammalian host against an infection comprising: administering a vaccine comprising a recombinant antigen prepared by culturing a BAV recombinant wherein the foreign gene or fragment encodes the desired antigen with or without a pharmaceutically acceptable carrier.

The following disclosure will render these and other embodiments of the present invention readily apparent to those of skill in the art. While the disclosure often refers to bovine adenovirus type 3 (BAV3), it should be understood that this is for the purpose of illustration and that the same features apply to bovine adenovirus of the other type, 1, 2, 4, 5, 6, 7 8, and 9 and the invention described and claimed herein is intended to cover all of these bovine adenovirus types.

BRIEF DESCRIPTION OF THE DRAWINGS

FIGS. 1A–1L. Sequence and major open reading frames of the left 11% of the BAV3 genome (SEQ ID NO: 1 through SEQ ID NO: 8). The region comprises the E1 and protein IX transcription region. The 195 nucleotide inverted terminal repeat sequence identified by Shinagawa et al., 1987 *Gene* 55:85–93 is shown in italics. The amino acid sequence for the largest E1A protein, two E1B proteins and protein IX are presented. The probable splice donor ([), splice acceptor (]) and intron sequence (underlined italics) within the E1A region are marked. A 35 base pair repeat sequence between E1A and E1B is indicated in bold underline. Possible transcription promoter TATA sequences and possible poly A addition sequences AATAA are also indicated.

FIGS. 2A–2B. Regions of homology in the E1A proteins of BAV3 and human adenovirus type 5 (HAd5). The amino acid residue of each serotype is indicated. A. Conserved region 3 (CR3) of HAd5 (SEQ ID NO:9) subdivided into three functional regions as defined by Lillie et al (1989) *Nature* 338:39–44 and described in the Background of the Invention. The intron sequence of BAV3 E1A occurs within the serine amino acid codon at position 204 (nucleotide positions 1216–1322 of (SEQ ID NO:1). B. A portion of conserved region 2 (CR2) of HAd5 (SEQ ID NO:10), showing the residues thought to be important in the binding of retinoblastoma protein Rb (Dyson et al., 1990 *J. Virol.* 64:1353–1356), and the comparable sequence from BAV3 (SEQ ID NO:34).

FIGS. 3A–3B. Homology regions between the HAd5 and E1B 19k (176R) protein (SEQ ID NO:11 and SEQ ID NO:12) and the corresponding BAV3 (157R) protein (amino acid positions 83–99 and 136–142 of SEQ ID NO:4). The amino acid residue number for each of the viruses is indicated.

FIGS. 4A–4C. The C-terminal 346R of HAd5 E1B 56k (496R) (SEQ ID NO:13) and the corresponding BAV3 protein (420R) (amino acid positions 74–420 of SEQ ID NO:6). The HAd5 protein comparison begins at residue 150 and the BAV3 (in italics) at residue 74. The amino terminal regions of these proteins which are not presented show no significant homology.

FIG. 5. Homology comparison of the amino acid sequence of HAd5 protein IX (SEQ ID NO:14) and the corresponding protein of BAV3 (SEQ ID NO:8) (in italics).

FIGS. 7A–7R. Nucleotide sequence of BAV3 between 77 and 92 m.u. (SEQ ID NO:15 through SEQ ID NO:26) showing ORFs that have the potential to encode polypeptides of at least 50 amino acids after the initiating methionine. The nucleotide sequence was analyzed using the program DISPCOD (PC/GENE). Potential N-glycosylation sites (N-X-T/S) and polyadenylation signals are underlined and the first methionine of each ORF is shown in bold.

FIG. 8(*a*), 8(*b*), 8(*c*)-1, and 8(*c*)-2, and 8(*c*)-3. Comparison between the predicted amino acid sequences for the ORFs of BAV3 and known proteins of HAd2 or -5 using the computer program PALIGN (PC/GENE), with comparison matrix structural-genetic matrix; open gap cost 6; unit gap cost 2. Identical residues are indicated by a colon and similar residues by a dot. (a) Comparison between the predicted amino acid sequence encoded by the 3' end of BAV3 ORF 1 (SEQ ID NO:16) and the HAd2 hexon-associated pVIII precursor (SEQ ID NO:27). (b) Comparison between the ORF 4 (amino acid positions 34–154 of SEQ ID NO:22) and the HAd5 14.7K E3 protein (SEQ ID NO:28). (c) Comparison between the predicted amino acid sequence encoded by BAV3 ORF 6 (amino acid positions 8–983 of SEQ ID NO:26) and the HAd2 fibre protein.

B: BamHI, E: EcoRI, Xb: XbaI, 3.1: BAV3-Luc (3.1), 3.2: BAV3-Luc (3.2) and wt: wild-type BAV3.

Figure 12:
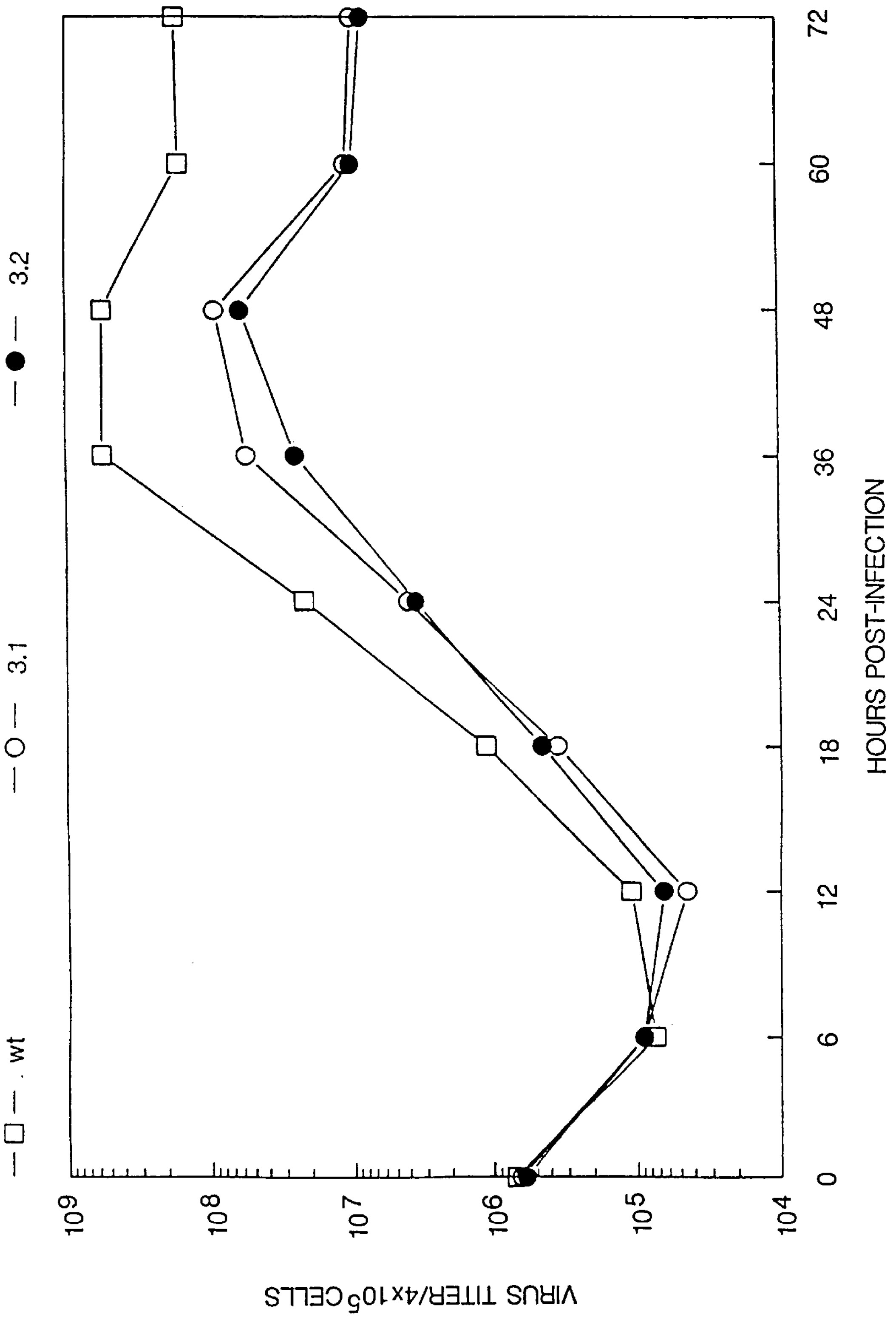

FIG. 12. Single step growth curve for wt BAV3 and BAV3-Luc. Confluent monolayers of MDBK cells in 25 mm multi-well culture plates were inoculated with the wt BAV3, BAV3-Luc (3.1) or BAV3-Luc (3.2) at a m.o.i. of 10 p.f.u. per cell. The virus was allowed to adsorb for 1 h at 37° C., cell monolayers were washed 3 times with $PBS^{++}$ (0.137 M NaCl, 2.7 mM KCl, 8 mM $Na_2HPO_4$, 1.5 mM $KH_2PO4$, containing 0.01% $CaCl_2$. $2H_2O$ & 0.01% $MgCl_2$. $6H_2O$) and incubated at 37° C. in 1 ml maintenance medium containing 2% horse serum. At various times post-infection, cells were harvested along with the supernatant, frozen and thawed three times and titrated on MDBK cells by plaque assay. Results are the means of duplicate samples.

Figure 13:
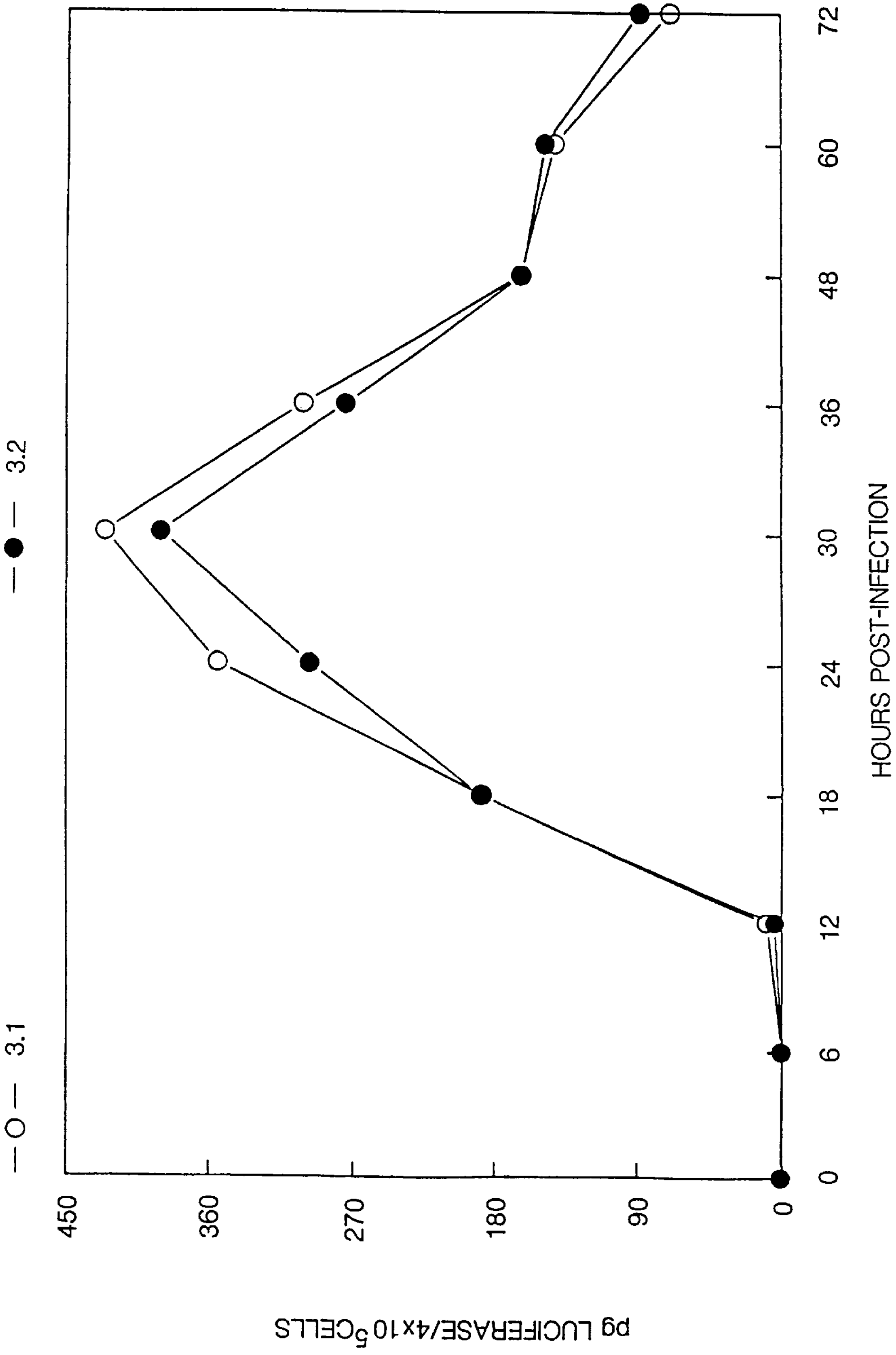

FIG. 13. Kinetics of luciferase expression in MDBK cells-infected with BAV3-Luc. Confluent MDBK cell monolayers in 25 mm multi-well culture plates were infected with BAV3-Luc (3.1) or BAV3-Luc (3.2) at a m.o.i. of 50 p.f.u. per cell. At indicated time points post-infection, virus-infected cells were harvested and assayed in duplicate for luciferase activity.

Figure 14A:
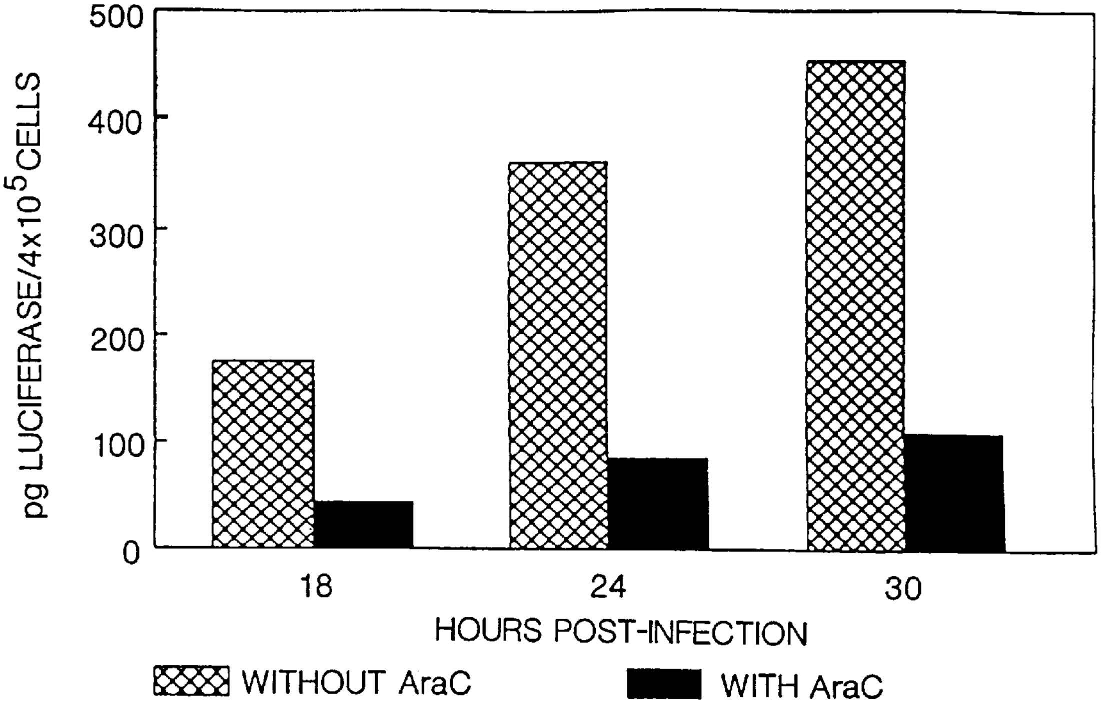
Figure 14B:
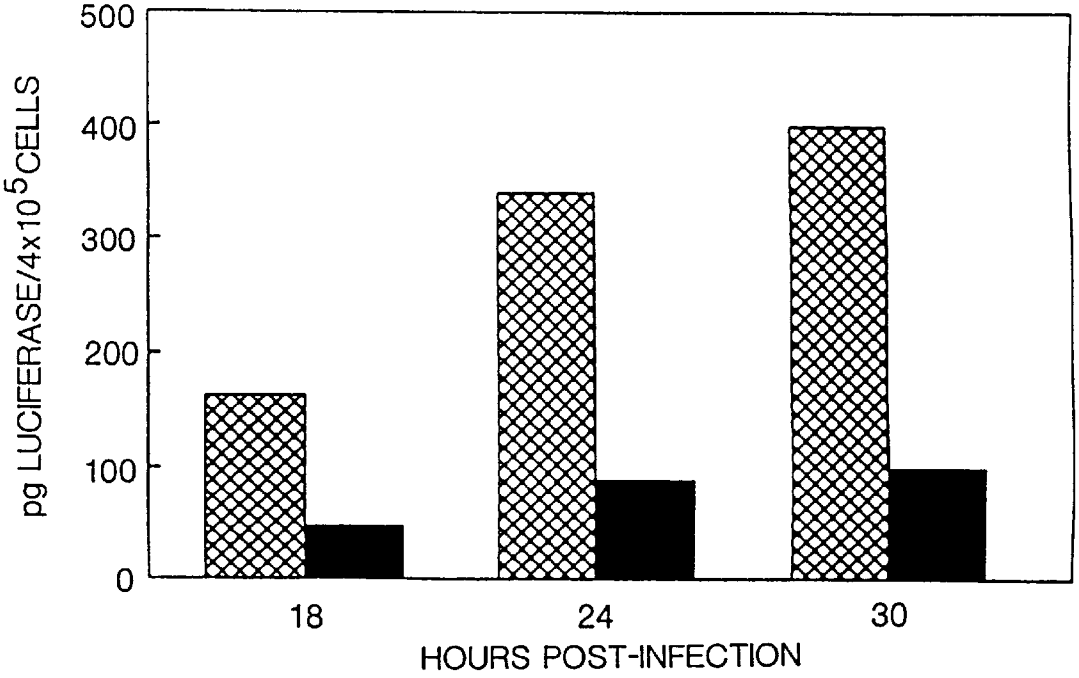

FIG. 14A–14B. Luciferase expression in the presence of 1-β-D-arabinofluranosyl cytosine (AraC) in MDBK cells-infected with BAV3-Luc. Confluent MDBK cell monolayers in 25 mm multi-well culture plates were infected with A)

BAV3-Luc (3.1) or B) BAV3-Luc (3.2) at a m.o.i. of 50 p.f.u. per cell and incubated in the absence or presence of 50 μg AraC per ml of maintenance medium. At indicated time points post-infection, virus-infected cells were harvested and assayed in duplicate for luciferase activity.

Figure 15A:
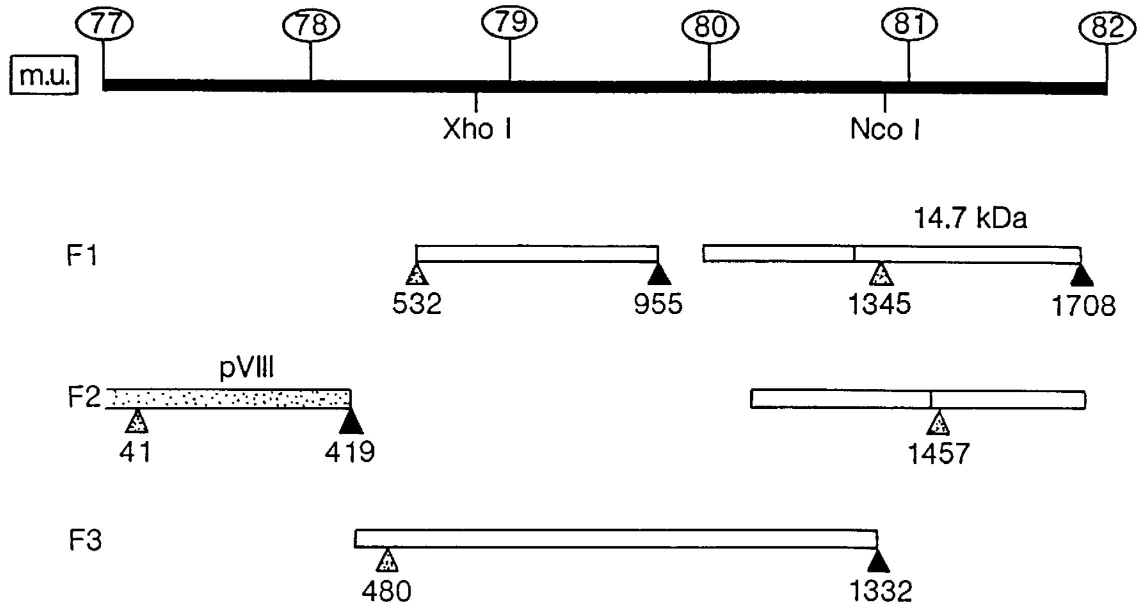
Figure 15B:
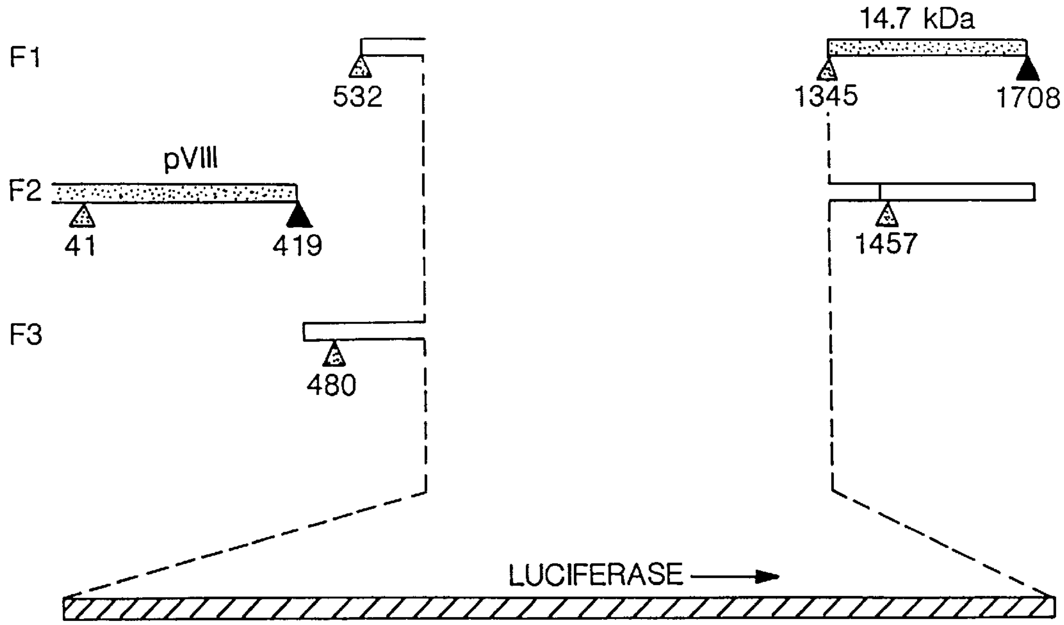

FIGS. 15A–15B. Transcription maps of the wt BAV3 and BAV3-Luc genomes in the E3 region. The genome of wt BAV3 between m.u. 77 and 82 is shown which represents the E3 region. The location of XhoI and NcoI sites which were used to make an E3 deletion are shown. (a) The three frames (F1, F2 and F3) representing the open reading frames (ORFs) in the upper strand of the wt BAV3 genome in the E3 region are represented by bars. The shaded portions indicate regions of similarities to pVIII and E3-14.7 kDa proteins of HAd5. The positions of the initiation and termination codons for ORFs likely to code for viral proteins are shown by open and closed triangles, respectively. (b) The predicted ORFs for the upper strand in E3 of the BAV3-Luc genome are shown after a 696 bp XhoI-NcoI E3 deletion replaced by the luciferase gene. The ORFs for pVIII and E3-14.7 kDa proteins are intact. The transcription map of the wt BAV3 E3 was adapted from the DNA sequence submitted to the GenBank database under accession number D16839.

Figure 16:
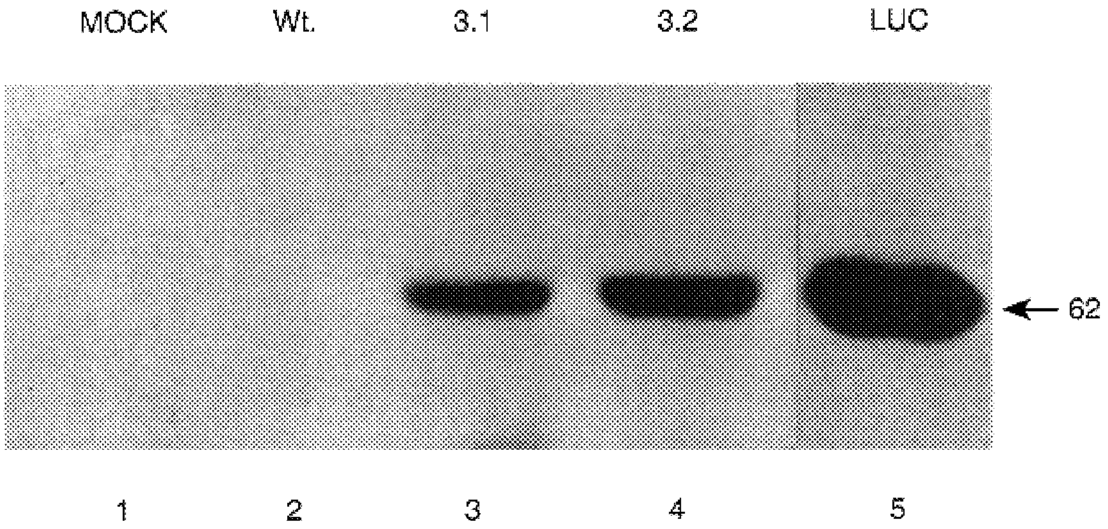

FIG. 16. Western blot analysis of virus-infected MDBK cells using an anti-luciferase antibody. Confluent monolayers of MDBK cells were mock-infected (lane 1) or infected with the wt BAV3 (lane 2), BAV3-Luc (3.1) (lane 3) and BAV3-Luc (3.2) (lane 4) at a m.o.i. of 50 p.f.u. per cell, harvested at 18 h post-infection, cell extracts prepared and analyzed by SDS-PAGE and Western blotting using a rabbit anti-luciferase antibody. Purified firefly luciferase was used as a positive control (lane 5). The lane 5 was excised to obtain a shorter exposure. The protein molecular weight markers in kDa are shown on the left. The arrow indicates the 62 kDa luciferase bands reacted with the anti-luciferase antibody.

wt: wild-type BAV3, 3.1: BAV3-Luc (3.1) and 3.2: BAV3-Luc (3.2).

Figure 17:
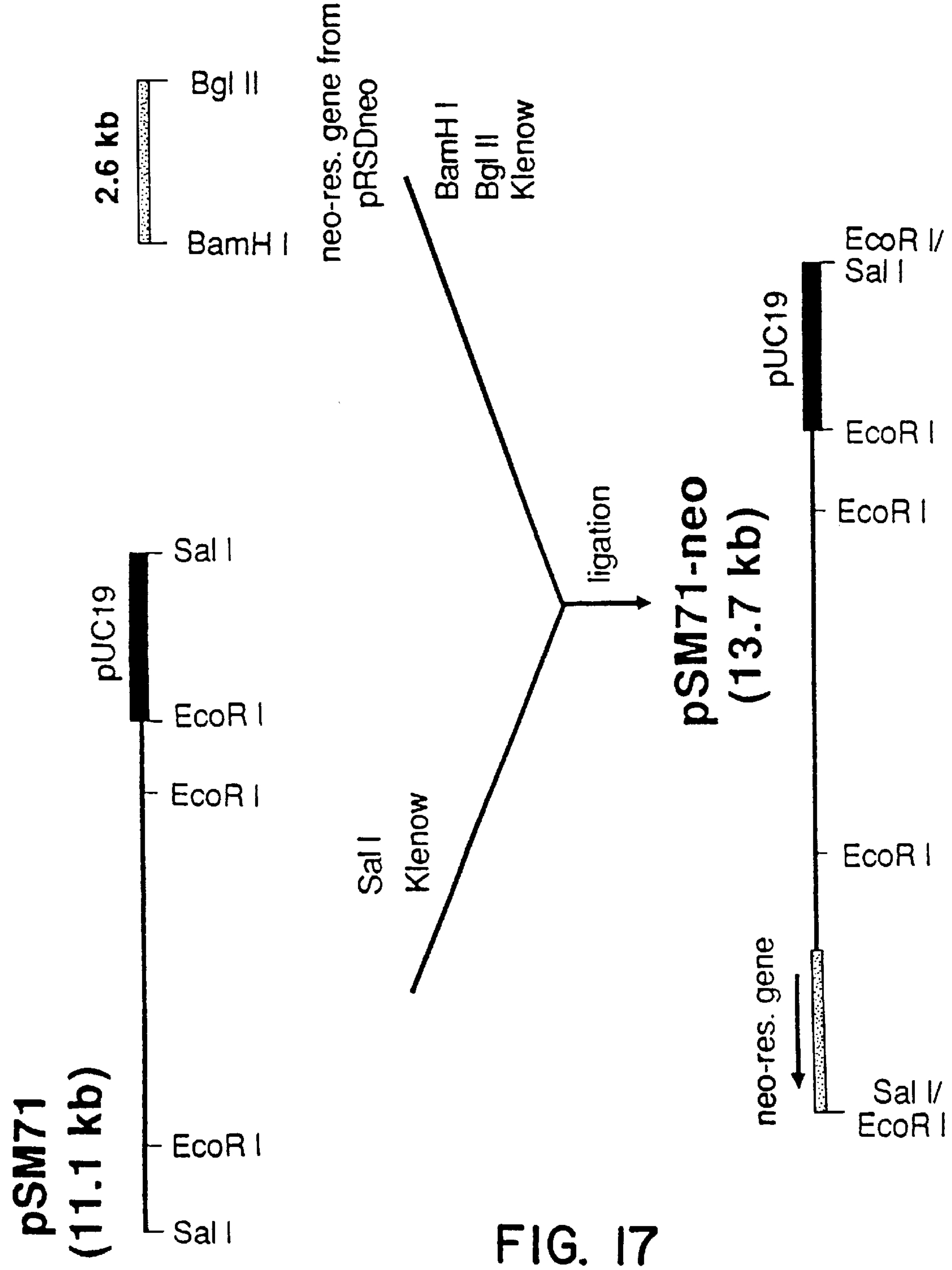

FIG. 17. Construction of pSM71-neo. A 8.4 kb SalI fragment of the BAV3 genome which falls between m.u. 0 and 24 was isolated and inserted into pUC19 at the SalI-SmaI site to generate pSM71. The plasmid, pRSDneo (Fitzpatrick et al (1990) *Virology* 176:145–157) contains the neomycin-resistant (neo$^r$ gene flanked with the simian virus 40 (SV40) regulatory sequences originally from the plasmid, pSV2neo (Southern et al (1982) *J. Mol. Appl. Genet* 1:327–341) after deleting a portion of the SV40 sequences upstream of the neo$^r$ gene to remove several false initiation codons. A 2.6 kb fragment containing the neo$^r$ gene under the control of the SV40 regulatory sequences, was obtained from the plasmid, pRSDneo after digestion with BamHI and BglII, and cloned into pSM71 at the SalI site by blunt end ligation to obtain pSM71-neo containing the neo$^r$ gene in the E1 parallel orientation.

Figure 18:
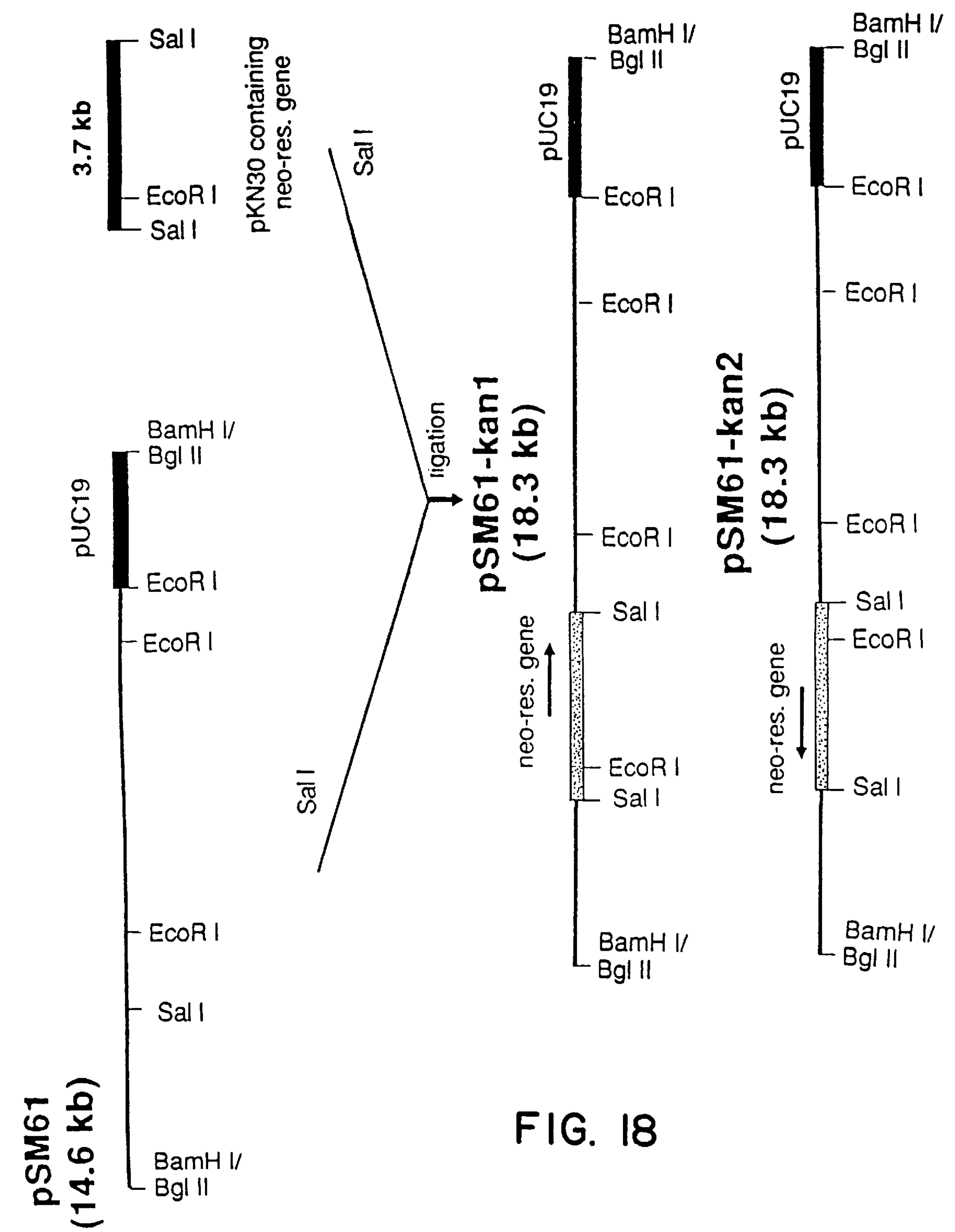

FIG. 18. Construction of pSM61-kan 1 and pSM61-kan2. A 11.9 kb BglII fragment of the BAV3 genome which extends between m.u. 0 and 34 was purified and introduced into pUC19 at the BamHI-HincII site to obtain pSM61. The plasmid, pKN30 contains the neo$^r$ gene along with SV40 promoter and polyadenylation sequences from the plasmid pSV2neo without any modification. The entire pKN30 plasmid was inserted into pSM61 at the SalI site to generate pSM61-kanl having the neo$^r$ gene in the E1 anti-parallel orientation and pSM61-kan2 when the neo$^r$ gene is in the E1 parallel orientation.

Figure 19:
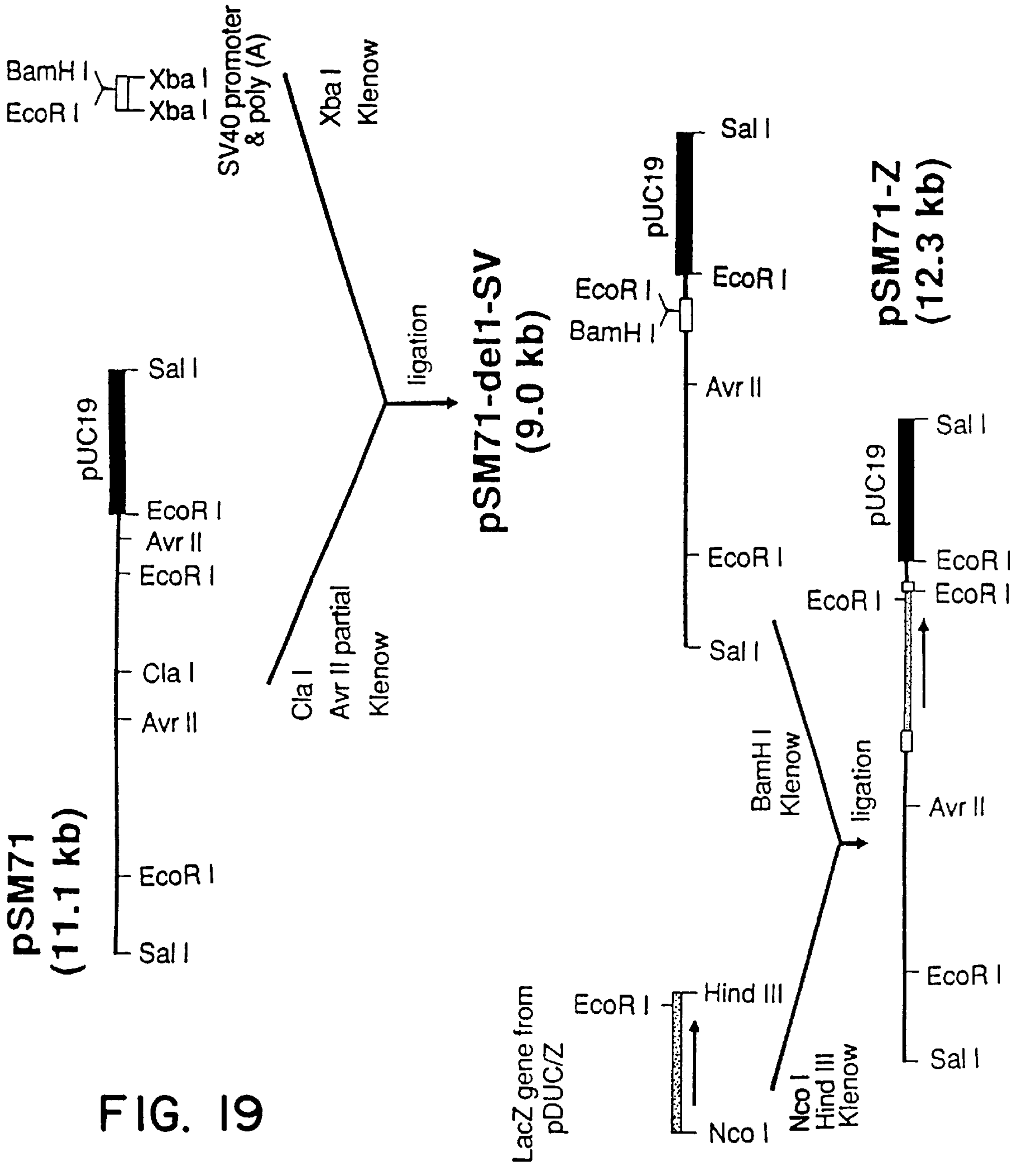

FIG. 19. Construction of an E1 transfer plasmid containing the beta-galactosidase gene.

The plasmid, pSM71 which contains the BAV3 genome between m.u. 0 and 24, was cleaved with ClaI and partially with AvrII to delete a 2.6 kb AvrII-ClaI fragment (between m.u. 1.3 and 8.7) which falls within the E1 region. A 0.5 kb fragment containing the SV40 promoter and polyadenylation sequences was obtained from pFG144K5-SV by digesting with XbaI and inserted into pSM71 to replace the 2.6 kb deletion to generate pSM71-del1-SV. A 3.26 kb fragment containing the bacterial beta-galactosidase gene was isolated from pDUC/Z (Liang et al (1993) *Viroloqy* 195:42–50) after cleavage with NcoI and HindIII and cloned into pSM71-del1-SV at the BamHI site to put the beta-galactosidase gene under the control of the SV40 regulatory sequences to obtain pSM71-Z.

MODES OF CARRYING OUT THE INVENTION

The practice of the present invention will employ, unless otherwise indicated, conventional microbiology, immunology, virology, molecular biology, and recombinant DNA techniques which are within the skill of the art. These techniques are fully explained in the literature. See. e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Sambrook et al., Molecular Cloning: A Laboratory Manual (2nd Edition); vols. I, II & III (1989).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "vector" is a replicon, such as a plasmid, phage, cosmid or virus, to which another DNA segment may be attached so as to bring about the replication of the attached segment.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the -10 and -35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence or sequence encoding is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BAV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BAV or BAV-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or the like, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

B. General Method

The present invention identifies and provides a means of deleting part or all of the nucleotide sequence of bovine adenovirus E1 and/or E3 gene regions to provide sites into which heterologous or homologous nucleotide sequences encoding foreign genes or fragments thereof can be inserted to generate bovine adenovirus recombinants.

By "deleting part of" the nucleotide sequence is meant using conventional genetic engineering techniques for deleting the nucleotide sequence of part of the E1 and/or E3 region.

Various foreign genes or coding sequences (prokaryotic, and eukaryotic) can be inserted in the bovine adenovirus nucleotide sequence, e.g., DNA, in accordance with the present invention, particularly to provide protection against a wide range of diseases and many such genes are already known in the art. The problem heretofore having been to provide a safe, convenient and effective vaccine vector for the genes or coding sequences.

It is also possible that only fragments of nucleotide sequences of genes can be used (where these are sufficient to generate a protective immune response) rather than the complete sequence as found in the wild-type organism. Where available, synthetic genes or fragments thereof can also be used. However, the present invention can be used with a wide variety of genes, fragment and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic. More than one foreign gene can be inserted into the viral genome to obtain successful production of more than one effective protein.

Thus with the recombinant virus of the present invention, it is possible to provide protection against a wide variety of diseases affecting cattle. Any of the recombinant antigenic determinant or recombinant live virus of the invention can be formulated and used in substantially the same manner as described for the antigenic determinant vaccines or an live vaccine vectors.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host an "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine parainfluenza virus type 3 (BPI-3), bovine diarrhea virus, *Pasteurella haemolytica, Haemophilus somnus* and the like. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^8$ pfu and the like can be used. As with in vitro subunit vaccines, additional dosages can be given as determined by the clinical factors involved.

In one embodiment of the invention, a number of recombinant cell lines are produced according to the present invention by constructing an expression cassette comprising the BAV E1 region and transforming host cells therewith to provide cell lines or cultures expressing the E1 proteins. These recombinant cell lines are capable of allowing a recombinant BAV, having an E1 gene region deletion replaced by heterologous nucleotide sequence encoding for a foreign gene or fragment, to replicate and express the desired foreign gene or fragment thereof which is encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection.

In one embodiment of the invention, the recombinant expression cassette can be obtained by cleaving the wild-type BAV genome with an appropriate restriction enzyme to produce a DNA fragment representing the left end or the right end of the genome comprising E1 or E3 gene region sequences, respectively and inserting the left or right end fragment into a cloning vehicle, such as plasmid and thereafter inserting at least one DNA sequence encoding a foreign protein, into E1 or E3 deletion with or without the control of an exogenous promoter. The recombinant expression cassette is contacted with the wild-type BAV DNA through homologous recombination or other conventional genetic engineering method within an E1 transformed cell line to obtain the desired recombinant.

The invention also includes an expression system comprising an bovine adenovirus expression vector wherein a heterologous nucleotide, e.g. DNA, replaces part or all of the E3 region and/or part or all of the E1 region. The expression system can be used wherein the foreign nucleotide sequences, e.g. DNA, is with or without the control of any other heterologous promoter.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides,, including those such as (a) proteins associated with adenovirus E1A proteins: e.g. p300, retinoblastoma(Rb) protein, cyclins, kinases and the like.; (b) proteins associated with adenovirus E1B protein: e.g. p53 and the like.; (c) growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IFG-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity and the like; (f) other cellular proteins such as actins, collagens, fibronectins, integrins, phospholipids, proteoglycans, histones and the like, and (g) proteins involved in regulation of transcription such as TATA-box-binding protein (TBP), TBP-associated factors (TAFs). SP1 binding protein and the like.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are recently being used by those of skill in the art to replace a defective gene or portion thereof. Examples of foreign genes nucleotide sequences or portions thereof that can be incorporated for use in a conventional gene therapy include, cystic fibrosis transmembrane conductance regulator gene, human minidystrophin gene, alphal-antitrypsin gene and the like.

EXAMPLES

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Cells and Viruses

Cell culture media and reagents were obtained from GIBCO/BRL Canada (Burlington, Ontario, Canada). Media were supplemented with 25 mM Hepes and 50 μg/ml gentamicin. MDBK cells or MDBK cells transformed with a plasmid containing BAV3 E1 sequences were grown in MEM supplemented with 10% Fetal bovine serum. The wild-type BAV3 ((strain WBR-1) (Darbyshire et al, 1965 *J.*

*Comparative Pathology* 75:327) was kindly provided by Dr. B. Darbyshire, University of Guelph, Guelph, Canada) and BAV3-luciferase recombinants working stocks and virus titrations were done in MDBK cells.

Enzymes, Bacteria and Plasmids

Restriction endonucleases, polymerase chain reaction (PCR) and other enzymes required for DNA manipulations were purchased from Pharmacia LKB Biotechnology (Canada) Ltd. (Dorval, Quebec, Canada), Boehringer-Mannheim, Inc. (Laval or Montreal, Quebec, Canada), New England BioLabs (Beverly, Mass.), or GIBCO/BRL Canada (Burlington, Ontario, Canada) and used as per manufacturer's instructions. Restriction enzyme fragments of BAV3 DNA were inserted into pUC18 or pUC19 (Yanich-Penon et al (1985) *Gene* 33:103–109) following standard procedures (Sambrook et al (1989) Molecular Cloning: A Laboratory Manual, 2nd ed. Cold Spring Harbour Laboratory, New York). *E. coli* strain DH5 (supE44 hsdR17 recA1 endA1 gyrA96 thi-1 relA1) was transformed with recombinant plasmids by electroporation (Dower et al. (1988) *Nuc. Acids Res.*, 16:6127–6145). Plasmid DNA was prepared using the alkaline lysis procedure (Bernboim and Doly (1978) *Nuc. Acids Res.*, 7:1513–1523). The plasmid, pSVOA/L containing the entire cDNA encoding firefly luciferase (de Wet et al (1987) *Mol. Cell. Biol.* 7:725–737), was a gift from D.R. Helinski, University of California, San Diego, La Jolla, Calif.

Construction of Recombinant BAV3

MDBK cells transformed with a plasmid containing BAV3 E1 sequences were cotransfected with the wt BAV3 DNA digested with PvuI and the plasmid, pSM51-Luc (FIGS. 9 and 10) using the lipofection-mediated cotransfection protocol (GIBCO/BRL, Life Technologies, Inc., Grand Island, N.Y.). The virus plaques produced following cotransfection were isolated, plaque purified and the presence of the luciferase gene in the BAV3 genome was detected by agarose gel electrophoresis of recombinant virus DNA digested with appropriate restriction enzymes.

Southern Blot and Hybridization

Mock or virus-infected MDBK cells were harvested in lysis buffer (500 $\mu$g/ml pronase in 0.01 M Tris, pH 7.4, 0.01 M EDTA, 0.5% SDS) and DNA was extracted (Graham et al (1991) Manipulation of adenovirus vectors In: Methods and Molecular Biology, 7: Gene Transfer and Expression Techniques (Eds. Murray and Walker) Humana Press, Clifton, N. J. pp. 109–128). 100 ng DNA was digested either with BamHI, EcoRI or XbaI and resolved on a 1% agarose gel by electrophoresis. DNA bands from the agarose gel were transferred to a GeneScreenPlus™ membrane (Du Pont Canada Inc. (NEN Products), Lachine, Quebec, Canada) by the capillary blot procedure (Southern, E. M. (1975) *J. Mol. Biol.* 98:503–517). Probes were labeled with $^{32}P$ using an Oligolabeling Kit (Pharmacia LKB Biotechnology (Canada) Ltd., Dorval, Quebec, Canada) and the unincorporated label was removed by passing the labeled probe through a sephadex G-50 column (Sambrook et al (1989) supra). Probes were kept in a boiling water bath for 2 min and used in hybridization experiments following GeneScreenPlus™ hybridization protocol. The DNA bands which hybridized with the probe were visualized by autoradiography.

Luciferase Assays

The protocol was essentially the same as described (Mittal et al (1993) *Virus Res.* 28:67–90). Briefly, MDBK cell monolayers in 25 mm multi-well dishes (Corning Glass Works, Corning, N.Y.) were infected in duplicate either with BAV3-Luc (3.1) or BAV3-Luc (3.2) at a m.o.i. of 50 p.f.u. per cell. At indicated time points post-infection, recombinant virus-infected cell monolayers were washed once with PBS (0.137 M NaCl, 2.7 mM KCl, 8 mM $Na_2HPO_4$, 1.5 mM $KH_2PO_4$) and harvested in 1 ml luciferase extraction buffer (100 mM potassium phosphate, pH 7.8, 1 mM dithiothreitol). The cell pellets were resuspended in 200 $\mu$l of luciferase extraction buffer and lysed by three cycles of freezing and thawing. The supernatants were assayed for luciferase activity. For the luciferase assay, 20 $\mu$l of undiluted or serially diluted cell extract was mixed with 350 $\mu$l of luciferase assay buffer (25 mM glycylglycine, pH 7.8, 15 mM $MgCl_2$, 5 mM ATP) in a 3.5 ml tube (Sarstedt Inc., St-Laurent, Quebec, Canada). Up to 48 tubes can be kept in the luminometer rack and the equipment was programed to inject 100 $\mu$l of luciferin solution (1 mM luciferin in 100 mM potassium phosphate buffer, pH 7.8) in the tube present in the luminometer chamber to start the enzyme reaction. The Luminometer (Packard Picolite Luminometer, Packard Instrument Canada, Ltd., Mississauga, Ontario, Canada) used in the present study produced 300 to 450 light units of background count in a 10 sec reaction time. Known amounts of the purified firefly luciferase were used in luciferase assays to calculate the amount of active luciferase present in each sample.

Western Blotting

Mock or virus-infected MDBK cells were lysed in 1:2 diluted 2X loading buffer (80 mM Tris-HCl, pH 6.8, 0.67 M urea, 25% glycerol, 2.5% SDS, 1 M mercaptoethanol, 0.001% bromophenol blue), boiled for 3 min and then centrifuged to pellet cell debris. Proteins were separated by SDS-polyacrylamide gel electrophoresis (SDS-PAGE) on 0.1% SDS-10% polyacrylamide gels (Laemmli, et al (1970) *Nature* 227:680–685). After the end of the run, polypeptide bands in the gel were electrophoretically transferred to a nitrocellulose membrane (Bio-Rad Laboratories, Richmond, Calif.). The membrane was incubated at room temperature for 2 h with 1:4000 diluted rabbit anti-luciferase antibody (Mittal et al (1993) supra). The binding of anti-luciferase antibody to the specific protein band/s on the membrane was detected with 1:5000 diluted horseradish peroxidase conjugated-goat anti-rabbit IgG (Bio-Rad Laboratories, Richmond, Calif.) and with an ECL Western blotting detection system (Amersham Canada Ltd., Oakville, Ontario).

Example 1

Cloning of BAV3 E1 Region DNA for Sequencing

To complement the restriction site (Kurokawa et al, 1978 *J. Virol.*, 28:212–218; Hu et al, 1984 *J. Virol.* 49:604–608) other restriction enzyme sites in the BAV3 genome were defined. The 8.4 kilobase pair (kb) SalI B fragment which extends from the left end of the genome to approximately 24% was cloned into the SmaI-SalI sites of pUC18 essentially as described previously (Graham et al, 1989 *EMBO Journal* 8:2077–2085). Beginning at the left end of the BAV3 genome, the relevant restriction sites used for subsequent subcloning and their approximate positions are: SacI (2%), EcoRI (3.5%), HindIII (5%), SacI (5.5%), SmaI (5.6%) and HindIII (11%). Through the use of appropriate restriction enzymes, the original plasmid was collapsed to contain smaller inserts which could be sequenced using the pUC universal primers. Some fragments were also subcloned in both pUC18 and pUC19 to allow confirmational sequencing in both directions. These procedures, together with the use of twelve different oligonucleotide primers hybridizing with BAV3 sequences, allowed to sequence the BAV3 genome from its left end to the HindIII site at 11%.

To ensure that some features of the sequence obtained were not unique to the initial clone selected for sequencing, two more pUC19 clones were prepared containing the SalI fragment from a completely independent DNA preparation. These clones were used to confirm the original sequence for the region from approximately 3% to 5.5% of the BAV3 genome.

DNA sequencing reactions were based on the chain-termination method (Sanger et al. 1977 *PNAS, USA* 74:5463–5467) and manual sequencing followed the DNA sequencing protocol described in the Sequenase kit produced by US Biochemical. [$\alpha$-$^{35}$S]dATPs was obtained from Amersham Canada Ltd. All oligonucleotides used as primers were synthesized by the Central Facility of the Molecular Biology and Biotechnology Institute (MOBIX) at McMaster University, Hamilton, Ontario. The entire region (0 to 11%) of the BAV3 genome was sequenced by at least two independent determinations for each position by automated sequencing on a 373A DNA Sequencer (Applied Biosystems) using Taq-Dye terminators. Over half of the region was further sequenced by manual procedures to confirm overlaps and other regions of interest.

DNA sequence analysis and protein comparisons were carried out on a MICROGENIE program.

Example 2

Coding Sequences of the BAV3 E1 Region

BAV3 genomic DNA, from the left end of the genome to the HindIII site at approximately 11%, was cloned into plasmids and sequenced by a combination of manual and automated sequencing. An examination of the resultant BAV3 E1 genomic sequence (FIG. 1) revealed a number of interesting features relevant both to transactivation and to other functions associated with adenovirus E1 proteins. On the basis of open reading frames (ORFS) it was possible to assign potential coding regions analogous to those defined in human Ad5 (HAdS). As shown in FIG. 1, ORFs corresponding roughly to the first exon and unique region of HAd5 E1A as well are ORFs corresponding to the 19k and 58k proteins of E1B and the ORF corresponding to protein IX were all defined in this sequence. The open reading frame defining the probable E1A coding region begins at the ATG at nt 606 and continues to a probable splice donor site, at position 1215. The first consensus splice acceptor site after this is located after nt 1322 and defines an intron of 107 base pairs with an internal consensus splice branching site at position 1292. The putative BAV3 E1A polypeptide encoded by a message corresponding to these splice sites would have 211 amino acids and a unmodified molecular weight of 23,323. The major homology of the protein encoded by this ORF and HAd5 E1A is in the residues corresponding to CR3 (shown in FIG. 2). The homology of amino acid sequences on both sides of the putative intron strengthens the assignment of probable splice donor and acceptor sites. The CR3 has been shown to be of prime importance in the transactivation activity of HAd5 E1A gene products. As seen in FIG. 2A the homology of this sequence in the BAV3 protein to the corresponding region of the 289R E1A protein of HAd5 includes complete conservation of the $CysX_2CysX_{13}CysX_2Cys$ sequence motif (SEQ ID NO:30) which defines the metal binding site of this protein (Berg, 1986 *Science* 232:485–487) as well as conservation of a number of amino acids within this region and within the promoter binding region as defined by Lillie and Green 1989 *Nature* 338:39–44).

The only other region of significant homology between the BAV3 E1A protein and that of HAd5 was a stretch of amino acids known to be important in binding of the cellular Rb protein to the HAd5 E1A protein (Dyson et al, 1990 *J. Virol.* 64:1353–1356). As shown in FIG. 2B, this sequence, which is located between amino acids 120 and 132 in the CR2 region of HAd5 E1A, is found near the amino (N–) terminus of the BAV3 protein between amino acids 26 and 37.

An open reading frame from the ATG at nt 1476 to the termination signal at 1947 defines a protein of 157 amino acids with two regions of major homology to the HAdS E1B 19k protein. As shown in FIG. 3 both the BAV3 and the HAd5 proteins have a centrally located hydrophobic amino acid sequence. The sequence in BAV3, with substitutions of valine for alanine and leucine for valine, should result in a somewhat more hydrophobic pocket than the corresponding HAd5 region. The other portion of HAd5 19k that may be conserved in the BAV3 protein is the serine rich sequence found near the N-terminus (residues 20 to 26) in HAd5 19k and near the C-terminus (residues 136 to 142) in the BAV3 protein (also shown in FIG. 3).

On ORF beginning at the ATG at nt 1850 and terminating at nt 3110 overlaps the preceding BAV3 protein reading frame and thus has the same relationship to it as does the HAd5 E1B 56k protein to E1B 19k protein. As shown in FIG. 4 this BAV3 protein of 420R and the corresponding HAd5 E1B 56k protein of 496R show considerable sequence homology over their C-terminal 346 residues. The N-terminal regions of these proteins (not depicted in the figure) show no significant homology and differ in overall length.

Following the E1B ORFS, the open reading frame beginning at nt 3200 and ending at the translation terminator TAA at nt 3575 defines a protein of 125R with an unmodified molecular weight of 13,706. As seen in FIG. 5 this protein shares some homology with the structural protein IX of HAdS particularly in N-terminal sequences.

Possible Transcription Control Regions in BAV3 E1

The inverted terminal repeats (ITR) at the ends of the BAV3 genome have been shown to extend to 195 nt (Shinagawa et al, 1987 *Gene* 55:85–93). The GC-rich 3' portion of the ITR contains a number of consensus binding sites for the transcription stimulating protein SP1 (Dynan and Tijan (1983) *Cell* 35:79–87) and possible consensus sites for the adenovirus transcription factor (ATF) (Lee et al. (1987) *Nature* 325:368–372) occur at nts 60 and 220. While there are no exact consensus sites for the factors EF-1A (Bruder and Healing (1989) *Mol. Cell Biol.* 9:5143–5153) or E2F (Kovesdi et al, 1987 *PNAS. USA* 84:2180–2184) upstream of the ATG at nt 606, there are numerous degenerate sequences which may define the enhancer region comparable to that seen in HAd5 (Hearing and Shenk, 1986 *Cell* 45:229–236).

The proposed BAV3 E1A coding sequence terminates at a TGA residue at nt 1346 which is located within a 35 base pair sequence which is immediately directly repeated (see FIG. 1). Two repeats of this sequence were detected in three independently derived clones for a plaque purified stock of BAV3. The number of direct repeats can vary in any BAV3 population though plaque purification allows for isolation of a relatively homogeneous population of viruses. That direct repeats in the sequences can function as promoter or enhancer elements for E1B transcription is being tested. There are no strong polyA addition consensus sites between the E1A and the E1B coding sequences and in fact no AATAA sequence is found until after the protein IX coding sequences following E1B. The TATAAA sequence beginning at nt 1453 could function as the proximal promoter for E1B but it is located closer to the ATG at 1476 than is considered usual (McKnight et al, 1982 *Science* 217:316–322). The TATA sequence located further upstream immediately before the proposed E1A intron sequence also seems inappropriately positioned to serve as a transcription box for the E1B proteins. There are clearly some unique features in this region of the BAV3 genome.

The transcriptional control elements for the protein IX transcription unit are conventional and well defined. Almost immediately following the open reading frame for the larger E1B protein there is, at nt 3117, a SP1 binding sequence. This is followed at 3135 by a TATAAAT sequence which could promote a transcript for the protein IX open reading frame beginning at the ATG at 3200 and ending with the TAA at 3575. One polyA addition sequence begins within the translation termination codon and four other AATAA sequences are located at nts 3612, 3664, 3796 and 3932.

In keeping with the general organization of the E1A region of other adenoviruses, the BAV3 E1A region contains an intron sequence with translation termination codons in all three reading frames and which is therefore probably deleted by splicing from all E1A mRNA transcripts. The largest possible protein produced from the BAV3 E1A region will have 211 amino acid residues and is the equivalent of the 289 amino acid protein translated from the 13s mRNA of HAd5. Two striking features in a comparison of these proteins are the high degree of homology in a region corresponding to CR3 and the absence in BAV3 of most of amino acids corresponding to the second exon of HAd5. In fact the only amino acids encoded in the second exon of BAV3 are, those which are considered to constitute part of CR3. A great deal of work carried out with HAd5 has identified the importance of the CR3 sequences in transactivation of other HAd5 genes. While a detailed analysis of the corresponding BAV3 region and its possible role in transactivation of BAV3 genes needs to be carried out, it is none-the-less interesting to note a couple of possibly pertinent features. The HAd5 CR3 region has been operationally subdivided into three regions (Lillie et al, 1989 *Nature* 338:39–44; see FIG. 8); an N-terminal region from 139 to 153 which has four acidic residues and is thought to be important in transcription activation, a central, metal-binding, region defined by the Cys-$X_2$-Cys-$X_{13}$-Cys$X_2$-Cys sequence (SEQ ID NO:30) which is essential for both promoter binding and activation, and a C-terminal region (residues 175–189) which is essential for promoter binding. Since, in most instances, E1A protein is thought not to interact directly with DNA (Ferguson et al 1985), the promoter binding regions may be involved in forming associations with proteins which then allow association with DNA. In FIG. 2*a* the BAV3 E1A protein contains the central, metal binding domain and has considerable homology in the carboxy portion of this region. The BAV3 E1A protein also shows identity of sequence with HAd5 in the carboxy 6 amino acids of the promoter binding domain. These features may allow the BAV3 E1A protein to interact with the same transcription activating factors required for HAd5 E1A function. In contrast, except for a Glu-Glu pair there is little homology between the bovine and human viruses in the activation domain. The fact that this domain can be functionally substituted by a heterologous acidic activation sequence (Lillie et al, 1989 supra) suggests that protein specificity is not required in this region and this may allow the BAV3 E1A protein to function in the activation of BAV3 genes. The BAV3 E1A activation region contains six acidic residues in the 18 residues amino to the metal binding domain.

The other interesting feature of BAV3 E1A, which is undoubtedly relevant to the oncogenic potential of this virus, is the presence of the sequence Asp27-Leu-Glu-Cys-His-Glu which conforms to, a core sequence known to be important in the binding of cellular Rb and related proteins by the transforming proteins of a number of DNA tumour viruses (Dyson et al, 1990 supra). From deletion mutant analysis there is a clear association between the potential of HAd5 E1A proteins to bind Rb and the ability of the protein to induce morphological transformation in appropriate cells (see references in Dyson et al, 1990 supra). The BAV3 E1A protein is distinct from its HAd5 counterpart in the relative position of this Rb binding sequence which is in the CR2 of HAd5 E1A and near the N-terminus of the BAV3 E1A protein.

Through the use of alternative splice sites HAd5 E1A transcripts can give rise to at least 5 distinct mRNA species (Berk et al, 1978 *Cell* 14:695–711; Stephens et al, 1987 *EMBO Journal* 6:2027–2035). Whether BAV3, like HAd5, can generate a number of different mRNA species through the use of alternative splice sites in the E1A transcripts remains to be determined. For example a potential splice donor site which could delete the sequence equivalent to the unique sequence of HAd5 is present immediately after nt 1080 but it is not known if this site is actually used.

HAd5 E1B encodes two proteins (19k and 56k) either of which can cooperate with E1A, by pathways which are additive and therefore presumably independent (McLorie et al, 1991 *J. Gen. Virol.* 72:1467–1471), to produce morphological transformation of cells in culture (see for example: Branton et al, 1985 supra; Graham, 1984 supra). The significance of the conservation of the hydrophobic stretch of amino acids in the central portion of the shorter E1B proteins of HAd5 and BAV3 is not clear as yet. A second short region of homology Gln-Ser-Ser-X-Ser-Thr-Ser (SEQ ID NO:31) at residue 136 near the C-terminus of the BAV3 protein is located near the N-terminus at residue 20 in the HAdS 19k protein. The major difference in both length and sequence of the larger (420R) E1B protein of BAV3 from the corresponding HAd5 protein (496R) is confined to the N-terminus of these proteins. The two proteins show considerable evolutionary homology in the 345 amino acids that extend to their C-termini. A similar degree of homology extends into the N-terminal halves of protein IX of BAV3 and HAd5. Taken together these analyses suggest that while BAV3 and the human adenoviruses have diverged by simple point mutational events in some regions, more dramatic genetic events such as deletion and recombination may have been operating in other regions particularly those defining the junction between E1A and E1B.

Example 3

Cloning and Sequencing of the BAV3 E3 and Fibre Genes

Figure 6:
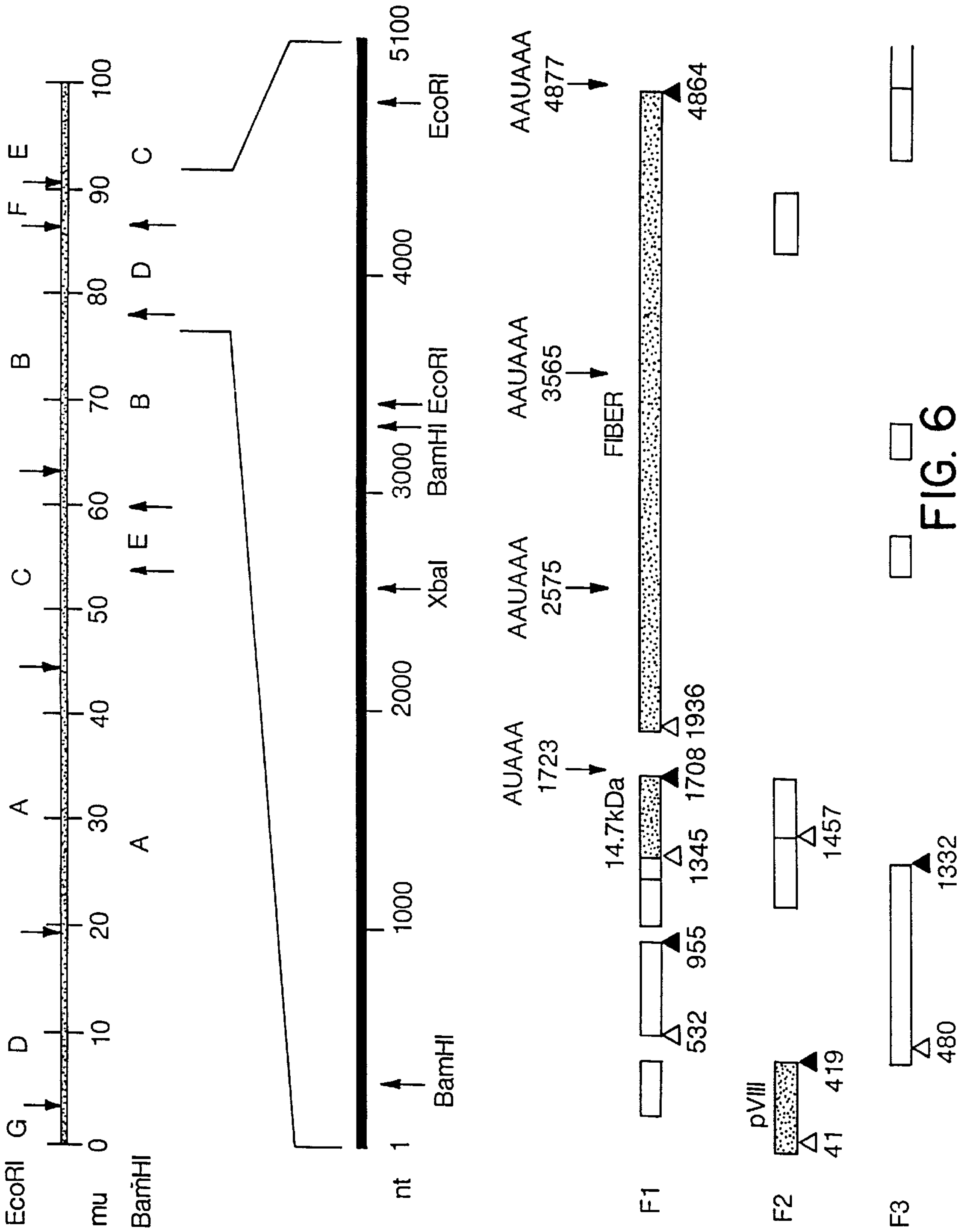
FIG. 6. The genome of BAV3 showing the location of EcoRI, XbaI and BAMHI sites and the structure of the 5100 bp segment from 77 to 92 m.u. ORFs for the upper strand which can encode 60 amino acids or more are represented by bars. Shaded portions indicate regions of similarity to pVIII, 14.7K E3 and fibre proteins of HAd2 or -5. The first methionine followed by a stretch of amino acids of at least 50 is shown by an open triangle. Termination codons for ORFs likely to code for viral proteins are shown by closed triangles.

The general organization of adenovirus genomes seems to be relatively well conserved so it was possible to predict, from the locations of a number of HAd E3 regions, that BAV E3 should lie between map units (m.u.) 77 to 86. To prepare DNA for cloning and sequencing, BAV3 (strain WBR-1) was grown in Madin-Darby bovine kidney (MDBK) cells, virions were purified and DNA was extracted (Graham, F. L. & Prevec, L. (1991) Methods in Molecular Biology, vol. 7, Gene Transfer and Expression Protocols, pp. 109–146. Edited by E. J. Murray, Clifton, New Jersey; Humana Press.). Previously published restriction maps for EcoRI and BamHI (Kurokawa et al., 1978) were confirmed (FIG. 6). The BamHI D and EcoRI F fragments of BAV3 DNA were isolated and inserted into pUC18 and pUC19 vectors, and nested sets of deletions were made using exonuclease III and S1 nuclease (Henikoff, S. (1984) *Gene*, 28:351–359). The resulting clones were sequenced by the dideoxynucleotide chain termination technique (Sanger, F., Nicklen, S. &

Coulson, A. R. (1977) *Proceedings of the National Academy of Sciences, U.S.A.*, 74:5463–5467). The nucleotide sequence from positions 1 to 287 was obtained from the right end of the BamHI B fragment (FIG. 6). The sequence of the regions spanning (i) the BamHI site at nucleotide 3306 and the EcoRI site at nucleotide 3406, and (ii) the EcoRI site at nucleotide 4801 and the nucleotide 5100 was obtained from a plasmid containing the XbaI C fragment (m.u. 83 to 100; not shown) using primers hybriding to BAV3 sequences. Analysis of the sequence was performed with the aid of the PC/GENE sequence analysis package developed by Amos Bairoch, Department of Medical Biochemistry, University of Geneva, Switzerland.

The 5100 nucleotide sequence which extends between 77 and 92 m.u. of the BAV3 genome is shown in FIG. 7. The upper strand contains 14 open reading frames (ORFs) which could encode polypeptides of 60 amino acid residues or more (FIG. 6 and 7). The lower strand contains no ORF encoding a protein of longer than 50 amino acids after an initiation codon. The predicted amino acid sequence for each ORF on the upper strand was analyzed for homology with predicted amino acid sequences from several sequenced Ads: HAd2 (Hérissé, J., Courtois, G. & Galibert, F. (1980) *Nucleic Acids Research*, 8:2173–2192; Hérissé, J., Courtois, G. & Galibert, F. (1981) *Nucleic Acids Research*, 9:1229–1249), -3(Signas, C., Akusjarvi, G. & Pettersson, U. (1985) *Journal of Virology*, 53:672–678.), -5(Cladaras, C. & Wold, W. S. M. (1985) *Virology*, 140:28–43), -7 (Hong, J. S., Mullis, K. G. & Engler, J. A. (1988) *Virology*, 167:545–553) and -35(Flomenberg, P. R., Chen, M. & Horwitz, M. S. (1988) *Journal of Virology*, 62:4431–4437), and murine Ad1 (MAd1) (Raviprakash, K. S., Grunhaus, A., El Kholy, M. A. & Horwitz, M. S. (1989) *Journal of Virology*, 63:5455–5458) and canine Ad1 (CAd1) (Dragulev, B. P., Sira, S., Abouhaidar, M. G. & Campbell, J. B. (1991) *Virology*, 183:298–305). Three of the BAV3 ORFs exhibited homology with characterized HAd proteins pVIII, fibre and the 14.7K E3 protein. The amino acid sequence predicted from BAV3 ORF 1 shows overall identity of approximately 55% when compared to the C-terminal 75% of HAd2 pVIII (Cladaras & Wold, 1985, supra) (FIG. 8*a*), indicating that ORF 1 encodes the right end of BAd3 pVIII. Near the C-terminal end of BAd3 pVIII there is a 67 amino acid stretch (residues 59 to 125; FIG. 8*a*) which has 75% identity with HAd2 pVIII. This region has previously been shown to be highly conserved among different Ads (Cladaras & Wold, 1985, supra; Signas, C., Akusjarvi, G. & Pettersson, U. (1986) *Gene*, 50:173–184,; Raviprakash et al., 1989, supra; Dragulev et al., 1991, supra).

The fibre protein is present on the surface of the virion as long projections from each vertex of the icosahedral capsid and is involved in a number of Ad functions including attachment of the virus to the cell surface during infection, assembly of virions and antigenicity (Philipson, L. (1983) *Current Topics in Microbiology and Immunology*, 109:1–52). On the basis of the primary structure of HAd2 fibre protein, it has been proposed that the shaft region (between amino acid residues 40 and 400) is composed of a number of repeating structural motifs containing about 15 hydrophobic residues organized in two short β-sheets and two β-bends (Green, N. M., Wrigley, N. G., Russell, W. C., Martin, S. R. & McLachlan, A. D. (1983) *EMBO Journal*, 2:1357–1365). The amino acid sequences at the N terminus of the BAV3 ORF 6-encoded protein share about 60% identity with the HAd2 fibre protein tail, but there is little or no similarity in the knob region, and about 45% identity overall (FIG. 8*c*). The BAd3 fibre gene would encode a protein of 976 residues if no splicing occurs, i.e. 394 amino acid residues longer than the HAd2 fibre protein. The number of repeating motifs in the shaft region of the fibre protein from different Ads varies between 28 and 23 (Signas et al., 1985, supra; Chroboczek, J. & Jacrot, B. (1987) *Virology*, 161:549–554; Hong et al., 1988, supra; Raviprakash et al., 1989, supra; Dragulev et al., 1991, supra). The BAV3 fibre protein can be organized into 52 such repeats in this region (not shown), which would account for most of the difference in size compared to those of HAd2, HAd3, HAD5, HAd7, CAd1 and MAd1 (Signas et al., 1985, supra; Hérissé et al., 1980, supra; Hérissé & Galibert, 1981, supra; Hong et al., 1988, supra; Raviprakash et al., 1989, supra; Dragulev et al., 1991, supra).

HAd2 and HAd5 E3 lies between the pVIII and the fibre genes an encodes at least 10 polypeptides (Cladaras & Wold, 1985, supra). The promoter for E3 of these two serotypes lies within the sequences encoding pVIII, about 320 bp 5' of the termination codon. No consensus TATA box is found in the corresponding region of the BAV3 sequences. A non-canonical polyadenylation signal (ATAAA) for E3 transcripts is located at position 1723, between the end of the putative E3 region and the beginning of ORF 6, encoding the fibre protein, and two consensus signals are located within ORF 6 at positions 2575 and 3565. The polyadenylation signal for the fibre protein is located at nucleotide 4877. Six ORFs were identified in the BAV3 genome between the pVIII and the fibre genes, but only four (ORFs 2, 3, 4 and 5) have the potential to encode polypeptides of at least 50 amino acids after an initiation codon (FIG. 7). The amino acid sequence predicted to be encoded by ORF 2 is 307 residues long and contains eight potential N-glycosylation sites (FIG. 7) as well as a hydrophobic sequence which may be a potential transmembrane domain (PLLFAFVLCTGCAVLLTAFGPSILSGT) (SEQ ID NO:32) between residues 262 and 289. This domain may be a part of the protein homologous to the HAd2 and HAd5 19K E3 glycoprotein (Cladaras & Wold, 1985, supra), and the proposed CAd1 22.2K protein (Dragulev et al., 1991, supra), but ORF 2 does not show appreciable homology with these proteins. The ORF 4 shows approximately 44% identity with the 14.7K E3 protein of HAd5 (FIGS. 6 and 8*b*), which has been shown to prevent lysis of virus-infected mouse cells by tumour necrosis factor (Gooding, L. R., Elmore, L. W., Tollefson, A. E., Brody, H. A. & Wold, W. S. M. (1988) *Cell*, 53:341–346; Wold, W. S. M. & Gooding, L. R. (1989) *Molecular Biology and Medicine*, 6:433–452). Analysis of the 14.7K protein sequence from HAd2, -3, -5 and -7 has revealed a highly conserved domain, which in HAd5 lies between amino acid residues 41 and 56 (Horton, T. M., Tollefson, A. E., Wold, W. S. M. & Gooding, L. R. (1990) *Journal of Virology*, 64:1250–1255). The corresponding region in the BAV3 ORF 4-encoded protein, between amino acids 70 and 85, contains 11 amino acids identical to those of the HAd5 14.7K protein conserved domain (FIG. 8*b*).

The BAV3 E3 region appears to be approximately 1.5 kbp long, about half the size of those of HAd2 and -5 (Cladaras & Wold, 1985, supra), and novel splicing events in BAV3 E3 would be required to generate more homologues 5 to the HAd3 E3 proteins. A similarly short E3 region has been reported for MAd1 (RAviprakash et al., 1989, supra) and CAd1 (Dragulev et al., 1991, supra).

Example 4

Construction of BAV3-luciferase Recombinants

Adenovirus-based mammalian cell expression vectors have gained tremendous importance in the last few years as a vehicle for recombinant vaccine delivery, and also in gene therapy. BAV3-based expression vectors have a greater potential for developing novel recombinant vaccines for veterinary use. To show that BAV3 E3 gene products are not essential for virus growth in cultured cells and this locus could be used to insert foreign DNA sequences, a 1.7 kb fragment containing the firefly luciferase gene was introduced in the 696 bp deletion of the E3 region of the BAV3 genome in the E3 parallel orientation to generate a BAV3 recombinant.

The rationale of using the luciferase gene is that it acted as a highly sensitive reporter gene when introduced in the E3 region of the HAd5 genome to generate HAd5-Luc recombinants (Mittal et al (1993) *Virus Res*. 28:67–90).

Figure 9:
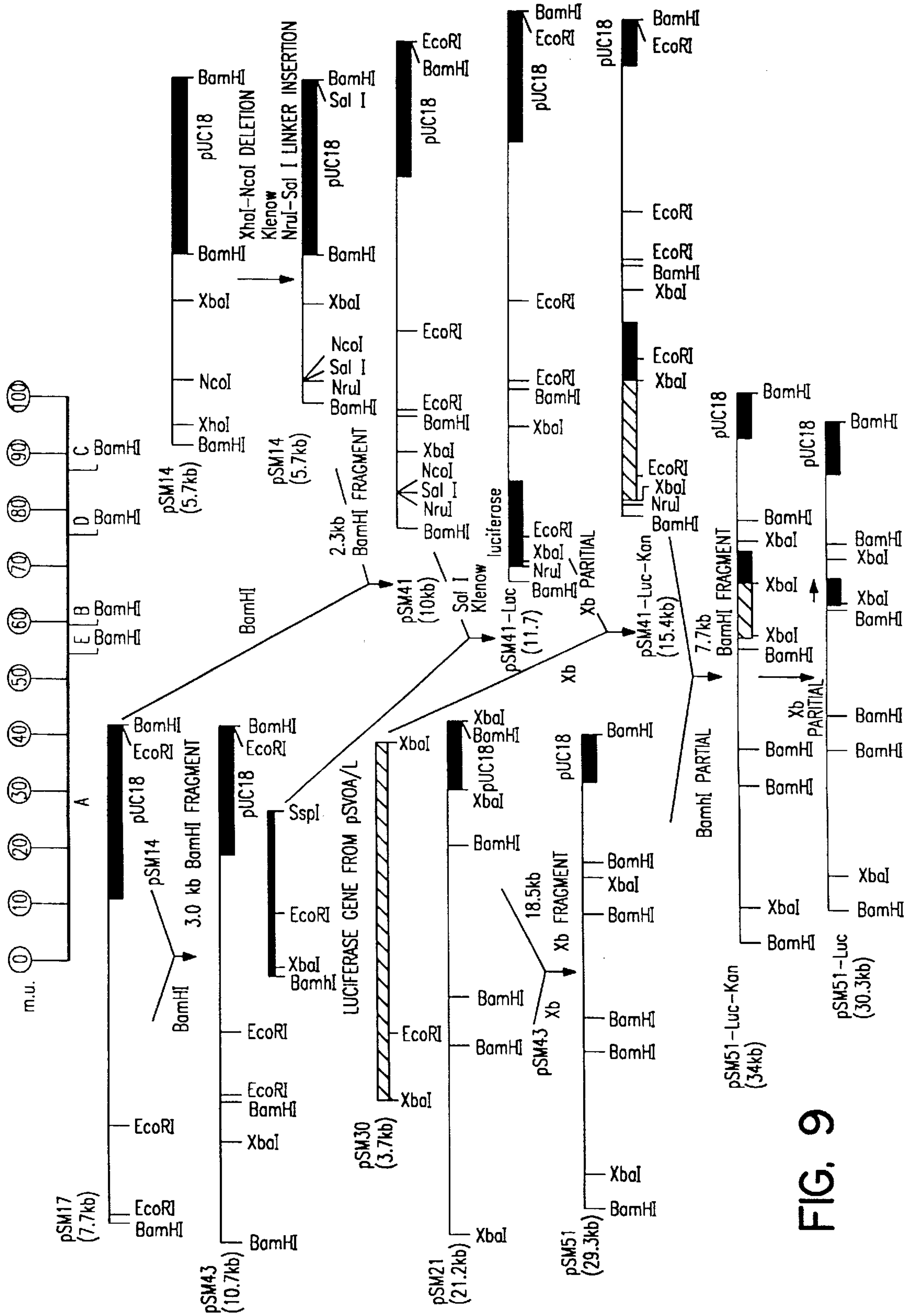
FIG. 9. Construction of BAV3 E3 transfer vector containing the firefly luciferase gene. The 3.0 kb BamHI 'D' fragment of the BAV3 genome which falls between m.u. 77.8 and 86.4, contains almost the entire E3 region (Mittal et al (1992) *J. Gen. Virol.* 73:3295–3000). This 3.0 kb fragment was isolated by digesting BAV3 DNA with BamHI and cloned into pUC18 at the BamHI site to obtain pSM14. Similarly, the 4.8 kb BamHI 'C' fragment of BAV3 DNA which extends between m.u. 86.4 and 100 was isolated and inserted into pUC18 to produce pSM17. To delete a 696 bp XhoI-NcoI fragment, pSM14 was cleaved with XhoI and NcoI, the larger fragment was purified and the ends were made blunt with Klenow fragment of DNA polymerase I and a NruI-SalI linker was inserted to generate pSM14de12. A 2.3 kb BamHI fragment containing BAV3 sequences, an E3 deletion and NruI and SalI cloning sites, was inserted into pSM17 at the BamHI site to obtain pSM41, however, this step was not required for construction of a BAV3 E3 transfer vector. A 1716 bp fragment containing the firefly luciferase gene (de Wet et al (1987) *Mol. Cell. Biol.* 7:725–737) was isolated by digesting pSVOA/L (provided by D. R. Helinski, University of California at San Diego, Calif.) with BsmI and SspI as described (Mittal et al (1993) *Virus Res.* 28:67–90), and the ends were made blunt with Klenow. The luciferase gene was inserted into pSM41 at the SalI site by blunt end ligation. The resultant plasmid was named pSM41-Luc which contained the luciferase gene in the same orientation as the E3 transcription unit. The plasmid pKN30 was digested with XbaI and inserted into pSM41-Luc (partially cleaved with XbaI) at a XbaI site present within the luciferase gene to obtain pSM41-Luc-Kan. The plasmid pSM14 was digested with BamHI and a 3.0 kb fragment was isolated and inserted into pSM17 at the BamHI site to generate pSM43. The 18.5 kb XbaI 'A' fragment of the BAV3 genome which falls between m.u. 31.5 and 84.3 was cloned into pUC18 at the XbaI site to result pSM21. A 18.5 kb XbaI fragment was purified from pSM21 after cleavage with XbaI and inserted into pSM43 at the XbaI site and the resultant plasmid was named pSM51. A 7.7 kb BamHI fragment containing the luciferase gene and $kan^r$ gene was isolated after digesting pSM41-Luc-Kan with BamHI and ligated to pSM51, partially digested with BamHI, to isolate pSM51-Luc-Kan in the presence of ampicillin and kanamycin. Finally the $kan^r$ gene was deleted from pSM51-Luc-Kan by partial cleavage with XbaI and religation to obtain pSM51-Luc.

To facilitate the insertion of the firefly luciferase gene into the E3 region of the BAV3 genome, a BAV3 E3 transfer vector containing the luciferase gene was constructed (FIG. 9). The BAV3 E3 region falls approximately between m.u. 77 and 82. In our first series of vectors we replaced a 696 bp XhoI-NcoI E3 deletion (between m.u. 78.8 and 80.8) with a NruI-SalI cloning sites for insertion of foreign genes to obtain pSM14de12. A 1716 bp BsmI-SspI fragment containing the luciferase gene was isolated and first inserted into an intermediate plasmid, pSM41, in the E3 locus at the SalI site by blunt end ligation to generate pSM41-Luc. The luciferase gene without any exogenous regulatory sequences, was inserted into the E3 locus in the same orientation as the E3 transcription unit. The kanr gene was inserted into pSM41-Luc at the XbaI site present within the luciferase gene to generate an $amp^r$/$kan^r$ plasmid, pSM41-Luc-Kan. A 7.7 kb fragment containing the BAV3 sequences along with the luciferase gene and the $kan^r$ gene was obtained from pSM41-Luc-Kan by digestion with BamHI and inserted into an $amp^r$ plasmid, pSM51 partially digested with BamHI to replace a 3.0 kb BamHI fragment (lies between m.u. 77.8 and 86.4) to generate a doubly resistant (kanr & ampr) plasmid, pSM51-Luc-Kan. The kanr gene was deleted from pSM51-Luc-Kan by partial cleavage with XbaI to generate pSM51-Luc containing the luciferase gene in the E3-parallel orientation.

Figure 10:
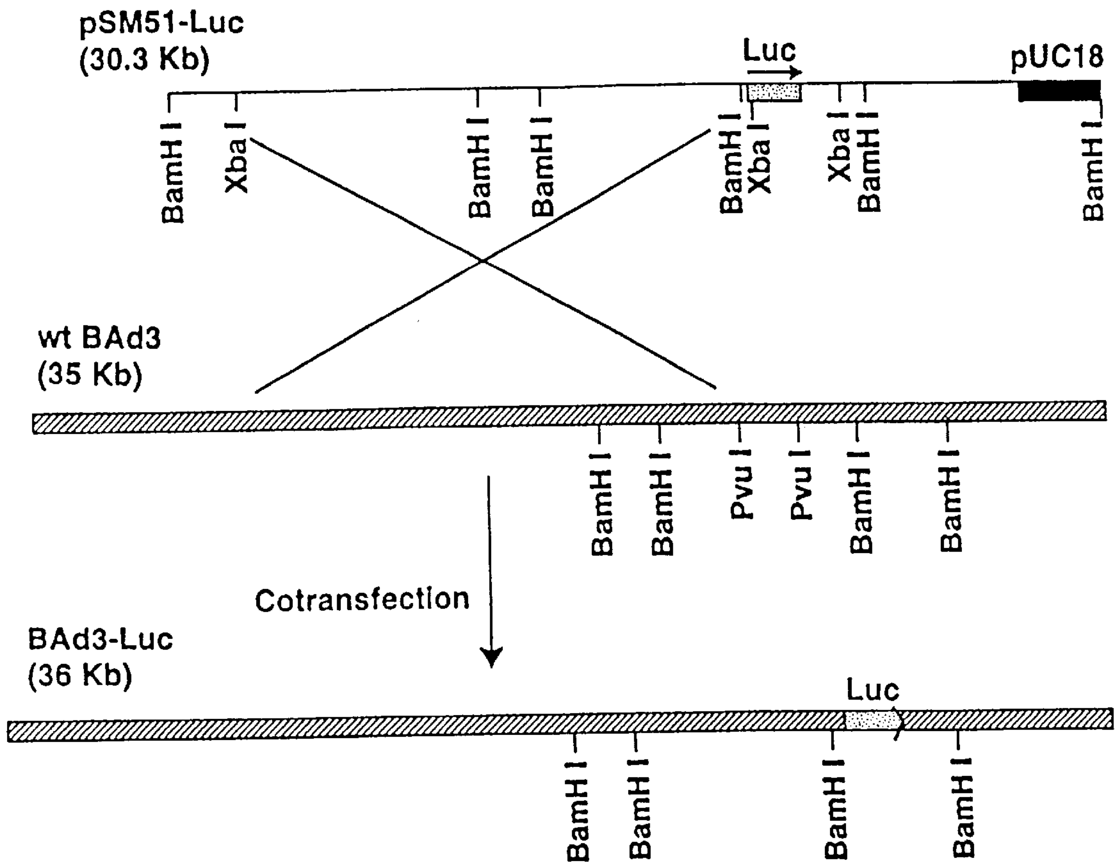
FIG. 10. Generation of BAV3 recombinants containing the firefly luciferase in the E3 region. The plasmid pSM51-Luc contains the BAV3 genome between m.u. 77.8–84.3 and 31.5–100, a 696 bp deletion in E3 and the luciferase gene in E3 in the E3 parallel orientation. The BAV3 genome digested with PvuI and uncut pSM51-Luc were used for cotransfection of MDBK cells transformed with a plasmid containing BAV3 E1 sequences to rescue the luciferase gene in E3 of the BAV3 genome by in vivo recombination. The resulting BAV3-luciferase recombinants (BAV3-Luc) isolated from two independent experiments were named BAV3-Luc (3.1) and BAV3-Luc (3.2). The BamHI restriction map of the BAV3-Luc genome is shown. The position and orientation of the firefly luciferase gene is shown as a hatched arrow.

MDBK cells transformed with a plasmid containing the BAV3 E1 sequences was cotransfected with the wt BAV3 DNA digested with PvuI, which make two cuts within the BAV3 genome at m.u 65.7 and 71.1, and the plasmid, pSM51-Luc to rescue the luciferase gene in E3 of the BAV3 genome by in vivo recombination (FIG. 10). The digestion of the wt BAV3 DNA with PvuI was helpful in minimizing the generation of the wt virus plaques following cotransfection. The left end of the wt BAV3 genome represented by PvuI 'A' fragment falls between m.u. 0 and 65.7, and pSM51-Luc which extends between m.u. 31.5 and 100 (except for E3 deletion replaced with the luciferase gene) have sufficient overlapping BAV3 DNA sequences to generate recombinant viruses.

Two virus plaques were obtained in two independent cotransfection experiments which were grown in MDBK cells. The viral DNA from both plaques was extracted and analyzed by agarose gel electrophoresis after digesting either with BamHI, EcoRI or XbaI to identify the presence and orientation of the luciferase gene in the viral genome (data not shown). In the genomes of both recombinants, the luciferase gene was present in the E3 region in the E3 parallel orientation. The BAV3-luciferase recombinants were plaque purified and named BAV3-Luc (3.1) and BAV3-Luc (3.2) to represent plaques obtained from two independent experiments. Since both recombinant virus isolates were identical they will be referred to as BAV3-Luc. The presence of the luciferase gene in BAV3-Luc isolates are further confirmed by Southern blot analyses and luciferase assays using extracts from recombinant virus-infected cells.

Characterization of BAV3-recombinants

Figure 11A:
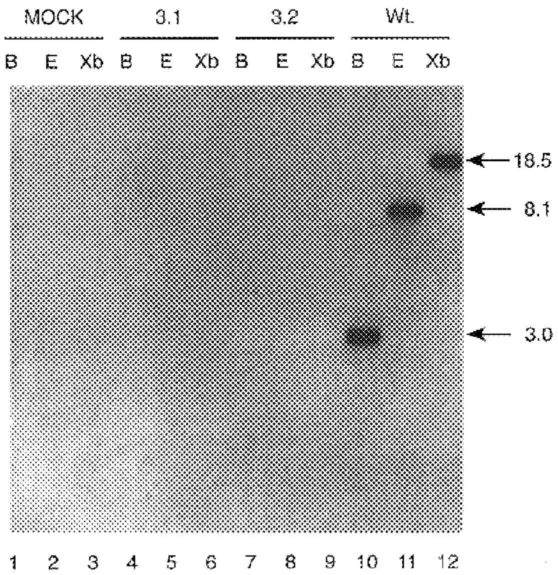
FIGS. 11A–11B. Southern blot analyses of restriction enzymes digested DNA fragments of the wt BAV3 or recombinant genomes by using a 696 bp XhoI-NcoI fragment from pSM14 (FIG. 9) and a DNA fragment containing the luciferase gene as probes. 100 ng DNA isolated from the mock (lanes 1, 2, 3), BAV3-Luc (3.1) (lanes 4, 5, 6), BAV3-Luc (3.2) (lanes 7, 8, 9) or wt BAV3 (lanes 10, 11 12)-infected MDBK cells were digested with BamHI (lanes 1, 4, 7, 10), EcoRI (lanes 2, 5, 8, 11) or XbaI (lanes 3, 6, 9, 12) and analyzed by agarose gel electrophoresis. The DNA fragments from the gel were transferred onto a GeneScreen-Plus™ membrane and hybridized with a 696 bp XhoI-NcoI fragment from pSM14 (FIG. 9) labeled with $^{32}P$ using Pharmacia Oligolabeling Kit (panel A). Panel B blot represents duplicate samples as in panel A but was probed with a 1716 bp BsmI-SspI fragment containing the luciferase gene (FIG. 9). The sizes of bands visualized following hybridization are shown in kb on the right in panel A and on the left in panel B.
Figure 11B:
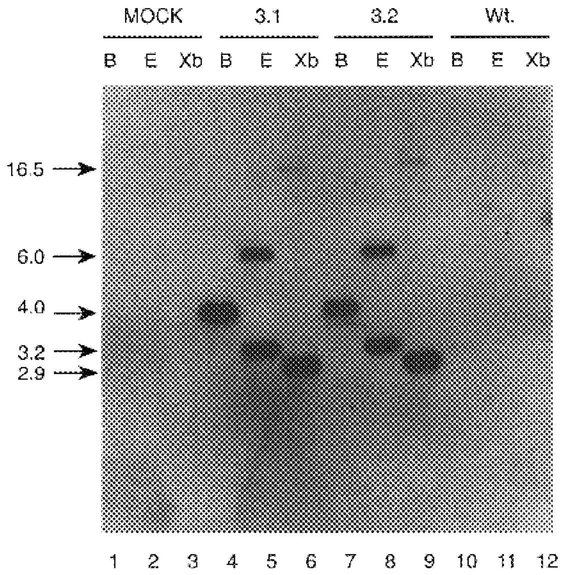

Southern blot analyses of the wt BAV3 and recombinants genomic DNA digested either with BamHI, EcoRI or XbaI, were carried out to confirm the presence and orientation of the luciferase gene in the E3 locus and the deletion of the 696 bp XhoI-NcoI fragment from E3 of the BAV3-Luc genome (FIG. 11). When the blot was probed with a 696 XhoI-NcoI fragment of E3 of the BAV3 genome (panel A, lanes 4 to 9) no hybridization signal was detected with the DNA fragments from the recombinant viruses, however, the expected bands (3.0 kb BamHI, 8.1 kb EcoRI, and 18.5 kb XbaI) of the wt BAV3 DNA fragments (panel A, lanes 10 to 12) showed hybridization, confirming that the 696 bp XhoI-NcoI fragment of the E3 region was indeed deleted in the BAV3-Luc genomic DNA. In panel B, when an identical blot was probed with the luciferase gene, there were strong hybridization signals with the DNA fragments from the recombinant viruses (4.0 kb BamHI (lane 4 & 7), 6.0 kb & 3.2 kb EcoRI (lanes 5 & 8), 16.7 kb & 2.9 kb XbaI (lanes 6 & 9)). These results confirmed that the BAV3-Luc contains the luciferase gene in the E3 parallel orientation with a 696 bp XhoI-NcoI E3 deletion.

The growth characteristics of the recombinant viruses was compared with the wt BAV3 in a single step growth curve (FIG. 12). Virus titers in MDBK cells-infected with the wt BAV3 started increasing at 12 h post-infection reaching a maximum at 36–48 h post-infection and then declined thereafter. Virus titers of the recombinant viruses also started increasing at 12 h postinfection reaching a maximum at 48 h post-infection and then declined, however, the titers of recombinant viruses remained approximately one log lower than the wt virus. The plaque size of the recombinant viruses were also comparatively smaller than the wt virus (data not shown).

Kinetics of Luciferase Expression by BAV3-Luc

Luciferase activity in BAV3-Luc-infected MDBK cells was monitored at different times post-infection by luciferase assays (FIG. 13). A low level of luciferase activity was first observed at 12 h post-infection reaching a peak at 30 h post-infection and then dropped subsequently. At 30 h post-infection, approximately 425 pg luciferase was detected in $4\times10^5$ BAV3-Luc (3.1)—infected MDBK cells. In MDBK cells-infected with the wt BAV3, luciferase expression was not detected (data not shown). The kinetics of luciferase expression by BAV3-Luc (3.1) and BAV3-Luc (3.2) appears very much similar. The kinetics of luciferase expression also showed that the majority of enzyme expression in virus-infected cells seemed to occur late in infection. To determine luciferase expression in the absence of viral DNA replication, BAV3-Luc-infected MDBK cells were incubated in the presence of an inhibitor of DNA synthesis, 1-β-D—arabinofuranosyl cytosine (AraC) and luciferase activity was measured in virus-infected cell extracts at various times post-infection and compared to luciferase expression obtained in the absence of AraC (FIG. 14). When the recombinant virus-infected cells were incubated in the presence of AraC, luciferase expression at 18, 24 and 30 h post-infection was approximately 20–30% of the value obtained in the absence of AraC. These results indicated that the majority of luciferase expression in MDBK cells infected with BAV3-Luc took place after the onset of viral DNA synthesis. To confirm this MDBK cells-infected with the BAV3-Luc were grown in the absence or presence of AraC, harvested at 18 h, 24 h, and 30 h post-infection, viral DNA extracted and analyzed by dot bot analysis using pSM51-Luc (see FIG. 9) as a probe (data not shown). In the presence of AraC, viral DNA synthesis was severely reduced compared to viral DNA synthesis in the absence of AraC.

Western Blot Analysis of BAV3-Luc-infected Cells

Luciferase was expressed as an active enzyme as determined by luciferase assays using extracts from MDBK cells-infected with BAV3-Luc (see FIG. 13). The luciferase gene without any exogenous regulatory sequences was inserted into E3 of the BAV3 genome, therefore, there was a possibility of luciferase expression as a fusion protein with part of an E3 protein if the luciferase gene was in the same frame, Such as, F1 and F3 which represent open reading frames (ORFs) for E3 proteins (FIG. 15) or the fusion protein may arise due to recognition of an upstream initiation codon in the luciferase ORF. To explore this possibility we sequenced the DNA at the junction of the luciferase gene and the BAV3 sequences with the help of a plasmid, pSM51-Luc and a synthetic primer design to bind luciferase coding sequences near the initiation codon (data not shown). The luciferase coding region fell in frame F2. The luciferase initiation codon was the first start codon in this frame, however, the ORF started at 84 nucleotides upstream of the luciferase start codon. To further confirm that luciferase protein is of the same molecular weight as purified firefly luciferase, unlabeled mock-infected, wt BAV3-infected or BAV3-Luc-infected MDBK cell extracts were reacted with an anti-luciferase antibody in a Western blot (FIG. 16). A 62 kDa polypeptide band was visible in the BAV3-Luc (lane 3 and 4)-infected cell extracts which were of the same molecular weight as pure firefly luciferase (lane 5). We are not sure whether a band of approximately 30 kDa which also reacted with the anti-luciferase antibody in lanes 3 and 4 represented a degraded luciferase protein.

The majority of luciferase expression is probably driven from the major late promoter (MLP) to provide expression paralleling viral late gene expression, moreover, the enzyme expression seen in the presence of AraC may be taking place from the E3 promoter. In HAd5 vectors, foreign genes without any exogenous regulatory sequences when inserted in E3 also displayed late kinetics and were inhibited by AraC. The BAV3 recombinant virus replicated relatively well in cultured cells but not as good as the wt BAV3. This is not surprising as infectious virus titers of a number of HAd5 recombinants were slightly lower than the wt HAd5 (Bett et al (1993) *J. Virol.* 67:5911–5921). This may be because of reduced expression of fiber protein in recombinant adenoviruses having inserts in the E3 region compared to the wt virus (Bett et al, supra and Mittal et al (1993) *Virus Res.* 28:67–90).

The E3 of BAV3 is approximately half the size of the E3 region of HAd2 or HAd5 and thus has the coding potential for only half the number of proteins compared to E3 of HAd2 or HAd5 (Cladaras et al (1985) *Virology* 140:28–43: Herisse et al (1980) *Nuc. Acids Res.* 8:2173–2192; Herisse et al (1981) *Nuc. Acids Res.* 9:1229–1249 and Mittal et al (1993 *J. Gen. Virol.* 73:3295–3000). BAV3 E3 gene products have been shown to be not required for virus growth in tissue culture. However, presently it is known that BAV3 E3 gene products also evade immune surveillance in vivo like HAds E3 proteins. One of the BAV3 E3 open reading frames (ORFs) has been shown to have amino acid homology with the 14.7 kDa E3 protein of HAds (Mittal et al (1993) supra). The 14.7 kDa E3 protein of HAds prevents lysis of virus-infected mouse cells by tumour necrosis factor (Gooding et al (1988) *Cell* 53:341–346 and Horton et al (1990) *J. Virol.* 64:1250–1255). The study of pathogenesis and immune responses of a series of BAV3 E3 deletion mutants in cattle provides very useful information regarding the role of E3 gene products in modulating immune responses in their natural host.

The BAV3-based vector has a 0.7 kb E3 deletion which can hold an insert up to 2.5 kb in size. The BAV3 E3 deletion can extend probably up to 1.4 kb which in turn would also increase the insertion capacity of this system. The role of the MLP and the E3 promoter is examined to determine their ability to drive expression of a foreign gene inserted into E3 when a proper polyadenylation signal is provided. Exogenous promoters, such as, the simian virus 40 (SV40) promoter (Subramant et al (1983) *Anal. Biochem.* 135:1–15), the human cytomegalovirus immediate early promoter (Boshart et al (1985) *Cell* 43:215–222), and the human beta-actin promoter (Gunning et al (1987) *PNAS, USA* 84:4831–4835) are tested to evaluate their ability to facilitate expression of foreign genes when introduced into E3 of the BAV3 genome.

Recently HAd-based expression vectors are under close scrutiny for their potential use in human gene therapy (Ragot et al (1993) *Nature* 361:647–650; Rosenfeld et al (1991) *Science* 252:431–434; Rosenfeld et al (1992) *Cell* 68:141–155 and Stratford-Perricaudet et al (1990) *Hum. Gene. Ther.* 1:241–256). A preferable adenovirus vector for gene therapy would be one which maintains expression of the required gene for indefinite or for a long period in the target organ or tissue. It may be obtained if the recombinant virus vector genome is incorporate into the host genome or maintained its independent existence extrachromosomally without active virus replication. HAds replicate very well in human, being their natural host. HAds can be made defective in replication by deleting the E1 region, however, how such vectors would maintain the expression of the target gene in a required fashion is not very clear. Moreover, the presence of anti-HAds antibodies in almost every human being may create some problems with the HAd-based delivery system. The adenovirus genomes have a tendency to form circles in non-permissive cells. BAV-based vectors could provide a possible alternative to HAd-based vectors for human gene therapy. As BAV3 does not replicate in human, the recombinant BAV3 genomes may be maintained as independent circles in human cells providing expression of the essential protein for a long period of time.

The foreign gene insertion in animal adenoviruses is much more difficult than HAds because it is hard to develop a cell line which is also good for adenovirus DNA-mediated transfection. This may be one of the major reasons that the development of an animal adenovirus-based expression system has not been reported so far. It took us more than a year to isolate a cell line suitable for BAV3 DNA-mediated transfection. However, the rapid implementation of BAV-based expression vectors for the production of live virus recombinant vaccines for farm animals, is very promising. BAVs grow in the respiratory and gastrointestinal tracts of cattle, therefore, recombinant BAV-based vaccines have use to provide a protective mucosal immune response, in addition to humoral and cellular immune responses, against pathogens where mucosal immunity plays a major role in protection.

Example 5

Generation of Cell Lines Transformed with the BAV3 E1 Sequences

MDBK cells in monolayer cultures were transfected with pSM71-neo, pSM61-kan1 or pSM61-kan2 by a lipofection-mediated transfection technique (GIBCO/BRL, Life Technologies, Inc., Grand Island, N.Y.). At 48 h after transfection, cells were maintained in the MEM supplemented with 5% fetal bovine serum and 700 μg/ml G418. The medium was changed every 3rd day. In the presence of G418, only those cells would grow which have stably incorporated the plasmid DNA used in transfection experiments into their genomes and are expressing the $neo^r$ gene. The cells which have incorporated the $neo^r$ gene might also have taken up the BAV3 E1 sequences and thus expressing BAV3 E1 protein/s. A number of $neo^r$ (i.e., G418-resistant) colonies were isolated, expended and tested for the presence of BAV3 E1 message/s by Northern blot analyses using a DNA probe containing only the BAV3 E1 sequences. Expression of BAV3 E1 protein/s were confirmed by a complimentation assay using a HAd5 deletion mutant defective in E1 function due to an E1 deletion.

Fetal bovine kidney cells in monolayers were also transfected with pSM71-neo, pSM61kan-1 or pSM61-kan2 by the lipofection-mediated transfection technique, electroporation (Chu et al (1987) *Nucl. Acids Res.* 15:1311–1326), or calcium phosphate precipitation technique (Graham et al (1973) *Virology* 52:456–467). Similarly, a number of G418-resistant colonies were isolated, expended and tested for the presence of BAV3 E1 gene products as mentioned above.

Example 6

Generation of a BAV3 Recombinant Containing the Beta-galactosidase Gene as an E1 Insert As E1 gene products are essential for virus replication, adenovirus recombinants containing E1 inserts will grow only in a cell line which is transformed with the adenovirus E1 sequences and expresses E1. A number of cell line which are transformed with the BAV3 E1 sequences were isolated as described earlier. The technique of foreign gene insertions into the E1 regions is similar to the gene insertion into the E3 region of the BAV3 genome, however, for insertion into E1 there is a need of an E1 transfer plasmid which contains DNA sequences from the left end of the BAV3 genome, an appropriate deletion and a cloning site for the insertion of foreign DNA sequences. G418-resistant MDBK cell monolayers were cotransfected with the wild-type (wt) BAV3 DNA and pSM71-Z following the lipofection-mediated transfection procedure (GIBCO/BRL, Life Technologies, Inc., Grand Island, N.Y.). The monolayers were incubated at 37° C. under an agarose overlay. After a week post-incubation an another layer of overlay containing 300 ug/ml Blu-gal™ (GIBCO/BRL Canada, Burlington, Ontario, Canada) was put onto each monolayer. The blue plaques were isolated, plaque purified and the presence of the beta-galactosidase gene in the BAV3 genome was identified by agarose gel electrophoresis of recombinant virus DNA digested with suitable restriction enzymes and confirmed by beta-galactosidase assays using extracts from recombinant virus infected cells.

Deposit of Biological Materials

The following materials were deposited and are maintained with the Veterinary Infectious Disease Organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material | Internal Accession No. | Deposit Date |
|---|---|---|
| Recombinant plasmids | | |
| pSM51 | pSM51 | Dec 6, 1993 |
| pSM71 | pSM71 | Dec 6, 1993 |
| Recombinant cell lines | | |
| MDBK cells transformed with BAV3 E1 sequences (MDBK-BAVE1) | | Dec 6, 1993 |
| Fetal bovine kidney cells transformed with BAV3 E1 sequences (FBK-BAV-E1) | | Dec 6, 1993 |

While the present invention has been illustrated above by certain specific embodiments, the specific examples are not intended to limit the scope of the invention as described in the appended claims.

We claim:

1. A live viable recombinant bovine adenovirus (BAV) for producing a desired immune response in a mammalian host comprising:

(a) a live BAV modified to contain a heterologous nucleotide sequence coding for a polypeptide or an antigenic determinant corresponding to the desired immune response, said heterologous nucleotide sequence in association with:

(b) an effective promoter for said heterologous nucleotide sequence to provide expression of said polypeptide or antigenic determinant in immunogenic, non-pathogenic quantities.

2. The recombinant BAV of claim 1 wherein said effective promoter is an endogenous BAV promoter.

3. The recombinant BAV of claim 1 wherein said effective promoter is a heterologous promoter.

4. A recombinant virus genome produced by in vivo recombination between a nonrecombinant virus genome and a plasmid, said nonrecombinant virus genome comprising the BAV genome;

said plasmid comprising bovine adenovirus left end nucleotide sequences comprising the E1 multiple gene coding region;

said plasmid further comprising heterologous nucleotide sequence encoding a foreign gene or fragment thereof substituted for part or all of the E1 multiple gene coding region;

said in vivo recombination following cotransfection of a suitable cell line by said nonrecombinant virus genome and said plasmid.

5. A recombinant virus genome produced by in vivo recombination between a nonrecombinant virus genome and a plasmid, said nonrecombinant virus genome comprising the BAV genome;

said plasmid comprising bovine adenovirus right end nucleotide sequences comprising the E3 multiple gene coding region;

said plasmid further comprising heterologous nucleotide sequence encoding a foreign gene or fragment thereof substituted for part or all of the E3 multiple gene coding region;

said in vivo recombination following cotransfection of a suitable cell line by said nonrecombinant virus genome and said plasmid.

6. A recombinant virus genome produced by in vivo recombination between a nonrecombinant virus genome and two plasmids, said nonrecombinant virus genome comprising the BAV genome;

one of said plasmids comprising bovine adenovirus left end nucleotide sequences comprising the E1 multiple gene coding region;

the other of said plasmids comprising bovine adenovirus right end nucleotide sequences comprising the E3 multiple gene coding region;

one or both of said plasmids further comprising heterologous nucleotide sequences encoding one or more foreign genes or fragments thereof substituted for part or all of the E1 and/or E3 multiple gene coding regions;

said in vivo recombination following cotransfection of a suitable cell line by said nonrecombinant virus genome and said plasmids.

7. A live viable recombinant bovine adenovirus (BAV) containing a bovine adenovirus subgroup 1 genome with a deletion of part or all of the E1 multiple gene coding region, said deletion being replaced by a heterologous nucleotide sequence coding for a polypeptide produced by a disease causing organism or an antigenic determinant produced by a disease causing organism.

8. A live viable recombinant bovine adenovirus (BAV) containing a bovine adenovirus subgroup 1 genome with a deletion of part or all of the E3 multiple gene coding region, said deletion being replaced by a heterologous nucleotide sequence coding for a polypeptide produced by a disease causing organism or an antigenic determinant produced by a disease causing organism.

9. A live viable recombinant bovine adenovirus (BAV) containing a bovine adenovirus subgroup 1 genome with deletions in both the E1 and E3 multiple gene coding regions, said deletions being replaced by heterologous nucleotide sequences coding for polypeptides produced by one or more disease causing organisms or antigenic determinants produced by one or more disease causing organisms.

10. A live viable recombinant bovine adenovirus (BAV) for producing an immune response in a mammalian host comprising a bovine adenovirus (BAV) subgroup 1 genome modified in the E1 multiple gene coding region to contain a heterologous nucleotide sequence coding for a polypeptide or an antigenic determinant capable of eliciting a desired immune response, wherein said heterologous nucleotide sequence is in association with an effective promoter.

11. A method for eliciting an immune response in a mammalian host to protect against an infection comprising administering a vaccine composition comprising:

(a) a live recombinant BAV of claim 10 wherein the heterologous nucleotide sequence encodes an antigen; and (b) a pharmaceutically acceptable excipient.

12. A vaccine for protecting a mammalian host against infection comprising:

(a) a live recombinant BAV of claim 10 wherein the heterologous nucleotide sequence encodes an antigen; and (b) a pharmaceutically acceptable excipient.

13. A live recombinant bovine adenovirus vector (BAV) selected from the group consisting of:

(a) a bovine adenovirus subgroup 1 genome wherein part or all of the E1 multiple gene coding region is replaced by a heterologous nucleotide sequence encoding a foreign gene or fragment thereof;

(b) a bovine adenovirus subgroup 1 genome wherein a part or all of the E3 multiple gene coding region is replaced by a heterologous nucleotide sequence encoding a foreign gene or fragment thereof; and (c) a bovine adenovirus subgroup 1 genome wherein part or all of the E1 multiple gene coding region and part or all of the E3 multiple gene coding region are deleted and a heterologous nucleotide sequence encoding a foreign gene or fragment thereof is inserted into at least one of the deletions.

14. The vector of claim 13 which is a bovine adenovirus type 3.

15. The vector of claim 13 wherein part or all of the E1 multiple gene coding region is replaced by a heterologous nucleotide sequence encoding a foreign gene or fragment thereof.

16. The vector of claim 13 wherein part or all of the E1 multiple gene coding region and part or all of the E3 multiple gene coding region are deleted and a heterologous nucleotide sequence encoding a foreign gene or fragment thereof is inserted into at least one of the deletions.

17. The recombinant BAV of claim 13 wherein part or all of the E1 multiple gene coding region is replaced by a heterologous nucleotide sequence encoding a foreign gene or fragment thereof and wherein said heterologous nucleotide sequence is under the control of a promoter not normally associated with either said foreign gene or the bovine adenovirus genome.

18. The recombinant BAV of claim 13 wherein part or all of another viral gene is deleted.

19. A method for eliciting an immune response in a mammalian host to protect against an infection comprising:

administering a vaccine composition comprising a live recombinant BAV of claim 14 wherein the foreign gene or fragment thereof encodes an antigen.

20. A vaccine for protecting a mammalian host against infection comprising a live recombinant BAV of claim 13 wherein the foreign gene or fragment thereof encodes an antigen.

21. A live recombinant bovine adenovirus (BAV) expression vector comprising a bovine adenovirus subgroup 1 genome with a deletion of all or part of the E1 multiple gene coding region;

said expression vector further comprising an insertion, at the site of the deletion, of a heterologous nucleotide sequence coding for a foreign gene or fragment thereof, said heterologous nucleotide sequence being under the control of an effective promoter and optionally one or more polyadenylation signals.

22. A live recombinant bovine adenovirus (BAV) expression vector comprising a bovine adenovirus subgroup 1 genome with a deletion of all or part of the E3 multiple gene coding region;

said expression vector further comprising an insertion, at the site of the deletion, of a heterologous nucleotide sequence coding for a foreign gene or fragment thereof, said heterologous nucleotide sequence being under the control of an effective promoter and optionally one or more polyadenylation signals.

23. A live recombinant bovine adenovirus (BAV) expression vector comprising a bovine adenovirus subgroup 1 genome with deletions of all or part of the E1 multiple gene coding region and all or part of the E3 multiple gene coding region;

said expression vector further comprising one or more insertions, at the site of at least one of the deletions, of one or more heterologous nucleotide sequences coding for one or more foreign genes or fragments thereof, said heterologous nucleotide sequences being under the control of one or more effective promoters and optionally one or more polyadenylation signals.

24. A mutant subgroup 1 bovine adenovirus (BAV) comprising a deletion of part or all of the E1 multiple gene coding region.

25. A mutant subgroup 1 bovine adenovirus (BAV) comprising a deletion of part or all of the E3 multiple gene coding region.

26. A mutant subgroup 1 bovine adenovirus (BAV) comprising deletions of part or all of the E1 multiple gene coding region and part or all of the E3 multiple gene coding region.

* * * * *

UNITED STATES PATENT AND TRADEMARK OFFICE

CERTIFICATE OF CORRECTION

PATENT NO. : 6,086,890
DATED : July 11, 2000
INVENTOR(S) : Suresh K. Mittal et al.

It is certified that error appears in the above-identified patent and that said Letters Patent is hereby corrected as shown below:

Claim 19, column 113,
Line 36, please replace "14" with -- 13 --.

Signed and Sealed this

Eighteenth Day of September, 2001

*Attest:*

NICHOLAS P. GODICI

*Attesting Officer* *Acting Director of the United States Patent and Trademark Office*